(12) United States Patent
Schirok et al.

(10) Patent No.: US 7,723,347 B2
(45) Date of Patent: May 25, 2010

(54) SUBSTITUTED PHENYLAMINO-PYRIMIDINES

(75) Inventors: Hartmut Schirok, Wuppertal (DE); Johannes-Peter Stasch, Solingen (DE); Raimund Kast, Wuppertal (DE); Klaus Münter, Wülfrath (DE); Marc Jean Gnoth, Mettmann (DE); Santiago Figureoa Perez, Leverkusen (DE); Michael Thutewohl, Buchs (CH); Samir Bennabi, Caluire et Cuire (FR); Dieter Lang, Velbert (DE); Joachim Mittendorf, Wuppertal (DE); Martin Radtke, Erkrath (DE); Heimo Ehmke, Hamburg (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 378 days.

(21) Appl. No.: 11/587,630

(22) PCT Filed: Apr. 14, 2005

(86) PCT No.: PCT/EP2005/003925

§ 371 (c)(1),
(2), (4) Date: Aug. 15, 2007

(87) PCT Pub. No.: WO2005/108397

PCT Pub. Date: Nov. 17, 2005

(65) Prior Publication Data

US 2008/0269268 A1    Oct. 30, 2008

(30) Foreign Application Priority Data

Apr. 27, 2004  (DE) .................. 10 2004 020 570

(51) Int. Cl.
*C07D 471/04* (2006.01)
*A61K 31/437* (2006.01)

(52) U.S. Cl. ...................... 514/275; 544/324
(58) Field of Classification Search ................ 544/324; 514/275
See application file for complete search history.

(56) References Cited

FOREIGN PATENT DOCUMENTS

| WO | 0128561 | 4/2001 |
|---|---|---|
| WO | 03002542 | 1/2003 |
| WO | 03062225 | 7/2003 |
| WO | 03062227 | 7/2003 |
| WO | 03106450 | 12/2003 |
| WO | 2004039796 | 5/2004 |

OTHER PUBLICATIONS

Vippagunta et al., Cyrstalline Solids, Advanced Drug Delivery Reviews, 48, pp. 3-26, 2001.*
Ulrich, Chapter 4: Crystallization, Kirk-Othmer Encyclopedia of Chemical Technology, Aug. 2002.*
West, Solid Solutions, Solid State Chemistry and its applications, pp. 358 & 365, 1988.*
Somlyo, et al., "Cell Calcium and Its Regulation in Smooth Muscle", The FASEB Journal, 3:2266-2276 (1989).
Kamm, et al., "The Function of Myosin and Myosin Light Chain Kinase Phosphorylation in Smooth Muscle", Ann. Rev. Pharmacol. Toxicol., 25:593-620 (1985).
Noda, et al., "Involvement of Rho in GTPγS-induced Enhancement of Phosphorylation of 20 kDa Myosin Light Chain in Vascular Smooth Muscle Cells: Inhibition of Phosphatase Activity", FEBS letters, 367:246-350 (1995).
Uehata, et al., "Calcium Sensitization of Smooth Muscle Mediated by a RHO-associated Protein Kinase in Hypertension", Nature, 389:990-994 (1997).
Fukata, et al., "Rho-Rho-Kinase Pathway in Smooth Muscle Contraction and Cytoskeletal Reorganization of Non-Muscle Cells", TRENDS in Pharmacological Sciences, 22:32-39 (2001).
Itoh, et al., "An Essential Part for Rho-associated Kinase in the Transcellular Invasion of Tumor Cells", Nature Medicine, 5:221-225 (1999).
Somlyo, et al., "Rho-Kinase Inhibitor Retards Migration and in Vivo Dissemination of Human Prostate Cancer Cells", Biochemical and Biophysical Research Communications, 269:652-659 (2000).
Uchida, et al., "The Suppression of Small GTPase Rho Signal Transduction Pathway Inhibits Angiogenesis in Vitro and in Vivo", Biochemical and Biophysical Research Communications, 269:633-640 (2000).
Gingras, et al., "Tyrosine Phosphorylation of the Vascular Endothelial-Growth-Factor Receptor-2 (VEGFR-2) is modulated by Rho Proteins", Biochem. J., 348:273-280 (2000).

* cited by examiner

Primary Examiner—Deepak Rao
(74) Attorney, Agent, or Firm—Thomas C. Blankinship

(57) ABSTRACT

The invention relates to substituted phenylaminopyrimidines, to a process for their preparation and to their use for preparing medicaments for the treatment and/or prophylaxis of diseases in humans and animals, in particular cardiovascular disorders.

9 Claims, No Drawings

SUBSTITUTED PHENYLAMINO-PYRIMIDINES

This application is a 371 of PCT/EP05/03925 filed Apr. 14, 2005.

The invention relates to substituted phenylaminopyrimidines, to a process for their preparation and to their use for preparing medicaments for the treatment and/or prophylaxis of diseases in humans and animals, in particular cardiovascular disorders.

An increase in the intracellular calcium concentration is one of the main factors triggering the contraction of the vascular musculature (Somlyo, A. P. and Himpens, B. *FASEB J.* 1989, 3, 2266-2276). This is effected primarily by agonists, such as, for example, phenylephrine or thromboxane A2 which, after stimulation of the phosphatidylinositol cascade, cause the release of calcium from the sarcoplasmatic reticulum. The elevated intracellular calcium activates the MLC kinase (myosin light-chain kinase) which phosphorylates the MLC subunits of the myosin molecule (Kamm, K. H. and Stull, J. T., *Annu. Rev. Pharmacol. Toxicol.* 1985, 25, 593-603). MLC phosphorylation induces the contraction of smooth muscles, MLC dephosphorylation after reduction of the intracellular calcium concentration results in the relaxation of the vessel.

In addition to the calcium-dependent MLC phosphorylation, there is a further, central but calcium-independent, regulation mechanism of the vascular tone. This is the Rho/Rho kinase signal path (Noda, M. et al., *FEBS Lett.* 1995, 367, 246-250; Uehata, M. et al., *Nature* 1997, 389, 990-994; Fukata, Y. et al., *Trends in Pharmacological Sciences* 2001, 22, 32-39). The binding of agonists such as, for example, phenylephrine or thromboxane A2 to their receptors results in the activation of the small G-proteins Rho which then interact with and activate Rho kinase. The activated Rho kinase inhibits myosin phosphatase following phosphorylation of a subunit of the enzyme. At the same time, Rho kinase phosphorylates MLC at the position which is also phosphorylated by MLC kinase. Inhibition of myosin phosphatase and phosphorylation of MLC induces the vascular musculature to contract. In contrast, inhibition of Rho kinase leads to a relaxation of the vessels. Accordingly, inhibitors of Rho kinase lower the blood pressure and increase coronary perfusion.

In addition, inhibitors of Rho kinase cause inhibition of growth of tumor cells and metastases (Itoh et al. *Nat. Med.* 1999, 5, 221; Somlyo et al. *Biochem. Biophys. Res. Commun.* 2000, 269, 652) and inhibit angiogenesis (Uchida et al. *Biochem. Biophys. Res. Commun.* 2000, 269, 633; Gingras et al. *Biochem. J.* 2000, 348 Vol. 2, 273).

Structures similar to the compounds according to the invention are disclosed in WO 03/062225, WO 03/062227, WO 03/106450 and WO 04/039796 as rho-kinase inhibitors for the treatment of cancer and cardiovascular disorders. WO 03/02542 discloses inter alia substituted pyrimidines as p38 kinase inhibitors for the treatment of inflammatory and cardiovascular disorders.

Structures similar to the compounds according to the invention are furthermore known from other indications. Thus, for example, WO 01/28561 discloses substituted pyrimidines as DNA polymerase III inhibitors for the treatment of bacterial infections.

The present invention provides compounds of the formula (I)

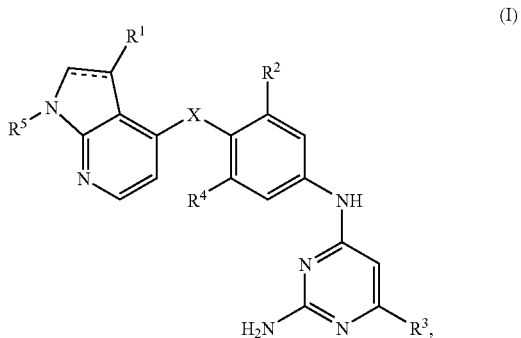

in which

=== represents a single bond or a double bond,

X represents —$NR^6$—, —$CR^7R^8$— or —$C(=O)$—, in which $R^6$ represents hydrogen or ($C_1$-$C_3$)-alkyl, $R^7$ and $R^8$ independently of one another represent hydrogen or methyl, $R^1$ represents hydrogen, halogen, cyano, ($C_1$-$C_6$)-alkyl, ($C_3$-$C_6$)-cycloalkyl, ($C_1$-$C_6$)-alkoxycarbonyl or ($C_1$-$C_6$)-alkylaminocarbonyl, where alkyl, alkoxycarbonyl and alkylaminocarbonyl for their part may be substituted by hydroxyl, halogen, hydroxycarbonyl, ($C_1$-$C_6$)-alkoxy, ($C_1$-$C_6$)-alkoxycarbonyl, amino, aminocarbonyl, ($C_1$-$C_6$)-alkylamino or ($C_1$-$C_6$)-alkylaminocarbonyl, $R^2$ represents fluorine or chlorine, $R^3$ represents a radical selected from the group consisting of:

hydrogen, hydroxyl, halogen, trifluoromethyl, pentafluoroethyl, ($C_1$-$C_6$)-alkyl, ($C_1$-$C_6$)-alkoxy, ($C_3$-$C_8$)-cycloalkyl, where alkyl, alkoxy and cycloalkyl for their part may be substituted by hydroxyl, hydroxycarbonyl, ($C_1$-$C_6$)-alkoxy, ($C_1$-$C_6$)-alkoxycarbonyl, ($C_6$-$C_{10}$)-aryl, —$NR^9R^{10}$ or —$C(=O)NR^9R^{10}$, in which $R^9$ and $R^{10}$ independently of one another represent hydrogen, ($C_1$-$C_8$)-alkyl, optionally ($C_1$-$C_6$)-alkyl-substituted ($C_3$-$C_6$)-cycloalkyl, optionally halogen-substituted ($C_6$-$C_{10}$)-aryl or 5- to 10-membered heteroaryl or $R^9$ and $R^{10}$ together with the nitrogen atom to which they are attached form a 5- or 6-membered heterocycle which may contain a further heteroatom O or N in the ring and which may be substituted by ($C_1$-$C_6$)-alkyl, ($C_1$-$C_6$)-alkanoyl or ($C_1$-$C_6$)-alkoxycarbonyl, ($C_6$-$C_{10}$)-aryl, ($C_6$-$C_{10}$)-aryloxy, 5- to 10-membered heteroaryl, 5- to 10-membered heteroaryloxy, 5- to 10-membered heterocyclyl which is attached via a carbon atom, where aryl, aryloxy, heteroaryl, heteroaryloxy and heterocyclyl for their part may be substituted by halogen, cyano, nitro, hydroxycarbonyl, amino, trifluoromethyl, optionally hydroxyl-substituted ($C_1$-$C_6$)-alkyl, ($C_1$-$C_6$)-alkoxy, ($C_1$-$C_6$)-alkylamino, ($C_1$-$C_6$)-alkanoyl, $(C_1\text{-}C_6)$-alkoxycarbonyl, $(C_1\text{-}C_6)$-alkanoylamino, $(C_1\text{-}C_6)$-alkoxycarbonylamino or 5- or 6-membered heterocyclyl,

—$NR^{11}R^{12}$, in which $R^{11}$ and $R^{12}$ independently of one another represent hydrogen, $(C_1\text{-}C_6)$-alkyl, $(C_3\text{-}C_8)$-cycloalkyl, $(C_6\text{-}C_{10})$-aryl or 5- to 10-membered heteroaryl, where alkyl and cycloalkyl for their part may be substituted by hydroxyl, $(C_1\text{-}C_6)$-alkoxy, $(C_6\text{-}C_{10})$-aryl, 5- to 10-membered heteroaryl or —$NR^{13}R^{14}$, in which $R^{13}$ and $R^{14}$ independently of one another represent hydrogen, $(C_1\text{-}C_6)$-alkyl, $(C_3\text{-}C_6)$-cycloalkyl, $(C_6\text{-}C_{10})$-aryl or 5- or 6-membered heteroaryl or $R^{13}$ and $R^{14}$ together with the nitrogen atom to which they are attached form a 5- or 6-membered heterocycle which may contain a further heteroatom O or N in the ring and which may be substituted by $(C_1\text{-}C_6)$-alkyl, $(C_1\text{-}C_6)$-alkanoyl or $(C_1\text{-}C_6)$-alkoxycarbonyl, and where aryl and heteroaryl for their part may be substituted by halogen, hydroxyl, amino, cyano, trifluoromethyl, $(C_1\text{-}C_6)$-alkyl, $(C_1\text{-}C_6)$-alkoxy, $(C_1\text{-}C_6)$-alkylamino or $(C_1\text{-}C_6)$-alkanoylamino, or $R^{11}$ and $R^{12}$ together with the nitrogen atom to which they are attached form a 4- to 6-membered heterocycle which may contain a further heteroatom O or N in the ring and which may be substituted by fluorine, hydroxyl, hydroxycarbonyl, 5- to 7-membered heterocyclyl which may contain one or two further heteroatoms N and/or O in the ring and which for its part may be substituted by $(C_1\text{-}C_4)$-alkyl or $(C_1\text{-}C_4)$-alkoxycarbonyl, $(C_1\text{-}C_4)$-alkoxy, $(C_1\text{-}C_4)$-alkyl, $(C_1\text{-}C_4)$-alkanoyl, $(C_1\text{-}C_4)$-alkoxycarbonyl or —$NR^{11}R^{16}$ where alkyl for its part may be substituted by hydroxyl, $(C_1\text{-}C_4)$-alkoxy or —$NR^{17}R^{18}$, where $R^{17}$ and $R^{18}$ independently of one another represent hydrogen, optionally hydroxyl-substituted $(C_1\text{-}C_6)$-alkyl, $(C_3\text{-}C_6)$-cycloalkyl, $(C_6\text{-}C_{10})$-aryl or 5- to 6-membered heteroaryl or $R^{17}$ and $R^{18}$ together with the nitrogen atom to which they are attached form a 5- or 6-membered heterocycle which may contain a further heteroatom O or N in the ring and which may be substituted by $(C_1\text{-}C_6)$-alkyl, $(C_1\text{-}C_6)$-alkanoyl or $(C_1\text{-}C_6)$-alkoxycarbonyl, in which $R^{15}$ and $R^{16}$ independently of one another represent hydrogen, $(C_1\text{-}C_6)$-alkyl, $(C_1\text{-}C_4)$-alkoxycarbonyl, $(C_3\text{-}C_8)$-cycloalkyl or $(C_1\text{-}C_4)$-alkanoyl or $R^{15}$ and $R^{16}$ together with the nitrogen atom to which they are attached form a 5- or 6-membered heterocycle which may contain a further heteroatom O or N in the ring and which may be substituted by $(C_1\text{-}C_6)$-alkyl, $(C_1\text{-}C_6)$-alkanoyl or $(C_1\text{-}C_6)$-alkoxycarbonyl, or $R^{11}$ and $R^{12}$ together with the nitrogen atom to which they are attached form a 7- to 12-membered bicyclic or tricyclic heterocycle which is fused or spirocyclic and which may have one or two further heteroatoms from the group consisting of N and O in the ring and which may be substituted by fluorine, $(C_1\text{-}C_4)$-alkyl, $(C_1\text{-}C_4)$-alkoxycarbonyl, $(C_1\text{-}C_4)$-alkanoyl or benzyl, and —$C(=O)R^{19}$, in which $R^{19}$ represents $(C_1\text{-}C_6)$-alkoxy, $(C_1\text{-}C_6)$-alkylamino or a 5- to 10-membered mono- or bicyclic heterocycle which is attached via a nitrogen atom, which is fused or spirocyclic and which may have one or two further heteroatoms from the group consisting of N and O in the ring, where alkylamino for its part may be substituted by a 5- or 6-membered heterocycle, $R^4$ represents hydrogen, fluorine or chlorine, $R^5$ represents hydrogen or $(C_1\text{-}C_6)$-alkyl and their salts, hydrates, hydrates of the salts and solvates.

Compounds according to the invention are the compounds of the formula (I) and their salts, solvates and solvates of the salts; the compounds of the formulae given below embraced by formula (I) and their salts, solvates and solvates of the salts and the compounds given below as embodiments and embraced by formula (I) and their salts, solvates and solvates of the salts, if the compounds given below and embraced by formula (I) are not already salts, solvates and solvates of the salts.

Depending on their structure, the compounds according to the invention can exist in stereoisomeric forms (enantiomers, diastereomers). Accordingly, the invention relates to the enantiomers or diastereomers and to their respective mixtures. The stereoisomerically uniform components can be isolated in a known manner from such mixtures of enantiomers and/or diastereomers.

If the compounds according to the invention can be present in tautomeric forms, the present invention includes all tautomeric forms.

In the context of the invention, preferred salts are physiologically acceptable salts of the compounds according to the invention. However, also included are salts which per se are not suitable for pharmaceutical applications but which, for example, can be used for isolating or purifying the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid or benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds which, in solid or liquid state, form a complex by coordination with solvent molecules. Hydrates are a specific form of solvents where the coordination is with water.

In the context of the present invention, the substituents are as defined below, unless specified otherwise:

alkyl per se and "alk" and "alkyl" in alkoxy, alkanoyl, alkylamino, alkylaminocarbonyl, alkoxycarbonyl, alkoxycarbonylamino and alkanoylamino represent a straight-chain or branched alkyl radical having generally 1 to 6, preferably 1 to 4, particularly preferably 1 to 3, carbon atoms, by way of example and by way of preference methyl, ethyl, n-propyl, isopropyl, tert-butyl, n-pentyl and n-hexyl.

By way of example and by way of preference, alkoxy represents methoxy, ethoxy, n-propoxy, isopropoxy, tert-butoxy, n-pentoxy and n-hexoxy.

By way of example and by way of preference, alkanoyl represents acetyl and propanoyl.

Alkylamino represents an alkylamino radical having one or two alkyl substituents (selected independently of one another), by way of example and by way of preference methylamino, ethylamino, n-propylamino, isopropylamino, tert-butylamino, n-pentylamino, n-hexylamino, N,N-dimethylamino, N,N-diethylamino, N,N-diisopropylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_4$-Alkylamino, for example, represents a monoalkylamino radical having 1 to 4 carbon atoms or represents a dialkylamino radical having in each case 1 to 4 carbon atoms per alkyl substituent.

Alkylaminocarbonyl represents an alkylaminocarbonyl radical having one or two alkyl substituents (chosen independently of one another). ($C_1$-$C_3$)-alkylaminocarbonyl, for example, represents a monoalkylaminocarbonyl radical having 1 to 3 carbon atoms or represents a dialkylaminocarbonyl radical having in each case 1 to 3 carbon atoms per alkyl substituent. The following may be mentioned by way of example and by way of preference: methylaminocarbonyl, ethylaminocarbonyl, n-propylamino carbonyl, isopropylaminocarbonyl, n-butylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl.

By way of example and by way of preference, alkoxycarbonyl represents methoxycarbonyl, ethoxycarbonyl, n-propoxycarbonyl, isopropoxycarbonyl, tert-butoxycarbonyl, n-pentoxycarbonyl and n-hexoxycarbonyl.

By way of example and by way of preference, alkoxycarbonylamino represents methoxycarbonylamino, ethoxycarbonylamino, n-propoxycarbonylamino, isopropoxycarbonylamino, tert-butoxycarbonylamino, n-pentoxycarbonylamino and n-hexoxycarbonylamino.

By way of example and by way of preference, alkanoylamino represents acetylamino and ethylcarbonylamino.

Cycloalkyl represents a cycloalkyl group having generally 3 to 8, preferably 5 to 7, carbon atoms, by way of example and by way of preference cyclopropyl, cyclobutyl, cyclopentyl, cyclohexyl and cycloheptyl.

Aryl per se and in aryloxy represents a mono- to tricyclic aromatic carbocyclic radical having generally 6 to 14 carbon atoms; by way of example and by way of preference phenyl, naphthyl and phenanthrenyl.

By way of example and by way of preference, aryloxy represents phenyloxy and naphthyloxy.

Heteroaryl per se and in heteroaryloxy represents an aromatic mono- or bicyclic radical having generally 5 to 10, preferably 5 to 6, ring atoms and up to 5, preferably up to 4, heteroatoms from the group consisting of S, O and N, by way of example and by way of preference thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

By way of example and by way of preference, heteroaryloxy represents pyridyloxy, pyrimidyloxy, indolyloxy, indazolyloxy.

Heterocyclyl and heterocycle represent a mono- or polycyclic, preferably mono- or bicyclic, non-aromatic heterocyclic radical having 4 to 10, generally 5 to 8, preferably 5 or 6, ring atoms and up to 3, preferably up to 2, heteroatoms and/or hetero groups from the group consisting of N, O, S, SO, $SO_2$. The heterocyclyl radicals may be saturated or partially unsaturated. Preference is given to 5- or 6-membered monocyclic saturated heterocyclyl radicals having up to two heteroatoms from the group consisting of O, N and S, such as, by way of example and by way of preference, tetrahydrofuran-2-yl, tetrahydrothienyl, pyrrolidin-2-yl, pyrrolidin-3-yl, pyrrolinyl, pyranyl, piperidin-1-yl, piperidin-2-yl, piperidin-3-yl, piperidin-4-yl, thiopyranyl, morpholin-1-yl, morpholin-2-yl, morpholin-3-yl, perhydroazepinyl, piperazin-1-yl, piperazin-2-yl.

Halogen represents fluorine, chlorine, bromine and iodine.

If radicals in the compounds according to the invention are substituted, the radicals can be mono- or polysubstituted by identical or different substituents unless otherwise specified. A substitution by up to three identical or different substituents is preferred. Very particular preference is given to substitution with one substituent.

Preference is given to compounds of the formula (I) in which

═══represents a double bond,

X represents —$NR^6$—, —$CH_2$— or —C(═O)—, in which $R^6$ represents hydrogen or methyl, $R^1$ represents hydrogen, fluorine, chlorine, cyano, trifluoromethyl, difluoromethyl, methyl, ethyl, hydroxyethyl, methoxyethyl, cyclopropyl, ($C_1$-$C_6$)-alkoxycarbonyl or ($C_1$-$C_6$)-alkylaminocarbonyl, where alkoxycarbonyl and alkylaminocarbonyl for their part may be substituted by hydroxyl, hydroxycarbonyl, ($C_1$-$C_6$)-alkoxy, ($C_1$-$C_6$)-alkoxycarbonyl, amino, aminocarbonyl, ($C_1$-$C_6$)-alkylamino or ($C_1$-$C_6$)-alkylaminocarbonyl, $R^2$ represents fluorine or chlorine, $R^3$ represents a radical selected from the group consisting of:

hydrogen, hydroxyl, halogen, trifluoromethyl, pentafluoroethyl, ($C_1$-$C_6$)-alkyl, ($C_1$-$C_6$)-alkoxy, ($C_3$-$C_8$)-cycloalkyl, where alkyl, alkoxy and cycloalkyl for their part may be substituted by hydroxyl, hydroxycarbonyl, ($C_1$-$C_6$)-alkoxy, ($C_1$-$C_6$)-alkoxycarbonyl, ($C_6$-$C_{10}$)-aryl, —$NR^9R^{10}$ or —C(═O)$NR^9R^{10}$, in which $R^9$ and $R^{10}$ independently of one another represent hydrogen or ($C_1$-$C_8$)-alkyl or $R^9$ and $R^{10}$ together with the nitrogen atom to which they are attached form a 5- or 6-membered heterocycle which may contain a further heteroatom O or N in the ring and which may substituted by $(C_1-C_6)$-alkyl, $(C_1-C_6)$-alkanoyl or $(C_1-C_6)$-alkoxycarbonyl, phenyl, 5- or 6-membered heteroaryl, 5- to 10-membered heterocyclyl which is attached via a carbon atom, where phenyl, heteroaryl and heterocyclyl for their part may be substituted by halogen, cyano, nitro, hydroxycarbonyl, amino, trifluoromethyl, optionally hydroxyl-substituted $(C_1-C_6)$-alkyl, $(C_1-C_6)$-alkoxy, $(C_1-C_6)$-alkylamino, $(C_1-C_6)$-alkanoyl, $(C_1-C_6)$-alkoxycarbonyl, $(C_1-C_6)$-alkanoylamino or $(C_1-C_6)$-alkoxycarbonylamino,

—$NR^{11}R^{12}$, in which $R^{11}$ and $R^{12}$ independently of one another represent hydrogen, $(C_1-C_6)$-alkyl, $(C_3-C_8)$-cycloalkyl, $(C_6-C_{10})$-aryl or 5- to 10-membered heteroaryl, where alkyl and cycloalkyl for their part may be substituted by hydroxyl, $(C_1-C_6)$-alkoxy, $(C_6-C_{10})$-aryl or 5- to 10-membered heteroaryl, and where aryl and heteroaryl for their part may be substituted by halogen, hydroxyl, amino, cyano, trifluoromethyl, $(C_1-C_6)$-alkyl, $(C_1-C_6)$-alkoxy, $(C_1-C_6)$-alkylamino or $(C_1-C_6)$-alkanoylamino, or $R^{11}$ and $R^{12}$ together with the nitrogen atom to which they are attached form a 4- to 6-membered heterocycle which may contain a further heteroatom O or N in the ring and which may be substituted by fluorine, hydroxyl, hydroxycarbonyl, $(C_1-C_4)$-alkoxy, $(C_1-C_4)$-alkyl, $(C_1-C_4)$-alkanoyl or $(C_1-C_4)$-alkoxycarbonyl, and —$C(=O)R^{19}$, in which $R^{19}$ represents $(C_1-C_6)$-alkoxy, $(C_1-C_6)$-alkylamino or a 5- to 10-membered mono- or bicyclic heterocycle which is attached via a nitrogen atom, which is fused or spirocyclic and which may have one or two further heteroatoms from the group consisting of N and O in the ring, where alkylamino for its part may be substituted by a 5- or 6-membered heterocycle, c $R^4$ represents hydrogen, fluorine or chlorine, $R^5$ represents hydrogen or methyl, and their salts, hydrates, hydrates of the salts and solvates.

Particular preference is given to compounds of the formula (I) in which

═ represents a double bond,

X represents —$NR^6$—, —$CH_2$— or —$C(=O)$—, in which $R^6$ represents hydrogen or methyl, $R^1$ represents hydrogen, fluorine, chlorine, cyano, trifluoromethyl, difluoromethyl, methyl, ethyl, hydroxyethyl, methoxyethyl or cyclopropyl, $R^2$ represents fluorine or chlorine, $R^3$ represents a radical selected from the group consisting of:

hydrogen, hydroxyl, halogen, trifluoromethyl, pentafluoroethyl, $(C_1-C_6)$-alkyl, $(C_1-C_6)$-alkoxy, $(C_3-C_8)$-cycloalkyl, where alkyl, alkoxy and cycloalkyl for their part may be substituted by hydroxyl, $(C_1-C_6)$-alkoxy or —$NR^9R^{10}$, in which $R^9$ and $R^{10}$ independently of one another represent hydrogen or $(C_1-C_8)$-alkyl or $R^9$ and $R^{10}$ together with the nitrogen atom to which they are attached form a 5- or 6-membered heterocycle which may contain a further heteroatom O or N in the ring and which may be substituted by $(C_1-C_3)$-alkyl or $(C_1-C_3)$-alkanoyl, phenyl and 5- or 6-membered heteroaryl, where phenyl and heteroaryl for their part may be substituted by halogen, amino or trifluoromethyl, $R^4$ represents hydrogen, fluorine or chlorine, $R^5$ represents hydrogen or methyl, and their salts, hydrates, hydrates of the salts and solvates.

Very particular preference is given to the compounds of the formula (I) in which ═ represents a double bond, X represents —NH— or —$CH_2$—, $R^1$ represents hydrogen, chlorine or methyl, $R^2$ represents fluorine, $R^3$ represents a radical selected from the group consisting of hydrogen, halogen, trifluoromethyl, optionally halogen-substituted phenyl and pyridine, $R^4$ represents hydrogen or fluorine, $R^5$ represents hydrogen, and their salts, hydrates, hydrates of the salts and solvates.

Preference is also given to compounds of the formula (I) in which $R^1$ represents hydrogen, fluorine, chlorine, cyano, trifluoromethyl, difluoromethyl or methyl.

Preference is also given to compounds of the formula (I) in which $R^2$ represents fluorine.

Preference is also given to compounds of the formula (I) in which $R^3$ represents a radical selected from the group consisting of: hydrogen, chlorine, trifluoromethyl, para-fluorophenyl and pyridine.

Preference is also given to compounds of the formula (I) in which $R^4$ represents hydrogen or fluorine.

Preference is also given to compounds of the formula (I) in which $R^5$ represents hydrogen.

The present invention furthermore provides a process for preparing the compounds of the formula (I), characterized in that compounds of the formula (II)

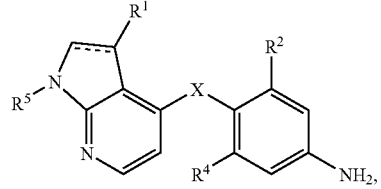

in which

═ X, $R^1$, $R^2$, $R^4$ and $R^5$ are as defined above are reacted with compounds of the formula (III)

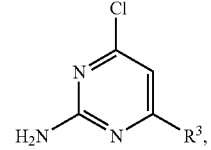

in which

R³ is as defined above, which, if X represents a CH₂ group, may be followed by an oxidation to give the corresponding keto group —C(=O)— or a methylation to give the corresponding mono- or dimethyl compound [—CH(CH₃)— or —(CH₃)₂—].

The reaction is generally carried out in aqueous hydrochloric acid solution, preferably in a temperature range of from 70° C. to 110° C. at atmospheric pressure.

If X represents a CH₂ group, any optional oxidation or alkylation can be carried out according to customary methods known to the person skilled in the art.

To prepare compounds of the formula (II), for example, compounds of the formula (IV)

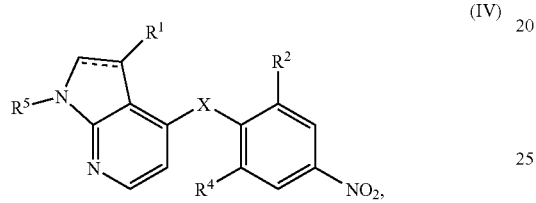
(IV)

in which $\text{-----}$ X, R¹, R² and R⁴ are as defined above and

R⁵ is as defined above or represents a [2-(trimethylsilyl)ethoxy]methyl protective group are reacted with reducing agents.

The reaction is generally carried out in inert solvents, preferably in a temperature range of from room temperature to reflux of the solvents, at from atmospheric pressure to 3 bar.

Reducing agents are, for example, palladium-on-carbon and hydrogen, platinum oxide and hydrogen, tin dichloride or titanium trichloride; preference is given to palladium-on-carbon and hydrogen or platinum oxide and hydrogen.

Inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, alcohols, such as methanol, ethanol, n-propanol, isopropanol, n-butanol, tert-butanol or 2-ethylhexanol, hydrocarbons, such as benzene, xylene, toluene, hexane, cyclohexane or mineral oil fractions, or other solvents, such as dimethylformamide, dimethylacetamide, acetonitrile, pyridine or acetic acid; preferred solvents are ethanol, n-butanol or 2-ethylhexanol.

The 6-position of the pyrrolopyridine in compounds of the formula (IV) may optionally be substituted by chlorine. This chlorine substituent is removed during the reduction.

If R⁵ in the target compound represents hydrogen, the nitrogen atom to which R⁵ is attached may optionally be protected during this synthesis with a [2-(trimethylsilyl)ethoxy]methyl protective group.

The protective group is removed after the reduction of the nitro group using trifluoroacetic acid in dichloromethane in a temperature range of from room temperature to 40° C., at atmospheric pressure. If appropriate, this is followed by a reaction with a base, such as, for example, sodium hydroxide, potassium hydroxide or lithium hydroxide in THF, in a temperature range of from room temperature to 40° C., at atmospheric pressure, for complete removal of the protective group.

To prepare compounds of the formula (IV), for example, according to process [A] compounds of the formula (V)

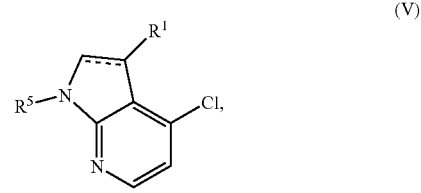
(V)

in which $\text{-----}$ and R¹ are as defined above, and

R⁵ is as defined above or represents a [2-trimethylsilyl)ethoxy]methyl protective group are reacted with compounds of the formula (VI)

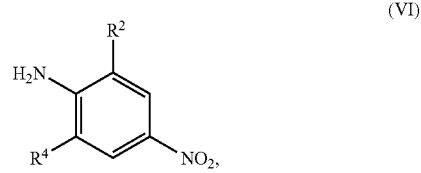
(VI)

in which

R² and R⁴ are as defined above, to give compounds of the formula (IVa)

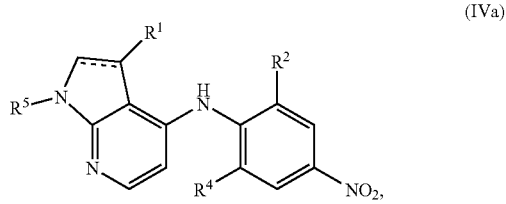
(IVa)

in which $\text{-----}$ R¹, R² and R⁴ are as defined above, and

R⁵ is as defined above or represents a [2-(trimethylsilyl)ethoxy]methyl protective group, or according to process [B] compounds of the formula (VII)

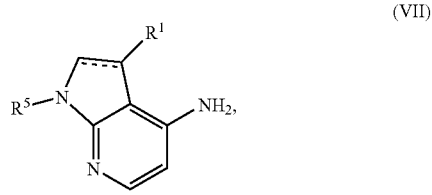
(VII)

in which

━and $R^1$ are as defined above, and $R^5$ is as defined above or represents a [2-trimethylsilyl) ethoxy]methyl protective group, are reacted with compounds of the formula (VIII)

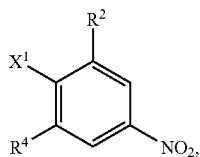

(VIII)

in which $R^2$ and $R^4$ are as defined above, and $X^1$ represents halogen, preferably iodine, chlorine or bromine, to give compounds of the formula (IVa), or according to process [C] compounds of the formula (IX)

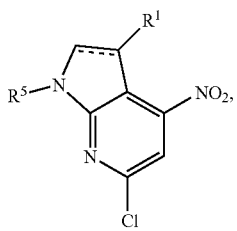

(IX)

in which

━and $R^1$ are as defined above, and $R^5$ is as defined above or represents a [2-(trimethylsilyl) ethoxy]methyl protective group, are reacted with compounds of the formula (X)

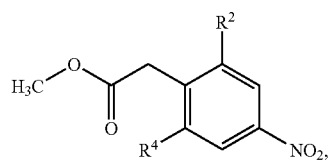

(X)

in which $R^2$ and $R^4$ are as defined above, followed by a decarboxylation of the ester to give compounds of the formula (IVb)

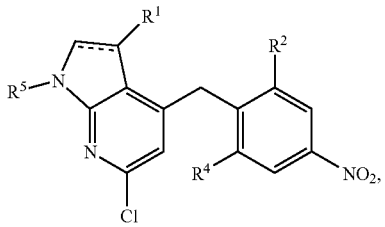

(IVb)

in which

━ $R^1$, $R^2$ and $R^4$ are as defined above, and $R^5$ is as defined above or represents a [2-(trimethylsilyl) ethoxy]methyl protective group.

The compound (IVa) obtained according to process variant [A] or [B] may, if appropriate, be subjected to an alkylation at the bridged nitrogen atom according to customary methods known to the person skilled in the art. This yields compounds where X=N-alkyl.

The compound (IVb) obtained according to process variant [C] may, if appropriate, be subjected to an oxidation or alkylation at the bridging methylene group, to give the corresponding keto group and the corresponding mono- or dimethyl compound, respectively, in each case according to customary methods known to the person skilled in the art. This gives compounds where X=—C(=O)—, —CH(CH$_3$)— or —C(CH$_3$)$_2$—.

The compounds of the formulae (IVa) and (IVb) represent a fraction of the compounds of the formula (IV).

The compounds according to processes [A] and [B] are preferably carried out by the Buchwald process using a palladium compound, such as, for example, tris(dibenzylideneacetone)dipalladium, a phosphine, such as, for example, dicyclohexyl(2',4',6'-triisopropylbiphenyl-2-yl)phosphine or 1,1'-bis(diphenylphosphino)ferrocene, and a base, such as, for example, sodium tert-butoxide or potassium tert-butoxide or sodium carbonate or potassium carbonate, in an inert solvent, such as, for example, tert-butanol or toluene, in a temperature range of from 90° C. to 140° C., at atmospheric pressure or slightly elevated pressure.

The reaction according to process [C] is preferably carried out in an inert solvent, such as, for example, N,N-dimethylformamide, N-methylpyrrolidone, dimethyl sulfoxide or nitrobenzene, in the presence of a base, such as, for example, potassium carbonate, potassium hydroxide, potassium tert-butoxide or sodium hydride, at a temperature of from 120° C. to 280° C., at atmospheric pressure.

The decarboxylation in process [C] is carried out by reaction with a base, such as, for example, potassium hydroxide, sodium hydroxide or lithium hydroxide, in an inert solvent, such as, for example, methanol or ethanol, at a temperature of from room temperature to 40° C., at atmospheric pressure.

The compounds of the formulae (III), (V), (VI), (VII), (VIII), (IX) and (X) are known per se to the person skilled in the art or can be prepared by customary processes known from the literature.

The preparation of the compounds according to the invention can be illustrated by the synthesis schemes below.
Scheme 1:
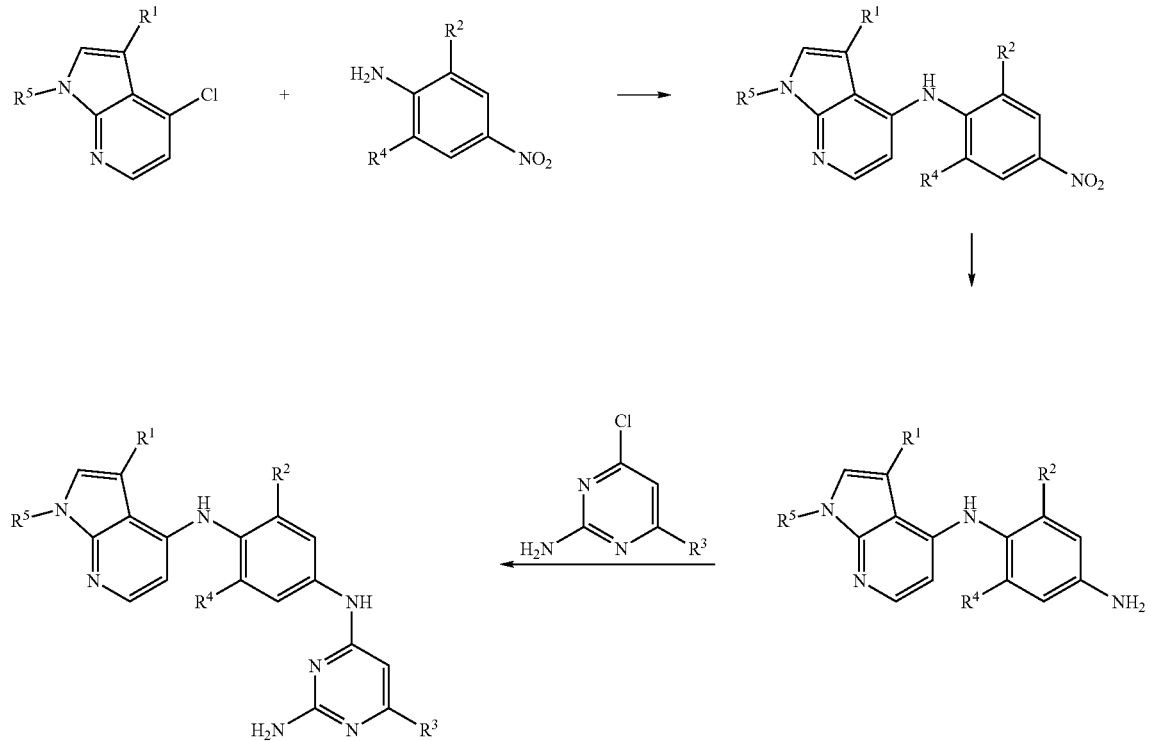
Scheme 2:
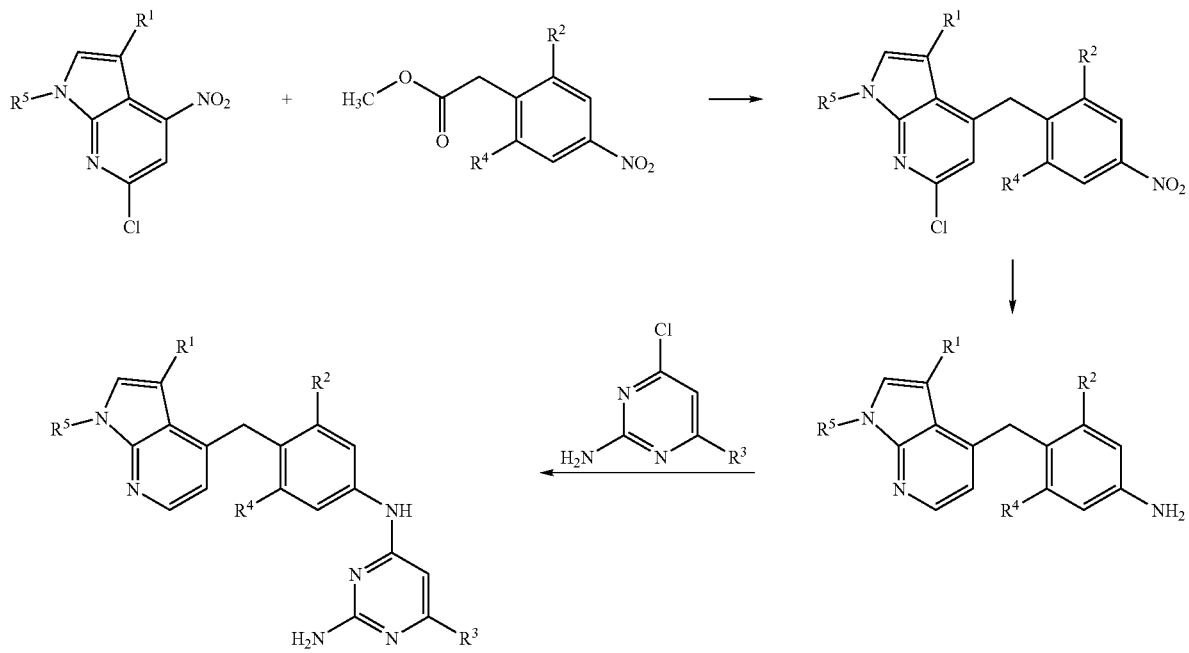

The compounds according to the invention have an unforeseeable useful spectrum of pharmacological and pharmacokinetic actions.

Accordingly, they are suitable for use as pharmaceuticals for the treatment and/or prophylaxis of diseases in humans and animals.

The pharmaceutical activity of the compounds according to the invention can be explained by their action as Rho kinase inhibitors.

The present invention also provides the use of the compounds according to the invention for the treatment of and/or prophylaxis of disorders, preferably cardiovascular disorders.

The compounds according to the invention are suitable for the prophylaxis and/or treatment of cardiovascular disorders such as, for example, hypertension and cardiac insufficiency, stable and unstable angina pectoris, disorders of peripheral and cardiac vessels, of arrhythmias, of thrombolic disorders and ischemias, such as myocardial infarction, stroke, transitory and ischemic attacks, obstruction of peripheral circulation, subarachnoidal hemorrhages, prevention of restenoses, such as, for example, after thrombolysis therapies, percutaneous transluminal angioplasties (PITA) percutaneous transluminal coronary angioplasties (PTCA), bypass, and for the prophylaxis and/or treatment of arteriosclerosis, Alzheimer's disease, kidney failure, glaucoma, asthmatic disorders, COPD and diseases of the urogenital system, such as, for example, prostate hypertrophy, erectile dysfunction, female sexual dysfunction, osteoporosis, gastroparesis and incontinence.

The compounds according to the invention can furthermore be used for the prophylaxis and/or treatment of cancers, in particular of tumors.

In the context of the present invention, the definition of tumors includes both benign and malignant tumors and thus, for example, also benign neoplasias, dysplasias, hyperplasias, and neoplasias with metastasis formation. Further examples of tumors are carcinomas, sarcomas, carcinosarcomas, tumors of the hemopoietic organs, tumors of the nervous tissue, for example of the brain, or tumors of skin cells. In tumor formation, uncontrolled or inadequately controlled cell division occurs. The tumor can be locally restricted, but it can also infiltrate the surrounding tissue and then get lodged by the lymphatic system or by the bloodstream in a new location. There are thus primary and secondary tumors. Primary tumors are originally formed in the organ in which they are found. Secondary tumors have been lodged in another organ by metastasis formation and then spread in their new location.

The present invention also provides the use of the compounds according to the invention for the prophylaxis and/or treatment of disorders, in particular the syndromes mentioned above.

The present invention also provides the use of the compounds according to the invention for preparing a medicament for the prophylaxis and/or treatment of disorders, in particular the syndromes mentioned above.

The present invention also provides a method for the prophylaxis and/or treatment of disorders, in particular the disorders mentioned above, using a cardiovascularly effective amount of the compound according to the invention.

The present invention also provides medicaments, comprising a compound according to the invention in combination with one or more further active compounds, in particular for the prophylaxis and/or treatment of the disorders mentioned above.

The compound according to the invention can act systemically and/or locally. For this purpose, it can be administered in a suitable manner, such as, for example, orally, parenterally, pulmonarily, nasally, sublingually, lingually, buccally, rectally, transdermally, conjunctivally, otically, as stents or as an implant.

For these administration routes, the compound according to the invention can be administered in suitable administration forms.

Suitable for oral administration are administration forms working according to the prior art, which release the compounds according to the invention rapidly and/or in modified form and which contain the compounds according to the invention in crystalline and/or amorphized and/or dissolved form, such as, for example, tablets (non-coated or coated tablets, for example coated with enteric, slowly dissolving or insoluble coats which control the release of the compounds according to the invention), tablets which decompose rapidly in the oral cavity or films/wafers, capsules, sugar-coated tablets, granules, pellets, powders, emulsions, suspensions, aerosols or solutions.

Parenteral administration can take place with circumvention of an absorption step (intravenous, intraarterial, intracardiac, intraspinal or intralumbar) or with involvement of an absorption (intramuscular, subcutaneous, intracutaneous, percutaneous or intraperitoneal). For parenteral administration, suitable administration forms are, inter alia, injection and infusion preparations in the form of solutions, suspensions, emulsions, lyophilisates and sterile powders.

Suitable for the other administration routes are, for example, pharmaceutical forms for inhalation (inter alia powder inhalers, nebulizers), nasal drops/solutions, sprays; tablets or capsules to be applied lingually, sublingually or buccally, suppositories, ear and eye preparations, vaginal capsules, aqueous suspensions (lotions, shake lotions), lipophilic suspensions, ointments, creams, milk, pastes, dusting powder, stents, or implants.

The compounds according to the invention can be converted into the administration forms mentioned in a manner known per se. This takes place using inert nontoxic, pharmaceutically acceptable auxiliaries. These include, inter alia, carriers (for example microcrystalline cellulose), solvents (for example liquid polyethylene glycols), emulsifiers (for example sodium dodecylsulfate), dispersants (for example polyvinylpyrrolidone), synthetic and natural biopolymers (for example albumin), stabilizers (for example antioxidants, such as ascorbic acid), colorants (for example inorganic pigments, such as iron oxides) or taste and/or odor corrigents.

The present invention also provides medicaments comprising at least one compound according to the invention, preferably together with one or more inert nontoxic, pharmaceutically acceptable auxiliaries, and their use for the purposes mentioned above.

In general, it has been found to be advantageous both in human and in veterinary medicine to administer the compound according to the invention in total amounts of from about 0.01 to about 700, preferably 0.01 to 100, mg/kg of body weight per 24 hours, if appropriate in the form of a plurality of individual doses, to obtain the desired results. An individual dose contains the compound according to the invention preferably in amounts of from about 0.1 to about 80, in particular 0.1 to 30, mg/kg of body weight.

In spite of this, it may be necessary, if appropriate, to deviate from the amounts mentioned, namely depending on the body weight, the route of administration, the individual response to the active compound, the type of preparation and the time or interval at which administration takes place. Thus, in some cases it may be sufficient to use less than the above-mentioned minimum amount, whereas in other cases the upper limit mentioned has to be exceeded. In the case of the administration of relatively large amounts, it may be advisable to divide these into several individual administrations over the course of the day.

The percentages in the tests and examples below are, unless indicated otherwise, percentages by weight; parts are parts by weight. Solvent ratios, dilution ratios and concentrations of liquid/liquid solutions are in each case based on the volume.

A. EXAMPLES

| Abbreviations: | |
|---|---|
| TLC | thin-layer chromatography |
| DCI | direct chemical ionization (in MS) |
| DCM | dichloromethane |
| DIEA | N,N-diisopropylethylamine |
| DMA | dimethylacetamide |
| DMF | N,N-dimethylformamide |
| DMSO | dimethyl sulfoxide |
| EA | ethyl acetate |
| EI | electron impact ionization (in MS) |
| ESI | electrospray ionization (in MS) |
| m.p. | melting point |
| sat. | saturated |
| h | hour |
| HATU | O-(7-azabenzotriazol-1-yl)-N,N,N',N'-tetramethyluronium hexafluorophosphate |
| HOAT | 3H-[1,2,3]-triazol[4,5-b]pyridin-3-ole |
| HOBt | 1-hydroxy-1H-benzotriazole × $H_2O$ |
| HPLC | high pressure, high performance liquid chromatography |
| conc. | concentrated |
| LC-MS | liquid chromatography-coupled mass spectroscopy |
| LDA | lithium diisopropylamide |
| min | minutes |
| MPLC | medium pressure, medium performance liquid chromatography |
| MS | mass spectroscopy |
| NMR | nuclear magnetic resonance spectroscopy |
| org. | organic |
| RF | reflux |
| $R_f$ | retention factor (in TLC) |
| RP-HPLC | reverse phase HPLC |
| RT | room temperature |
| $R_t$ | retention time (in HPLC) |
| TFA | trifluoroacetic acid |
| THF | tetrahydrofuran |

HPLC, LCMS and GCMS Methods:

Method 1 (LC/MS): MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2 (LC/MS): Instrument: Micromass Quattro LCZ with HPLC Agilent Series 1100; column: Phenomenex Synergi 2μ Hydro-RP Mercury 20 mm×4 mm; mobile phase A: 111 of water+0.5 ml of 50% strength formic acid, mobile phase B: 111 of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 mini/4.5 min 2 ml/min; oven: 50° C.; UV detection: 208-400 nm.

Method 3 (LC/MS): MS instrument type: Micromass ZQ; HPLC instrument type: HP 1100 Series; WV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4 (HPLC): Instrument: HP 1100 with DAD detection; column: Kromasil 100 RP-18, 60 mm×2.1 mm, 3.5 μm; mobile phase A: 5 ml of perchloric acid (70% strength)/l of water, mobile phase B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; oven: 30° C.; UV detection: 210 nm.

Method 5 (LC-MS): Instrument: Micromass Platform LCZ with HPLC Agilent Series 1100; column: Thermo HyPURITY Aquastar 3μ 50 mm×2.1 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC/MS): Instrument: Micromass Platform LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 7 (LC/MS): MS instrument type: Micromass ZQ; HPLC instrument type: Waters Alliance 2790; column: Grom-Sil 120 ODS-4 HE 50 mm×2 mm, 3.0 μm; mobile phase B: acetonitrile+0.05% formic acid, mobile phase A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 8 (LCMS): Instrument: Micromass Quattro LCZ, with HPLC Agilent Series 1100; column: Grom-SIL 120 ODS-4 HE, 50 mm×2.0 mm, 3 μm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 9 (LCMS): MS instrument type: Micromass ZQ; HPLC instrument type: Waters Alliance 2795; column: Merck Chromolith SpeedROD RP-18e 50 mm×4.6 mm; mobile phase A: water+500 μl of 50% strength formic acid/l; mobile phase B: acetonitrile+500 μl of 50% strength formic acid/l; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 10 (LCMS): Instrument: Micromass Platform LCZ with HPLC Agilent Series 1100; column: Grom-SIL 120 ODS-4 HE, 50 mm×2.0 mm, 3 μm; mobile phase A: 1 l of water+1 ml of 50% strength formic acid, mobile phase B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Preparative HPLC: Column: YMC Gel ODS-AQ S-5/15 μM, 250 mm×30 mm, mobile phase A: water; mobile phase B: acetonitrile; gradient: 0.00 min 30% B→3.00 min 30%

B→34.0 min 95% B→38.0 min 30% B; temp.: room temperature; flow rate: 50 ml/min; UV detection.

Starting Materials

Example 1A

1H-Pyrrolo[2,3-b]pyridine 7-oxide

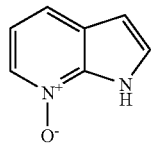

(Antonini, Ippolito; Claudi, Francesco; Cristalli, Gloria; Franchetti, Palmarisa; Grifantini, Mario; Martelli, Sante; J. Med. Chem. 1982, 25, 1258-1261.) 540 g (2.35 mol) of 3-chloroperbenzoic acid are dissolved in 6.11 l of dichloromethane, and the water that separates off is removed. The organic phase is dried over sodium sulfate and cooled to 0° C. A solution of 163 g (1.38 mol) of 1H-pyrrolo[2,3-b]pyridine (Hands, D.; Bishop, B.; Cameron, M.; Edwards, T. S.; Cottrell, I. F.; Wright, S. H. B.; Synthesis 1996, 877-882.) in 1.00 l of dichloromethane is then added, and the temperature is allowed to rise to room temperature. After 2 hours, methanol is added in such an amount that the precipitate formed redissolves. The mixture is filtered through silica gel (mobile phase:dichloromethane/methanol 95:5) and the product fractions are, after concentration, dried under high vacuum.

Yield: 145 g (75% of theory)
HPLC (Method 4): $R_t$=2.02 min.
MS (ESI pos.): m/z=135 [M+H]$^+$, 152 [M+NH$_4$]$^+$, 269 [2M+H]$^+$.
$^1$H-NMR (DMSO-d$_6$, 200 MHz): δ=6.58 (d, 1H), 7.07 (dd, 1H), 7.48 (d, 1H), 7.65 (d, 1H), 8.17 (d, 1H), 12.42-12.64 (br. s, 1H).

Example 2A

4-Nitro-1H-pyrrolo[2,3-b]pyridine 7-oxide

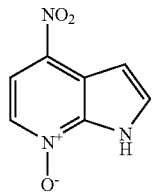

Based on the results of the differential thermal analysis, it is not recommended to carry out the reaction in batches larger than five times the amount described.

A solution of 20.0 g (149 mmol) of 1H-pyrrolo[2,3-b]pyridine 7-oxide in 160 ml of trifluoroacetic acid is cooled to room temperature. 69.3 ml of 65% strength nitric acid are then slowly added dropwise, and the mixture is allowed to stir at room temperature for 2 h. The mixture is put onto ice, and the pH is adjusted to 8-9 using 45% strength sodium hydroxide solution. The precipitate is filtered off with suction and washed with water. The cooled products of four batches of the size described and a 13 g batch carried out analogously are combined and purified together. The crude products are suspended in water and the pH is adjusted to 8-9 using 2N sodium hydroxide solution. After 10 min of stirring, the precipitate is filtered off with suction and dried under high vacuum. (Schneller, Stewart W.; Luo, Jiann-Kuan; J. Org. Chem. 1980, 45, 4045-4048.)

Yield: 29.7 g (24% of theory)
HPLC (Method 4): $R_t$=3.02 min.
MS (ESI pos.): m/z=180 (M+H)$^+$, 197 (M+NH4)$^+$, 359 (2M+H)$^+$.
$^1$H-NMR (DMSO-d$_6$, 200 MHz): δ=7.03 (d, 1H), 7.80 (d, 1H), 8.03 (d, 1H), 8.31 (d, 1H), 13.22-13.41 (br. s, 1H).

Example 3A

6-Chloro-4-nitro-1H-pyrrolo[2,3-b]pyridine

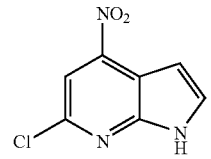

Under an argon atmosphere, 5.00 g (27.9 mmol) of 4-Nitro-1H-pyrrolo[2,3-b]pyridine 7-oxide and 11.8 ml (55.8 mmol) of hexamethyldisilazane are initially charged in 290 ml of THF. At RT, 10.8 ml (140 mmol) of methyl chloroformate are added. The solution is stirred at RT overnight. The reaction solution is filtered through a silica gel cartridge and the cartridge is washed with dichloromethane/methanol 10:1.

Yield: 2.8 g (70% of theory)
LC-MS (Method 3): $R_t$=2.15 min.
MS (ESI pos.): m/z=198 (M+H)$^+$.
$^1$H-NMR (DMSO-d$_6$, 200 MHz): δ=7.00 (m, 1H), 7.97 (s, 1H), 8.00 (t, 1H), 12.79 (s, 1H).

Example 4A

6-Chloro-4-nitro-1-{[2-(trimethylsilyl)ethoxy]methyl}-1H-pyrrolo[2,3-b]pyridine

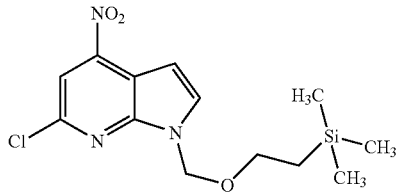

At 0° C. and under an atmosphere of argon, 1.34 g (28.3 mmol) of sodium hydride (60% in mineral oil) are added in small portions to a solution of 5.6 g (28.3 mmol) of 6-chloro-4-nitro-1H-pyrrolo[2,3-b]pyridine in dimethylformamide (50 ml), and the suspension is stirred at RT for 30 minutes. The mixture is once more cooled to 0° C., 5.3 ml (29.8 mmol of 2-(trimethylsilyl)ethoxymethyl chloride are added dropwise and the mixture is allowed to stir at room temperature for 2 h. The suspension is poured into ice-water (250 ml) and stirred until the mixture has reached RT. The mixture is then extracted with ethyl acetate (three times 50 ml) and the organic phase is washed with saturated sodium chloride solution. The solution is dried over magnesium sulfate and concentrated. The residue is purified by column chromatography on silica gel (mobile phase: cyclohexane/ethyl acetate 6:1).

Yield: 6.88 g (74% of theory)

$^1$H-NMR (DMSO-d$_6$, 300 MHz): δ=−0.09 (s, 9H), 0.83 (t, 2H), 3.54 (t, 2H), 5.67 (s, 2H), 7.06 (d, 1H), 8.02 (s, 1H), 8.12 (d, 1H).

Example 5A

4-Nitro-1-{[2-trimethylsilyl)ethoxy]methyl}-1H-pyrrolo[2,3-b]pyridine

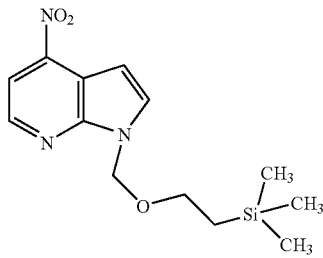

240 mg (6.01 mmol) of sodium hydride are added to a solution of 980 mg (6.01 mmol) of 4-nitro-1H-pyrrolo[2,3-b]pyridine (Antonini, Ippolito; Claudi, Francesco; Cristalli, Gloria; Franchetti, Palmarisa; Grifantini, Mario; Martelli, Sante; J. Med. Chem. 1982, 25, 1258-1261.) in DMF (10 ml). The mixture is stirred at RT for 30 min, and 1.05 g (6.31 mmol) of (trimethylsilyl)ethoxymethyl chloride are then added and the reaction mixture is stirred at RT for 1 h. After concentration under reduced pressure, the residue is purified by column chromatography on silica gel (mobile phase: cyclohexane/ethyl acetate 10:1). The target product is obtained by concentration.

Yield: 1.22 g (69% of theory)

LC-MS (Method 7): R$_t$=4.15 min.

MS (ESI pos.): m/z=294 (M+H)$^+$.

$^1$H-NMR (DMSO-d$_6$, 300 MHz): δ=−0.09 (s, 9H), 0.93 (t, 2H), 3.63 (t, 2H), 5.84 (s, 2H), 7.18 (d, 1H), 8.08 (d, 1H), 8.22 (d, 1H), 8.68 (d, 1H).

Example 6A

1-{[2-(Trimethylsilyl)ethoxy]methyl}-1H-pyrrolo[2,3-b]pyridine-4-amine

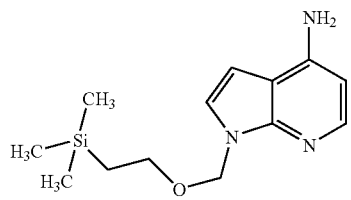

1.30 g (3.97 mmol) of 6-chloro-4-nitro-1-{[trimethylsilyl)ethoxy]methyl}-1H-pyrrolo[2,3-b]pyridine are dissolved in 10 ml of ethanol/TH (1:1). 90 mg (0.4 mmol) of platinum(IV) oxide are added, and the mixture is hydrogenated in a hydrogen atmosphere under atmospheric pressure overnight. The same amount of catalyst is then added once more, and the mixture is hydrogenated for another night. The mixture is filtered through Celite, and the Celite is washed with ethanol. The solvent is removed, the residue is taken up in ethanol (10 ml) and 0.55 ml (3.97 mmol) of triethylamine is added. 422 mg (0.40 mmol) of 10% palladium-on-carbon is added and the mixture is reduced at a hydrogen pressure of 3.5 bar overnight. The mixture is filtered through Celite, the Celite is washed with ethanol and the solvent is removed under reduced pressure. The product is purified by column chromatography on silica gel (mobile phase: dichloromethane/acetone 20:1 to 10:1). The product obtained is triturated with pentane and filtered off with suction.

Yield: 548 mg (46% of theory)

Alternative Preparation Process:

A mixture of 900 mg (3.07 mmol) of 4-nitro-1-{[2-(trimethylsilyl)ethoxy]methyl}-1H-pyrrolo[2,3-b]pyridine and platinum(IV) oxide in 30 ml of ethanol/THF (1:1) is stirred in an atmosphere of hydrogen at atmospheric pressure overnight. The suspension is then filtered through Celite and the Celite is washed with ethanol. The target product is obtained by concentration of the filtrate.

Yield: 760 mg (94% of theory)

LC-MS (Method 3): R$_t$=1.49 min.

MS (ESI pos.): m/z=264 [M+H]$^+$.

$^1$H-NMR (DMSO-d$_6$, 300 MHz): δ=−0.10 (s, 9H), 0.80 (t, 2H), 3.47 (t, 2H), 5.47 (s, 2H), 6.15 (br. s, 2H), 6.18 (d, 1H), 6.55 (d, 1H), 7.17 (d, 1H), 7.75 (d, 1H).

Example 7A

N-(2-Fluoro-4-nitrophenyl)-1-{[2-(trimethylsilyl)ethoxy]methyl}-1H-pyrrolo[2,3-b]pyridine-4-amine

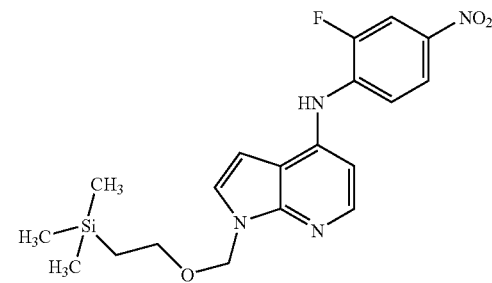

50 mg (0.19 mmol) of 1-{[2-(trimethylsilyl)ethoxy]methyl}-1H-pyrrolo[2,3-b]pyridine-4-amine, 61 mg (0.23 mmol) of 2-fluoro-1-iodo-4-nitrobenzene and 26 mg (0.27 mmol) of sodium tert-butoxide are initially charged in 1 ml of toluene. The mixture is degassed. 8.7 mg (0.01 mmol) of tris(dibenzylideneacetone)dipalladium and 9.1 mg (0.02 mmol of dicyclohexyl(2',4',6'-triisopropylbiphenyl-2-yl)phosphine are then added. The mixture is heated in a sealed vessel at 120° C. overnight. The mixture is then filtered through an Extrelut cartridge (mobile phase: dichloromethane/methanol 10:1) and purified by preparative HPLC.

Yield: 38 mg (50% of theory)

LC-MS (Method 3): R$_t$=2.73 min.

MS (ESI pos.): m/z=403 [M+H]$^+$.

$^1$H-NMR (DMSO-d$_6$, 300 MHz): δ=−0.09 (s, 9H), 0.82 (t, 2H), 3.52 (t, 2H), 5.60 (s, 2H), 6.50 (d, 1H), 6.84 (d, 1H), 7.37 (t, 1H), 7.50 (d, 1H), 8.04 (dd, 1H), 8.13 (d, 1H), 8.17 (dd, 1H), 9.33 (s, 1H).

Example 8A

N-(2-Fluoro-4-nitrophenyl)-1H-pyrrolo[2,3-b]pyridine-4-amine

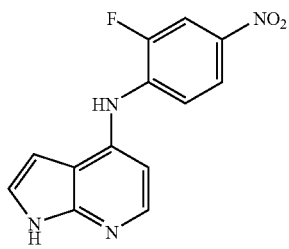

A solution of 500 mg (3.28 mmol) of 4-chloro-1H-pyrrolo[2,3-b]pyridine (Schneller, Stewart, W.; Luo, Jiann-Kuan; J. Org. Chem. 1980, 45, 4045-4048.), 614 mg (3.93 mmol) of 2-fluoro-4-nitroaniline, 150 mg (0.16 mmol) of tris(dibenzylideneacetone)dipalladium and 156 mg (0.33 mmol) of dicyclohexyl(2',4',6'-triisopropylbiphenyl-2-yl)phosphine and 996 mg (7.21 mmol) of potassium carbonate in 5.00 ml of degassed tert-butanol is stirred in a sealed pressure vessel at 100° C. for 3 h. After cooling to RT, the mixture is filtered through Celite, the Celite is washed with ethyl acetate and the filtrates are concentrated under reduced pressure. The residue is purified by column chromatography on silica gel (mobile phase: cyclohexane/ethyl acetate 1:1).

Yield: 694 mg (78% of theory)

Alternative Preparation Method:

250 mg (0.62 mmol) of N-(2-fluoro-4-nitrophenyl)-1-{[2-trimethylsilyl)ethoxy]methyl}-1H-pyrrolo[2,3-b]pyridine-4-amine are dissolved in 2.5 ml of dichloromethane. 2.5 ml of trifluoroacetic acid are added, and the mixture is allowed to stir at RT for 3 hours. The reaction solution is evaporated to dryness. The residue in the flask is taken up in THF, and 6.2 ml (6.2 mmol) of 1 M lithium hydroxide solution are added. The mixture is allowed to stir at RT overnight, another 3.1 ml (3.1 mmol) of 1 M lithium hydroxide solution are added and the mixture is stirred for 4 hours. 1 M citric acid is added to the reaction solution, and the mixture is extracted twice with ethyl acetate. The aqueous phase is made alkaline using aqueous sodium hydroxide solution and extracted twice with ethyl acetate. The combined organic phases are then dried over sodium sulfate. The solvent is removed under reduced pressure. The residue is purified by column chromatography on silica gel (mobile phase: dichloromethane/methanol 50:1 to 5:2).

Yield: 165 mg (98% of theory)

LC-MS (Method 1): $R_t$=1.11 min.

MS (ESI pos.): m/z=273 (M+H)$^+$.

$^1$H-NMR (DMSO-$d_6$, 300 MHz): δ=6.39 (d, 1H), 6.81 (m, 1H), 7.28-7.37 (m, 2H), 8.04 (dd, 1H), 8.10 (d, 1H), 8.18 (dd, 1H), 9.32 (s, 1H), 11.68 (s, 1H).

Example 9A

2-Fluoro-N'-1H-pyrrolo[2,3-b]pyridin-4-yl-1,4-diaminobenzene

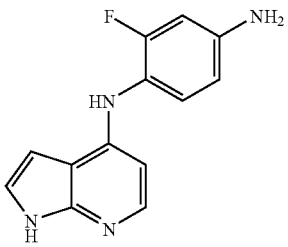

165 mg (0.61 mmol) of N-(2-fluoro-4-nitrophenyl)-1H-pyrrolo[2,3-b]pyridine-4-amine are dissolved in 10 ml of ethanol. 65 mg (0.06 mmol) of 10% palladium-on-carbon are added and the mixture is hydrogenated in a hydrogen atmosphere under atmospheric pressure overnight. The mixture is filtered through Celite and the solvent is removed under reduced pressure.

Yield: 139 mg (95% of theory)

LC-MS (Method 2): $R_t$=1.00 min.

MS (ESI pos.): m/z=243 [M+H]$^+$.

$^1$H-NMR (DMSO-$d_6$, 300 MHz): δ=5.38 (s, 1H), 5.93 (d, 1H), 6.34-6.49 (m, 4H), 6.92-7.02 (m, 1H), 7.08 (d, 1H), 7.73 (d, 1H), 8.0 (s, 1H), 11.15 (s, 1H).

Example 10A

3-Chloro-N-(2-fluoro-4-nitrophenyl)-1H-pyrrolo[2,3-b]pyridine-4-amine

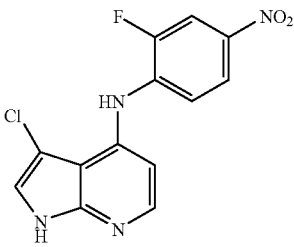

108 mg (810 μmol) of N-chlorosuccinimide are added to a solution of 200 mg (730 μmol) of N-(2-fluoro-4-nitrophenyl)-1H-pyrrolo[2,3-b]pyridine-4-amine in 5 ml of THF, and the mixture is stirred at RT overnight. To bring the reaction to completion, another 49 mg (365 μmol) of N-chlorosuccinimide are added, and the mixture is stirred for another night. Saturated sodium bicarbonate solution is then added to the reaction mixture, and the mixture is extracted with ethyl acetate. The organic phases are washed with saturated sodium chloride solution and then dried with magnesium sulfate, and the solvent is removed under reduced pressure. Purification by column chromatography on silica gel (mobile phase: gradient cyclohexane/ethyl acetate 1:1 to ethyl acetate 100%) and preparative RP-HPLC affords the title compound.

Yield: 125 mg (48% of theory)

LC-MS (Method 1): $R_t$=2.23 min.

MS (ESI pos.): m/z=307 (M+H)$^+$.

¹H-NMR (DMSO-d₆, 300 MHz): δ=6.95 (d, 1H), 7.12 (dd, 1H), 7.58 (s, 1H), 7.98 (d, 1H), 8.16 (d, 1H), 8.22 (d, 1H), 8.97 (s, 1H), 12.08 (s, 1H).

Example 11A

N¹-(3-Chloro-1H-pyrrolo[2,3-b]pyridin-4-yl)-2-fluorobenzene-1,4-diamine

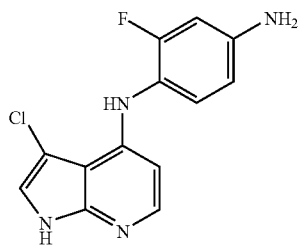

147 mg (650 μmol) of tin(II) chloride dihydrate are added to a solution of 40 mg (130 μmol) of 3-chloro-N-(2-fluoro-4-nitrophenyl)-1H-pyrrolo[2,3-b]pyridine-4-amine in 2.50 ml of DMF, and this solution is stirred at RT overnight. 5 ml of water are then added, and the pH is adjusted to 10 using saturated sodium bicarbonate solution. After filtration through Celite, the Celite is washed with 40 ml of ethyl acetate. The aqueous phase of the filtrate is extracted twice with 10 ml of ethyl acetate. The combined organic phases are washed in each case twice with 5 ml of water and 5 ml of saturated sodium chloride solution and dried with sodium sulfate. Concentration under reduced pressure affords the target compound which is reacted further without purification.

Yield: 29 mg (81% of theory)
LC-MS (Method 1): R$_t$=1.32 min.
MS (ESI pos.): m/z=276 (M+H)⁺.

Example 12A

2-Fluoro-N-(1-{[2-(trimethylsilyl)ethoxy]methyl}-1H-pyrrolo[2,3-b]pyridin-4-yl)benzene-1,4-diamine

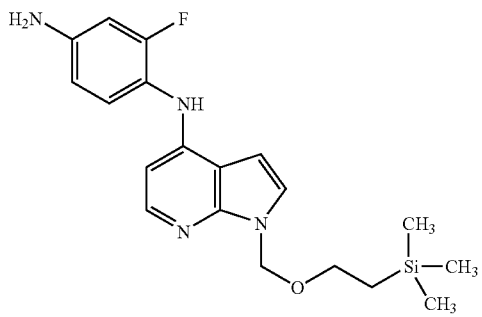

115 mg (0.29 mmol) of N-(2-fluoro-4-nitrophenyl)-1-{[2-(trimethylsilyl)ethoxy]methyl}-1H-pyrrolo[2,3-b]pyridine-4-amine are dissolved in 10 ml of a mixture of ethanol/THF (1:1). 13 mg (0.06 mmol) of platinum(IV) oxide are added, and the mixture is stirred under an atmosphere of hydrogen under atmospheric pressure overnight. The suspension is then filtered through Celite and the solvent is removed under reduced pressure.

Yield: 79 mg (74% of theory)
LC-MS (Method 8): R$_t$=2.26 min.
MS (ESI pos.): m/z=373 (M+H)⁺.
¹H-NMR (DMSO-d₆, 300 MHz): δ=−0.09 (s, 9H), 0.88 (t, 2H), 3.57 (t, 2H), 5.43 (s, 2H), 5.59 (s, 2H), 6.08 (d, 2H), 6.46-6.64 (m, 3H), 7.07 (dd, 1H), 7.31 (d, 1H), 7.88 (d, 1H), 8.12 (s, 1H).

Example 13A

Dimethyl (2-fluoro-4-nitrophenyl)malonate

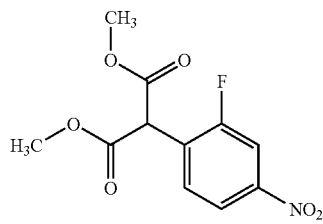

9.13 g (69.1 mmol) of dimethyl malonate are carefully added dropwise to a suspension of 1.66 g (69.1 mmol) of washed sodium hydride in 70 ml of DMSO. The mixture is heated at 100° C. for 40 min and then cooled to RT, and 5.00 g (31.4 mmol) of 3,4-difluoronitrobenzene are added. The mixture is stirred at RT for 30 min and then heated at 100° C. for one hour. The cooled reaction mixture is poured into a mixture of ethyl acetate (50 ml), cyclohexane (50 ml) and saturated ammonium chloride solution (250 ml). The aqueous phase is extracted twice with in each case 100 ml of ethyl acetate/cyclohexane (1:1). The combined organic phases are washed with water and saturated sodium chloride solution and dried over sodium sulfate. The solvent is removed under reduced pressure, giving an oil which crystallizes after addition of cyclohexane. The crystals are filtered off with suction and washed thoroughly with cyclohexane, giving a solid.

Yield: 7.68 g (90% of theory)
LC-MS (Method 2): R$_t$=2.16 min.
MS (ESI neg.): m/z=270 [M−H]⁻.
¹H-NMR (DMSO-d₆, 400 MHz): δ=3.72 (s, 6H), 5.44 (s, 1H), 7.75 (dd, 1H), 8.13 (dd, 1H), 8.18 (dd, 1H).

Example 14A

Ethyl (2-fluoro-4-nitrophenyl)acetate

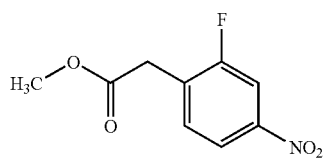

500 mg (1.84 mmol) of dimethyl (2-fluoro-4-nitrophenyl) malonate are dissolved in 10 ml of DMSO. 33.2 mg (1.84 mmol) of water and 313 mg (7.37 mmol) of lithium chloride are added, and the mixture is heated at 100° C. for 3 hours. The reaction solution is then poured into 30 ml of ethyl acetate and shaken with saturated sodium chloride solution and with dilute hydrochloric acid. The mixture is dried over sodium sulfate and the solvent is removed under reduced pressure. The oil obtained is purified by preparative HPLC.

The product fractions are extracted with ethyl acetate. The combined organic phases are dried over sodium sulfate and the solvent is removed under reduced pressure. This gives an oil which, after seeding with product crystals, quickly crystallizes.

Yield: 254 mg (63% of theory)
LC-MS (Method 1): $R_t$=1.92 min.
MS (ESI pos.): m/z=214 [M+H]$^+$.
$^1$H-NMR (DMSO-d$_6$, 300 MHz): δ=3.65 (s, 3H), 3.92 (d, 2H), 7.69 (dd, 1H), 8.06-8.13 (m, 2H).

Example 15A

Methyl (6-chloro-1-{[2-(trimethylsilyl)ethoxy]methyl}-1H-pyrrolo[2,3-b]pyridin-4-yl)(2-fluoro-4-nitrophenyl)acetate

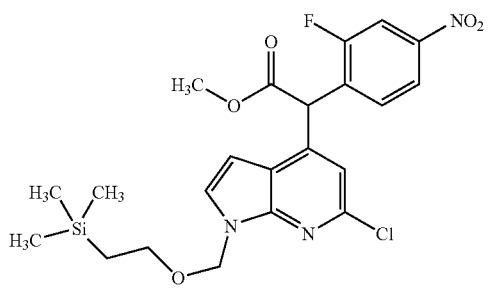

908 mg (4.26 mmol) of ethyl (2-fluoro-4-nitrophenyl)acetate are dissolved in 10 ml of DMF, and 170 mg (4.26 mmol) of sodium hydride (60% in mineral oil) are added. The mixture is stirred at RT for 30 min, and 698 mg (2.13 mmol) of 6-chloro-4-nitro-1-{[2-(trimethylsilyl)ethoxy]methyl}-1H-pyrrolo[2,3-b]pyridine are then added. The mixture is heated at 70° C. for 2 hours and then stirred into ice-water and extracted with ethyl acetate. The organic phase is washed with water and saturated sodium chloride solution, dried over sodium sulfate and concentrated under reduced pressure. The product is purified by chromatography on silica gel (mobile phase: dichloromethane/pentane 2:1).

Yield: 1.00 g (95% of theory)
LC-MS (Method 2): $R_t$=3.24 min.
MS (ESI pos.): m/z=494, 496 [M+H]$^+$.
$^1$H-NMR (DMSO-d$_6$, 400 MHz): δ=−0.12 (s, 9H), 0.80 (t, 2H), 3.52 (t, 2H), 3.74 (s, 3H), 5.57 (s, 2H), 6.02 (s, 1H), 6.60 (d, 1H), 7.15 (s, 1H), 7.57 (dd, 1H), 7.72 (d, 1H), 8.05 (dd, 1H), 8.17 (dd, 1H).

Example 16A

6-Chloro-4-(2-fluoro-4-nitrobenzyl)-1-{[2-(trimethylsilyl)ethoxy]methyl}-1H-pyrrolo[2,3-b]pyridine

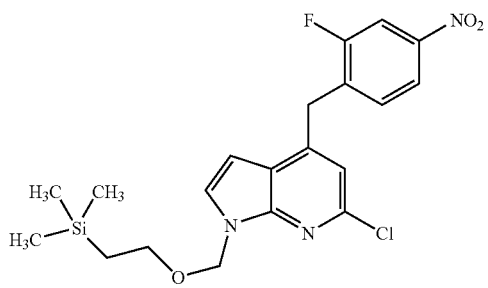

358 mg (0.72 mmol) of methyl (6-chloro-1-{[2-(trimethylsilyl)ethoxy]methyl}-1H-pyrrolo[2,3-b]pyridin-4-yl)(2-fluoro-4-nitrophenyl)acetate are dissolved in 6 ml of methanol. 21 mg (0.87 mmol) of lithium hydroxide and 2 drops of water are added, and the mixture is stirred at RT for 20 hours. The mixture is concentrated under reduced pressure, dichloromethane and water are added and the organic phase is separated off and dried over sodium sulfate. The solvent is removed under reduced pressure and the product is purified by chromatography on silica gel (mobile phase: dichloromethane). This gives an oil.

Yield: 260 mg (82% of theory)

LC-MS (Method 1): $R_t$=3.14 min.

MS (ESI pos.): m/z=436, 438 [M+H]$^+$.

$^1$H-NMR (DMSO-d$_6$, 400 MHz): δ=−0.12 (s, 9H), 0.81 (t, 2H), 3.50 (t, 2H), 4.42 (s, 2H), 5.55 (s, 2H), 6.64 (d, 1H), 7.05 (s, 1H), 7.65-7.70 (m, 2H), 8.06 (dd, 1H), 8.12 (dd, 1H).

Example 17A

3-Fluoro-4-[(1-{[2-(trimethylsilyl)ethoxy]methyl}-1H-pyrrolo[2,3-b]pyridin-4-yl)methyl]aniline

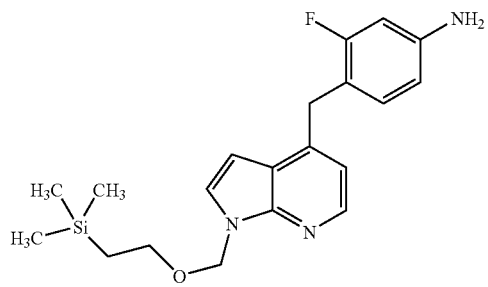

270 mg (0.62 mmol) of 6-chloro-4-(2-fluoro-4-nitrobenzyl)-1-{[2-(trimethylsilyl)ethoxy]methyl}-1H-pyrrolo[2,3-b]pyridine are dissolved in 2 ml of ethanol. 170 μl (1.24 mmol) of triethylamine and 50 mg of 10% palladium-on-carbon are added. The mixture is hydrogenated at RT and a hydrogen pressure of 1.5 bar for 20 h. The mixture is filtered and concentrated, ethyl acetate is added and the mixture is washed with 1N aqueous sodium hydroxide solution. The organic phase is dried over sodium sulfate and concentrated. The product is reacted further without purification.

Yield: 199 mg (87% of theory)

LC-MS (Method 2): $R_t$=2.81 min.

MS (ESI pos.): m/z=372 [M+H]$^+$.
$^1$H-NMR (DMSO-d$_6$, 400 MHz): δ=−0.11 (s, 9H), 0.80 (t, 2H), 3.45 (t, 2H), 4.03 (s, 2H), 5.25 (s, 2H), 5.59 (s, 2H), 6.28-6.35 (m, 2H), 6.57 (d, 1H), 6.85 (d, 1H), 6.93 (t, 1H), 7.57 (d, 1H), 8.14 (d, 1H).

Example 18A

3-Fluoro-4-(1H-pyrrolo[2,3-b]pyridin-4-ylmethyl) aniline

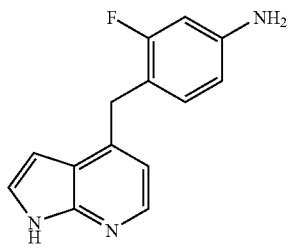

477 mg (1.00 mmol) of 3-fluoro-4-[(1-{[2-(trimethylsilyl) ethoxy]methyl}-1H-pyrrolo[2,3-b]pyridin-4-yl)methyl] aniline are dissolved in 4 ml of dichloromethane. 4.0 ml of trifluoroacetic acid are added, and the mixture is stirred at RT for 2 hours. The solution is concentrated to dryness. The residue is taken up in 15 ml of THF, and 15 ml of an aqueous 1 M lithium hydroxide solution are added. The solution is stirred at RT for 20 hours and then concentrated, and water is added. The mixture is extracted with ethyl acetate. The extract is dried over sodium sulfate and the solvent is removed under reduced pressure. The residue is purified by preparative HPLC.

Yield: 42 mg (17% of theory)
LC-MS (Method 1): $R_t$=1.18 min.
MS (ESI pos.): m/z=242 [M+H]$^+$.
$^1$H-NMR (DMSO-d$_6$, 400 MHz): δ=4.01 (s, 2H), 5.24 (s, 2H), 6.28-6.33 (m, 2H), 6.47 (dd, 1H), 6.76 (d, 1H), 6.94 (t, 1H), 7.38 (dd, 1H), 8.07 (d, 1H), 11.55 (br. s, 1H).

Example 19A

3-Methyl-1H-pyrrolo[2,3-b]pyridine 7-oxide

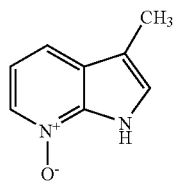

A little at a time, 3.00 g (22.70 mmol) of 3-methyl-1H-pyrrolo[2,3-b]pyridine (Hands, David; Bishop, Brian; Cameron, Mark; Edwards, John S.; Cottrell, Ian F.; Wright, Stanley H. B.; Synthesis 1996, 877-882.) are added to a solution of 10.45 g (45.40 mmol) of meta-chloroperoxybenzoic acid in 250 ml of dichloromethane, and the mixture is stirred at 10° C. for 2 h. Addition of methanol gives a clear solution which is subjected directly to column chromatography on silica gel (mobile phase: dichloromethane/methanol 100:4 to 3:1). A further purification step by preparative HPLC yields the target compound.

Yield: 1.4 g (42% of theory)
LC-MS (Method 3): $R_t$=1.22 min.
MS (ESI pos.): m/z=149 [M+H]$^+$.
$^1$H-NMR (DMSO-d$_6$, 400 MHz): δ=2.25 (s, 3H), 7.05 (dd, 1H), 7.22 (s, 1H), 7.60 (d, 1H), 8.10 (d, 1H), 11.97 (br. s, 1H).

Example 20A

4-Chloro-3-methyl-1H-pyrrolo[2,3-b]pyridine

At 50° C., 1.77 ml (22.81 mmol) of methanesulfonyl chloride are added dropwise to a solution of 1.30 g (8.77 mmol) of 3-methyl-1H-pyrrolo[2,3-b]pyridine 7-oxide in 7.5 ml of DMF such that the temperature increases to 59° C. The mixture is then stirred at 70° C. for 4 h. After cooling to room temperature, 30 ml of water are added slowly, at 5° C., the pH is adjusted to 10 by addition of 20% strength sodium hydroxide solution and the mixture is stirred for another hour. The precipitated solid is filtered off, washed with water and then dried under reduced pressure.

Yield: 395 mg (27% of theory)
LC-MS (Method 2): $R_t$=1.99 min.
MS (ESI pos.): m/z=167 (M+H)$^+$.
$^1$H-NMR (DMSO-d$_6$, 300 MHz): δ=2.43 (s, 3H), 7.08 (d, 1H), 7.32 (s, 1H), 8.08 (d, 1H), 11.65 (s, 1H).

Example 21A

N-(2-Fluoro-4-nitrophenyl)-3-methyl-1H-pyrrolo[2,3-b]pyridine-4-amine

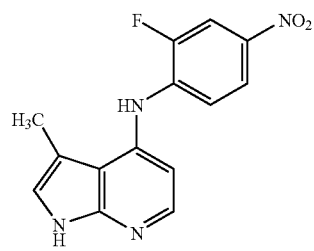

A solution of 8 mg (50 μmol) of 4-chloro-3-methyl-1H-pyrrolo[2,3-b]pyridine, 9 mg (60 μmol) of 2-fluoro-4-nitroaniline, 4 mg (5 mmol) of tris(dibenzylideneacetone)dipalladium and 5 mg (10 μmol) of dicyclohexyl(2',4',6'-triisopropylbiphenyl-2-yl)phosphine and 10 mg (70 μmol) of potassium carbonate in 1.00 ml of degassed tert-butanol is stirred at 100° C. in a sealed pressure vessel for 3 h. After cooling to RT, the mixture is filtered through Celite, the Celite is washed with methanol and the filtrates are concentrated under reduced pressure. The residue is purified by column chromatography on silica gel (mobile phase: cyclohexane/ethyl acetate 1:1).

Yield: 12 mg (87% of theory)
LC-MS (Method 3): $R_t$=1.63 nm n.
MS (ESI pos.): m/z=287 (M+H)$^+$.
$^1$H-NMR (DMSO-d$_6$, 300 MHz): δ=2.13 (s, 3H), 6.82-6.96 (m, 2H), 7.18 (s, 1H), 7.94 (d, 1H), 8.08-8.18 (m, 2H).

Example 22A

2-Fluoro-N$^1$-(3-methyl-1H-pyrrolo[2,3-b]pyridin-4-yl)benzene-1,4-diamine

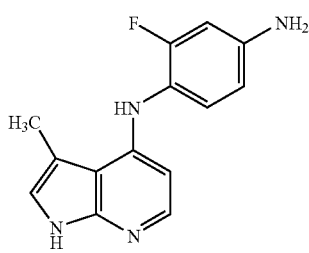

23 mg (80 µmol) of N-(2-fluoro-4-nitrophenyl)-3-methyl-1H-pyrrolo[2,3-b]pyridine-4-amine are dissolved in 12 ml of ethanol. 19 mg (19 µmol) of 10% palladium-on-carbon are added and the mixture is hydrogenated in a hydrogen atmosphere at atmospheric pressure overnight. The mixture is filtered through Celite and the solvent is removed under reduced pressure.

Yield: 17 mg (82% of theory)
LC-MS (Method 3): $R_t$=1.22 min.
MS (ESI pos.): m/z=257 (M+H)$^+$.
$^1$H-NMR (DMSO-d$_6$, 300 MHz): δ=2.45 (s, 3H), 5.36 (s, 2H), 5.82 (d, 1H), 6.37-6.50 (m, 2H), 6.86 (s, 1H), 6.93-7.09 (m, 2H), 7.68 (d, 1H), 10.87 (s, 1H).

Example 23A

3-Bromo-4-nitro-1H-pyrrolo[2,3-b]pyridine

At 0° C., 316 µl (6.13 mmol) of bromine are added dropwise to a solution of 1.00 g (6.13 mmol) of 4-nitro-1H-pyrrolo[2,3-b]pyridine (Antonini, Ippolito; Claudi, Francesco; Cristalli, Gloria; Franchetti, Palmarisa; Grifantini, Mario; Martelli, Sante; J. Med. Chem. 1982, 25, 1258-1261.) in 50 ml of dichloromethane. After 1 h of stirring at 0° C. and 1 h of stirring at room temperature, the solution is poured onto a mixture of ice and saturated sodium bicarbonate solution. The mixture is then extracted twice with dichloromethane. The combined organic phases are dried with sodium sulfate, and the solvent is removed under reduced pressure. The residue is taken up in a mixture of cyclohexane/ethyl acetate and the precipitate formed is filtered off.

Yield: 534 mg (31% of theory)
LC-MS (Method 7): $R_t$=2.40 min.
MS (ESI neg.): m/z=240 (M–H)$^-$.
$^1$H-NMR (DMSO-d$_6$, 300 MHz): δ=7.73 (s, 1H), 8.12 (d, 1H), 8.54 (d, 1H), 12.99 (d, 1H).

Example 24A

3-Bromo-4-nitro-1-{[2-(trimethylsilyl)ethoxy]methyl}-1H-pyrrolo[2,3-b]pyridine

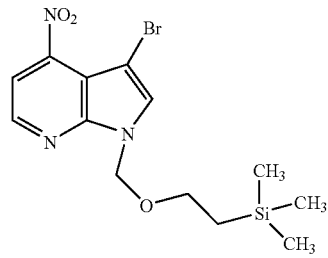

At 0° C., 18 µl (6.13 mmol) of bromine are added dropwise to a solution of 100 mg (340 µmol) of 4-nitro-1-{[2-(trimethylsilyl)ethoxy]methyl}-1H-pyrrolo[2,3-b]pyridine in 10 ml of dichloromethane. After 1 h of stirring at 0° C. and 1 h of stirring at RT, the reaction solution is filtered through an Extrelut silica gel cartridge, the cartridge is washed with a little dichloromethane/methanol and the filtrate is concentrated under reduced pressure. The residue is purified by preparative RP-HPLC.

Yield: 79 mg (62% of theory)
LC-MS (Method 9): $R_t$=2.87 min.
MS (ESI pos.): m/z=372 (M+H)$^+$.
$^1$H-NMR (DMSO-d$_6$, 300 MHz): δ=−0.03 (s, 9H), 0.92 (t, 2H), 3.63 (t, 2H), 5.81 (s, 2H), 7.92 (d, 1H), 8.42 (s, 1H), 8.71 (d, 1H).

Example 25A

3-Methyl-4-nitro-1-{[2-(trimethylsilyl)ethoxy]methyl}-1H-pyrrolo[2,3-b]pyridine

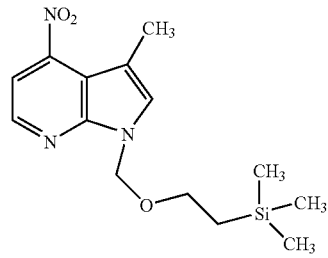

A solution of 80 mg (210 µmol) of 3-bromo-4-nitro-1-{[2-(trimethylsilyl)ethoxy]methyl}-1H-pyrrolo[2,3-b]pyridine, 27 mg (210 µmol) of trimethylboroxine, 25 mg (20 µmol) of tetrakis(tri-phenylphosphine)palladium and 103 mg (640 µmol) of potassium carbonate in 2.00 ml of degassed DMF is stirred in a sealed pressure vessel at 110° C. for 6 h and then at RT overnight. The suspension is then filtered through an Extrelut silica gel cartridge, the cartridge is washed with a mixture of dichloromethane/methanol 1:1 and the filtrate is concentrated under reduced pressure. The residue is purified by preparative RP-HPLC.

Yield: 28 mg (42% of theory)
LC-MS (Method 7): $R_t$=3.80 min.
MS (ESI pos.): m/z=309 (M+H)$^+$.
$^1$H-NMR (DMSO-d$_6$, 300 MHz): δ=−0.10 (s, 9H), 0.81 (t, 2H), 2.32 (s, 3H), 3.50 (t, 2H), 5.65 (s, 2H), 7.76 (d, 1H), 7.83 (s, 1H), 8.49 (d, 1H).

Example 26A

3-Methyl-1-{[2-trimethylsilyl)ethoxy]methyl}-1H-pyrrolo[2,3-b]pyridine-4-amine

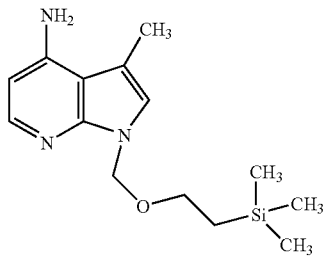

A mixture of 27 mg (90 μmol) of 3-methyl-4-nitro-1-{[2-(trimethylsilyl)ethoxy]methyl}-1H-pyrrolo[2,3-b]pyridine and 10 mg (40 μmol) of platinum(IV) oxide in 8 ml of ethanol/THF (1:1) is stirred in a hydrogen atmosphere under atmospheric pressure overnight. The suspension is then filtered through Celite and the Celite is washed with ethanol. Concentration of the filtrates gives the target product.

Yield: 21 mg (83% of theory)
LC-MS (Method 9): $R_t$=1.70 min.
MS (ESI pos.): m/z=278 (M+H)$^+$.

Example 27A

N-(2-Fluoro-4-nitrophenyl)-3-methyl-1-{[2-(trimethylsilyl)ethoxy]methyl}-1H-pyrrolo[2,3-b]pyridine-4-amine

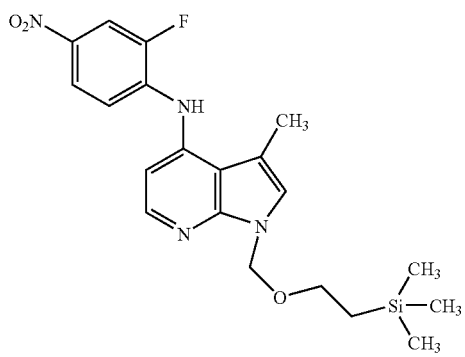

A solution of 29 mg (100 μmol) of 3-methyl-1-{[2-(trimethylsilyl)ethoxy]methyl}-1H-pyrrolo[2,3-b]pyridine-4-amine, 33 mg (130 μmol) of 2-fluoro-1-iodo-4-nitrobenzene, 5 mg (10 μmol) of tris-(dibenzylideneacetone)dipalladium, 6 mg (10 mmol) of 1,1'-bis(diphenylphosphino)ferrocene and 14 mg (150 mmol) of sodium tert-butoxide in 3 ml of degassed toluene is stirred at 100° C. overnight. After cooling to RT, the reaction mixture is directly applied to a silica gel column and separated (mobile phase: cyclohexane/ethyl acetate 10:1 to 8:2).

Yield: 20 mg (46% of theory)
LC-MS (Method 9): $R_t$=2.78 min.
MS (ESI pos.): m/z=417 (M+H)$^+$.

Example 28A

2-Fluoro-N$^1$-(3-methyl-1-{[2-(trimethylsilyl)ethoxy]methyl}-1H-pyrrolo[2,3-b]pyridin-4-yl)benzene-1,4-diamine

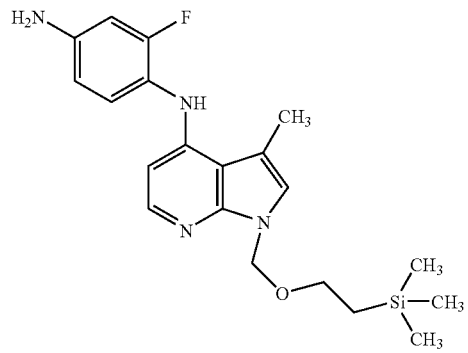

20 mg (50 μmol) of N-(2-fluoro-4-nitrophenyl)-3-methyl-1-{[2-(trimethylsilyl)ethoxy]methyl}-1H-pyrrolo[2,3-b]pyridine-4-amine are dissolved in 8 ml of a mixture of ethanol/THF (1:1). 11 mg (50 μmol) of platinum(I) oxide are added, and the mixture is stirred under a hydrogen atmosphere at atmospheric pressure overnight. The suspension is then filtered through Celite, the Celite is washed with a little ethanol and the solvent is removed under reduced pressure.

Yield: 17 mg (95% of theory)
LC-MS (Method 8): $R_t$=2.39 min.
MS (ESI pos.): m/z=387 (M+H)$^+$.

Example 29A 4-(Dibenzylamino)-2,6-difluorobenzoic acid

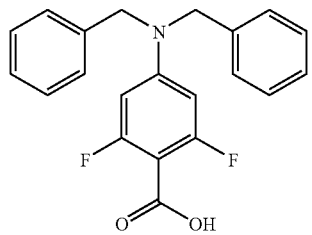

At −78° C., 10.0 g (32.3 mmol) of N,N-dibenzyl-3,5-difluoroaniline (Florvall, Lennart; Fagervall, Ingrid; Larsson, Lars-Gunnar; Ross, Svante B.; Eur. J. Med. Chem. Chim. Ther. 1999, 34, 137-152.) are initially charged in 90 ml of THF. 12.9 ml (32.3 mmol) of a 2.5 M solution of n-butyllithium in hexane are added dropwise, and the mixture is stirred at this temperature for 45 min. Excess dry ice is then

Example 30A

Ethyl [4-(dibenzylamino)-2,6-difluorophenyl]carbamate

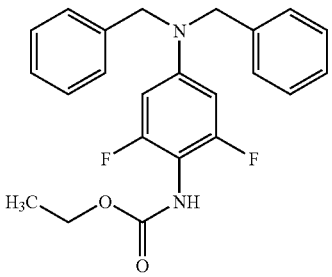

2.60 g (7.36 mmol) of 4-(dibenzylamino)-2,6-difluorobenzoic acid are dissolved in 20 ml of dioxane. 2.42 g (8.83 mmol) of diphenylphosphyl azide and then 1.08 g (10.7 mmol) of triethylamine are added dropwise, and the mixture is stirred at RT for one hour. 6.0 ml of ethanol are then added, and the mixture is heated under reflux for 2 hours. The reaction solution is then concentrated and the residue is dissolved in dichloromethane. The solution is washed with semiconcentrated sodium bicarbonate solution and water and dried over sodium sulfate, and the solvent is removed under reduced pressure. The residue is purified by chromatography on silica gel (mobile phase: dichloromethane). The oil obtained is dissolved in a little dichloromethane. Addition of a little pentane and scratching yields crystals which are filtered off with suction.

Yield: 2.2 g (75% of theory)

LC-MS (Method 2): $R_t$=2.86 min.

MS (ESI pos.): m/z=397 (M+H)$^+$.

$^1$H-NMR (DMSO-d$_6$, 400 MHz): δ=1.18 (t, 3H), 4.03 (q, 2H), 4.73 (s, 4H), 6.30-6.37 (m, 2H), 7.22-7.28 (m, 6H), 7.32-7.37 (m, 4H), 8.55 (br. s, 1H).

Example 31A

N$^4$,N$^4$-Dibenzyl-2,6-difluorobenzene-1,4-diamine

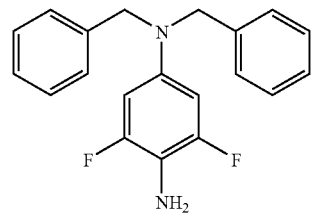

2.10 g (5.30 mmol) of ethyl [4-(dibenzylamino)-2,6-difluorophenyl]carbamate are dissolved in 40 ml of ethanol. 3.0 g (53 mmol) of powdered potassium hydroxide are added, and the mixture is heated at reflux for 20 hours. The solvent is then removed, and water and dichloromethane are added to the residue. The organic phase is separated off, washed three times with water, dried over sodium sulfate and concentrated. The residue is taken up in ethyl acetate and clarified over activated carbon. Using pentane, crystals are obtained which are filtered off with suction.

Yield: 1.2 g (70% of theory)

LC-MS (Method 3): $R_t$=2.91 min.

MS (ESI pos.): m/z=325 (M+H)$^+$.

$^1$H-NMR (DMSO-d$_6$, 300 MHz): δ=4.56 (s, 4H), 6.21-6.36 (m, 2H), 7.19-7.36 (m, 10H).

Example 32A

N$^4$,N$^4$-Dibenzyl-2,6-difluoro-N$^1$-1H-pyrrolo[2,3-b]pyridin-4-ylbenzene-1,4-diamine

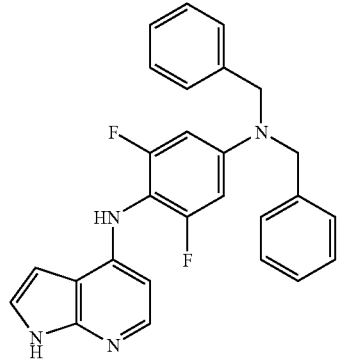

A solution of 100 mg (660 μmol) of 4-chloro-1H-pyrrolo[2,3-b]pyridine, 255 mg (790 μmol) of 2-N$^4$,N$^4$-dibenzyl-2,6-difluorobenzene-1,4-diamine, 30 mg (30 μmol) of tris(dibenzylideneacetone)-dipalladium and 31 mg (70 μmol) of dicyclohexyl(2',4',6'-triisopropylbiphenyl-2-yl)phosphine and 199 mg (1.44 mmol) of potassium carbonate in 1.50 ml of degassed tert-butanol is stirred in a sealed pressure vessel at 100° C. for 3 h. After cooling to RT, the mixture is filtered through Celite, the Celite is washed with ethyl acetate/methanol (1:1) and the filtrates are concentrated under reduced pressure. Column chromatography of the residue on silica gel (mobile phase: cyclohexane/ethyl acetate 1:1, ethyl acetate/methanol 100:1 to 95:5) yields the target product. The compound is reacted without further purification.

Yield: 122 mg (42% of theory)
LC-MS (Method 3): $R_t$=2.20 min.
MS (ESI pos.): m/z=441 (M+H)$^+$.
1H-NMR (DMSO-d$_6$, 400 MHz): δ=4.76 (s, 4H), 5.82 (d, 1H), 6.48-6.58 (m, 3H), 7.12 (s, 1H), 7.21-7.43 (m, 10H), 7.76 (d, 1H), 7.91 (s, 1H), 11.25 (s, 1H).

Example 33A 2,6-Difluoro-N$^1$-1H-pyrrolo[2,3-b]pyridin-4-ylbenzene-1,4-diamine

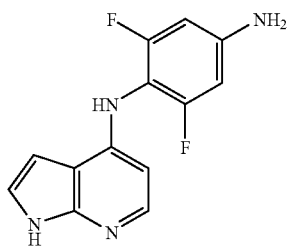

706 µl (706 µmol) of aqueous 1 M hydrochloric acid solution and 25 mg (24 µmol) of 10% palladium-on-carbon are added to a solution of 140 mg (235 µmol) of N$^4$,N$^4$-dibenzyl-2,6-difluoro-N'-1H-pyrrolo[2,3-b]pyridin-4-ylbenzene-1,4-diamine in 40 ml of ethanol, and the mixture is hydrogenated in a hydrogen atmosphere at atmospheric pressure overnight. The mixture is filtered through Celite, the solvent is removed under reduced pressure and the residue is purified by preparative RP-HPLC.
Yield: 52 mg (86% of theory)
LC-MS (Method 3): $R_t$=0.74 min.
MS (ESI pos.): m/z=261 (M+H)$^+$.
$^1$H-NMR (DMSO-d$_6$, 300 MHz): δ=6.02 (s, 2H), 6.16-6.35 (m, 1H), 6.39 (s, 1H), 6.40 (s, 1H), 7.29-7.43 (m, 1H), 7.98 (d, 1H), 9.66 (s, 1H), 12.38 (s, 1H).

Example 34A

1-Methyl-4-nitro-1H-pyrrolo[2,3-b]pyridine

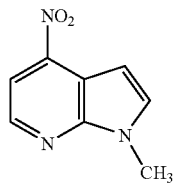

170 mg (4.29 mmol) of sodium hydride are added to a solution of 500 mg (3.06 mmol) of 4-nitro-1H-pyrrolo[2,3-b]pyridine (Antonini, Ippolito; Claudi, Francesco; Cristalli, Gloria; Franchetti, Palmarisa; Grifantini, Mario; Martelli, Sante; J. Med. Chem. 1982, 25, 1258-1261.) in 10 ml of absolute DMA, and the suspension is stirred for 30 min. A solution of 230 µl (3.68 mmol) of methyl iodide in 2 ml of absolute DMA is then slowly added dropwise, and the mixture is again stirred for 60 min. After concentration under reduced pressure, the residue is purified by column chromatography on silica gel (mobile phase: cyclohexane/ethyl acetate 10:1).

Yield: 318 mg (59% of theory)
LC-MS (Method 8): $R_t$=3.10 min.
MS (ESI pos.): m/z=178 (M+H)$^+$.
$^1$H-NMR (DMSO-d$_6$, 300 MHz): δ=3.93 (s, 3H), 6.69 (d, 1H), 7.94 (d, 1H), 7.99 (d, 1H), 8.56 (d, 1H).

Example 35A

1-Methyl-1H-pyrrolo[2,3-b]pyridine-4-amine

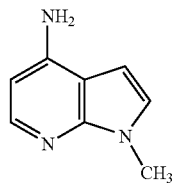

300 mg (1.69 mmol) of 1-methyl-4-nitro-1H-pyrrolo[2,3-b]pyridine are dissolved in a mixture of 20 ml of ethanol/THF (1:1). 38 mg (0.17 mmol) of platinum(IV) oxide are added, and the mixture is hydrogenated in a hydrogen atmosphere at atmospheric pressure overnight. The mixture is filtered through Celite and the solvent is removed under reduced pressure.
Yield: 265 mg (quant.)
LC-MS (Method 10): $R_t$=1.70 min.
MS (ESI pos.): m/z=148 (M+H)$^+$.
$^1$H-NMR (DMSO-d$_6$, 400 MHz): δ=3.68 (s, 3H), 6.02-6.21 (m, 3H), 6.47 (d, 1H), 7.07 (d, 1H), 7.74 (d, 1H).

Example 36A

N-(2-Fluoro-4-nitrophenyl)-1-methyl-1H-pyrrolo[2,3-b]pyridine-4-amine

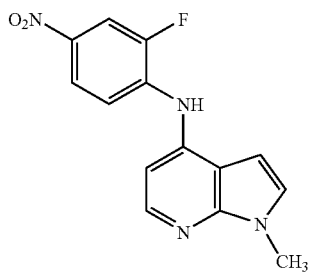

A solution of 260 mg (1.77 mmol) of 1-methyl-1H-pyrrolo[2,3-b]pyridine-4-amine, 566 mg (2.12 mmol) of 2-fluoro-1-iodo-4-nitrobenzene, 81 mg (0.09 mmol) of tris(dibenzylidene-acetone)dipalladium, 98 mg (0.18 mmol) of 1,1'-bis(diphenylphosphino)ferrocene and 238 mg (2.47 mmol) of sodium tert-butoxide in 8 ml of degassed toluene is stirred at 100° C. overnight. After cooling to RT, the reaction mixture is applied directly to a silica gel column and separated (mobile phase: cyclohexane/ethyl acetate 10:1 to 1:1).
Yield: 210 mg (42% of theory)
LC-MS (Method 8): $R_t$=1.89 min.
MS (ESI pos.): m/z=287 (M+H)$^+$.
$^1$H-NMR (DMSO-d$_6$, 300 MHz): δ=3.80 (s, 3H), 6.48 (d, 1H), 6.83 (d, 1H), 7.35 (dd, 1H), 7.40 (d, 1H), 8.03 (d, 1H), 8.13 (d, 1H), 8.18 (d, 1H), 9.32 (s, 1H).

Example 37A

2-Fluoro-N[1]-(1-methyl-1H-pyrrolo[2,3-b]pyridin-4-yl)benzene-1,4-diamine

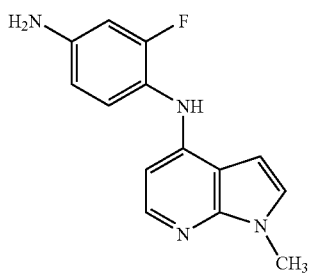

195 mg (0.68 mmol) of N-(2-fluoro-4-nitrophenyl)-1-methyl-1H-pyrrolo[2,3-b]pyridine-4-amine are dissolved in 10 ml of a mixture of ethanol/THF. (1:1). 15 mg (0.07 mmol) of platinum(IV) oxide are added, and the mixture is stirred under a hydrogen atmosphere at atmospheric pressure overnight. The suspension is then filtered through Celite, the Celite is washed with a little ethanol and the solvent is removed under reduced pressure.

Yield: 204 mg (quant.)
LC-MS (Method 10): $R_t$=2.10 min.
MS (ESI pos.): m/z=257 (M+H)$^+$.
$^1$H-NMR (DMSO-$d_6$, 300 MHz): δ=3.73 (s, 3H), 5.41 (s, 2H), 5.98 (d, 1H), 6.34-6.58 (m, 3H), 6.99 (dd, 1H), 7.17 (d, 1H), 7.81 (d, 1H), 8.13 (s, 1H).

Example 38A (4-Nitrophenyl)-1H-pyrrolo[2,3-b]pyridine-4-amine

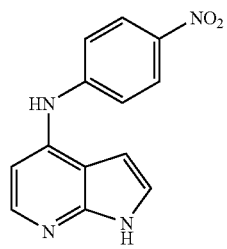

A solution of 300 mg (1.97 mmol) of 4-chloro-1H-pyrrolo[2,3-b]pyridine, 326 mg (2.36 mmol) of 4-nitroaniline, 90 mg (0.10 mmol) of tris(dibenzylideneacetone)dipalladium, 51 mg (0.1 mmol) of dicyclohexyl(2',4',6'-triisopropylbiphenyl-2-yl)phosphine and 598 mg (4.33 mmol) of potassium carbonate in 3.00 ml of degassed tert-butanol is stirred in a sealed pressure vessel at 100° C. for 3 h. After cooling to RT, the reaction mixture is filtered through kieselguhr, the kieselguhr is washed with ethyl acetate/methanol 100:5 and the solvent of the filtrate is removed. The residue is taken up in dichloromethane. The crystallized solid is filtered off, washed with dichloromethane and dried. Mother liquor and filtrate are combined and concentrated under reduced pressure. Purification of the residue by preparative HPLC yields the target product.

Yield: 340 mg (78% of theory)
LC-MS (Method 3): $R_t$=1.38 min.
MS (ESI pos.): m/z=255 (M+H)$^+$.
$^1$H-NMR (DMSO-$d_6$, 300 MHz): δ=6.48-6.58 (m, 1H), 6.97 (d, 1H), 7.28-7.42 (m, 3H), 8.08 (d, 1H), 8.19 (d, 2H), 9.55 (s, 1H), 11.62 (s, 1H).

Example 39A

N-1H-Pyrrolo[2,3-b]pyridin-4-ylbenzene-1,4-diamine

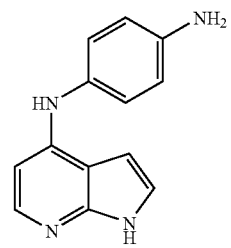

36 mg of 10% palladium-on-carbon are added to a solution of 170 mg (0.67 mmol) of N-(4-nitrophenyl)-1H-pyrrolo[2,3-b]pyridine-4-amine in 6 ml of ethanol, and the suspension is stirred in a hydrogen atmosphere at atmospheric pressure overnight. The suspension is filtered through Celite and the Celite is washed with ethanol. Concentration under reduced pressure gives the target product.

Yield: 151 mg (100% of theory)
LC-MS (Method 1): $R_t$=2.10 min.
MS (ESI pos.): m/z=225 (M+H)$^+$.
$^1$H-NMR (DMSO-$d_6$, 300 MHz): δ=4.98 (s, 2H), 6.24 (d, 1H), 6.51 (d, 1H), 6.59 (d, 2H), 6.95 (d, 2H), 7.08 (d, 1H), 7.50 (d, 1H), 8.12 (s, 1H), 11.15 (s, 1H).

Example 40A

N-(2-Fluoro-4-nitrophenyl)-1-{[2-(trimethylsilyl)ethoxy]methyl}-1H-pyrrolo[2,3-b]pyridine-4-amine

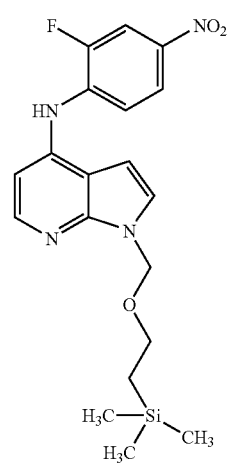

A solution of 300 mg (1.06 mmol) of 4-chloro-1-{[2-(trimethylsilyl)ethoxy]methyl}-1H-pyrrolo[2,3-b]pyridine, 199 mg (1.27 mmol) of 2-chloro-4-nitroaniline, 49 mg (0.05 mmol) of tris(dibenzylideneacetone)dipalladium and 51 mg (0.11 1 mmol) of dicyclohexyl(2',4',6'-triisopropyl-biphenyl-2-yl)phosphine and 322 mg (2.33 mmol) of potassium carbonate and 3.00 ml of degassed tert-butanol is stirred in a sealed pressure vessel at 100° C. for 3 h. After cooling to RT, the reaction mixture is filtered through kieselguhr, the kieselguhr is washed with ethyl acetate and the solvent of the filtrate is removed. The residue is purified by column chromatography on silica gel (mobile phase: gradient cyclohexane/ethyl acetate 10:1 to 8:2).

Yield: 403 mg (78% of theory)
LC-MS (Method 1): $R_t$=2.71 min.
MS (ESI pos.): m/z=403 (M+H)$^+$.
$^1$H-NMR (DMSO-d$_6$, 400 MHz): δ=0.00 (s, 9H), 0.91 (t, 2H), 3.61 (t, 2H), 5.69 (s, 2H), 6.59 (d, 1H), 6.94 (d, 1H), 7.47 (t, 1H), 7.60 (d, 1H), 8.14 (dd, 1H), 8.23 (d, 1H), 8.28 (dd, 1H), 9.47 (d, 1H).

Example 41A

N-(2-Fluoro-4-nitrophenyl)-N-methyl-1-{[2-(trimethylsilyl)ethoxy]methyl}-1H-pyrrolo[2,3-b]pyridine-4-amine

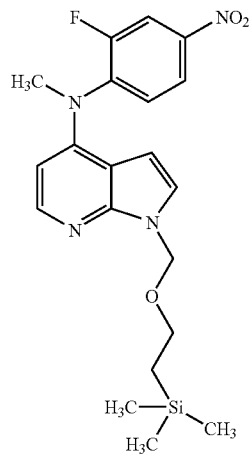

A solution of 100 mg (0.25 mmol) of N-(2-fluoro-4-nitrophenyl)-1-{[2-(trimethyl-silyl)ethoxy]methyl}-1H-pyrrolo[2,3-b]pyridine-4-amine in 0.75 ml of DMA is added dropwise to a suspension of 30 mg (0.75 mmol) of sodium hydride in 0.75 ml of DMA, and the mixture is stirred at RT for 30 min. 77 μl (1.24 mmol) of methyl iodide are then slowly added dropwise, and the mixture is stirred for a further 30 min. Water is then added, and the mixture is extracted twice with dichloromethane. The combined organic phases are dried over magnesium sulfate, the solvent is removed under reduced pressure and the residue is purified by preparative HPLC.

Yield: 71 mg (69% of theory)
LC-MS (Method 2): $R_t$=2.68 min.
MS (ESI pos.): m/z=417 (M+H)$^+$.
$^1$H-NMR (DMSO-d$_6$, 300 MHz): δ=−0.11 (s, 9H), 0.78 (t, 2H), 3.48 (t, 2H), 3.52 (s, 3H), 5.49 (d, 1H), 5.55 (s, 2H), 6.82 (d, 1H), 7.34 (d, 1H), 7.53 (dd, 1H), 8.07-8.18 (m, 3H).

Example 42A

N-(2-Fluoro-4-nitrophenyl)-N-methyl-1H-pyrrolo[2,3-b]pyridine-4-amine

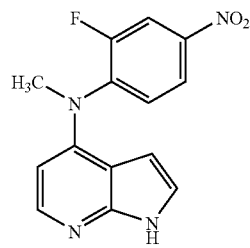

A solution of 71 mg (0.17 mmol) of N-(2-fluoro-4-nitrophenyl)-N-methyl-1-{[2-(trimethylsilyl)-ethoxy]methyl}-1H-pyrrolo[2,3-b]pyridine-4-amine in 2 ml of dichloromethane and 1.0 ml (13.0 mmol) of trifluoroacetic acid is stirred at RT for 3 h. The reaction mixture is concentrated under reduced pressure, the residue is taken up in 2 ml of THF, 1.02 ml (1.02 mmol) of aqueous 1 M lithium hydroxide solution are added and the mixture is stirred at RT overnight. To bring the reaction to completion, a further 0.5 ml (0.5 mmol) of lithium hydroxide solution is added, and the mixture is stirred for another night. Saturated sodium bicarbonate solution is added to the mixture, and the mixture is extracted twice with ethyl acetate. The combined organic phases are dried over magnesium sulfate, the solvent is removed under reduced pressure and the residue is purified by preparative HPLC.

Yield: 26 mg (54% of theory)
LC-MS (Method 2): $R_t$=1.46 min.
MS (ESI pos.): m/z=287 (M+H)$^+$.
$^1$H-NMR (DMSO-d$_6$, 400 MHz): δ=3.53 (s, 3H), 5.42-5.50 (m, 1H), 6.75 (d, 1H), 7.13-7.23 (m, 1H), 7.43-7.53 (m, 1H), 8.11 (d, 1H), 8.07-8.20 (m, 2H), 11.59 (s, 1H).

Example 43A

2-Fluoro-N$^1$-methyl-N$^1$-1H-pyrrolo[2,3-b]pyridin-4-ylbenzene-1,4-diamine

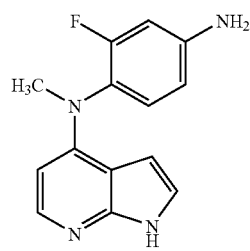

9 mg of 10% palladium-on-carbon are added to a solution of 28 mg (0.08 mmol) of N-(2-fluoro-4-nitrophenyl)-N-methyl-1H-pyrrolo[2,3-b]pyridine-4-amine in 10 ml of ethanol, and the suspension is stirred in a hydrogen atmosphere at atmospheric pressure overnight. The suspension is filtered through kieselguhr and the kieselguhr is washed with ethanol.

Concentration under reduced pressure gives the target product.

Yield: 22 mg (98% of theory)

LC-MS (Method 2): $R_t$=0.97 min.

MS (ESI pos.): m/z=257 (M+H)$^+$.

$^1$H-NMR (DMSO-d$_6$, 300 MHz): δ=3.26 (s, 3H), 5.03-5.12 (m, 1H), 5.52 (s, 2H), 6.28 (d, 1H), 6.34-6.46 (m, 2H), 6.83-6.92 (m, 1H), 6.93-7.04 (m, 1H), 7.90 (d, 1H), 11.16 (s, 1H).

Example 44A

N-(2-Chloro-4-nitrophenyl)-1H-pyrrolo[2,3-b]pyridine-4-amine

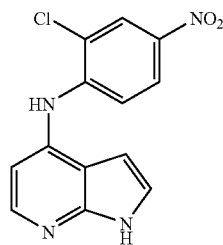

Variant A: A solution of 200 mg (1.31 mmol) of 4-chloro-1H-pyrrolo[2,3-b]pyridine, 271 mg (1.57 mmol) of 2-chloro-4-nitroaniline, 60 mg (0.07 mmol) of tris(dibenzylideneacetone)dipalladium, 62 mg (0.13 mmol) of dicyclohexyl(2',4',6'-triisopropylbiphenyl-2-yl)phosphine and 399 mg (2.88 mmol) of potassium carbonate in 2.00 ml of degassed tert-butanol is stirred in a sealed pressure vessel at 100° C. for 3 h. The mixture is then cooled to RT, and a further 136 mg (0.79 mmol) of 2-chloro-4-nitroaniline, 31 mg (0.07 mmol) of dicyclohexyl(2',4',6'-triisopropylbiphenyl-2-yl)phosphine and 30 mg (0.04 mmol of tris(dibenzylideneacetone)dipalladium are added and the mixture is stirred at 100° C. for a further 3 h.

Variant B: A mixture of 200 mg (1.31 mmol) of 4-chloro-1H-pyrrolo[2,3-b]pyridine, 678 mg (3.93 mmol) of 2-chloro-4-nitroaniline, 60 mg (0.07 mmol) of tris(dibenzylideneacetone)dipalladium, 62 mg (0.13 mmol) of dicyclohexyl(2',4',6'-triisopropylbiphenyl-2-yl)phosphine and 399 mg (2.88 mmol) of potassium carbonate and 2.50 ml of degassed tert-butanol is stirred in a sealed pressure vessel at 100° C. for 3 h.

After cooling to RT, the reaction mixtures of both synthesis variants are filtered through Celite, the Celite is washed with ethyl acetate and the filtrates are concentrated under reduced pressure. The residue is subjected to column chromatography on silica gel (mobile phase cyclohexane/ethyl acetate 10:1 to 100% ethyl acetate).

This gives 145 mg of the partially purified product (purity 67%), 30 mg of which are purified by preparative HPLC.

LC-MS (Method 1): $R_t$=1.28 min.

MS (ESI pos.): m/z=289 (M+H)$^+$.

$^1$H-NMR (DMSO-d$_6$, 300 MHz): δ=6.14-6.23 (m, 1H), 6.90 (d, 1H), 7.15 (d, 1H), 7.31-7.40 (m, 1H), 8.08 (dd, 1H), 8.12 (d, 1H), 8.34 (d, 1H), 9.01 (s, 1H), 11.68 (s, 1H).

Example 45A

2-Chloro-N$^1$-1H-pyrrolo[2,3-b]pyridin-4-ylbenzene-1,4-diamine

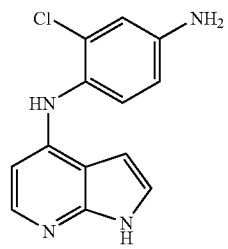

Variant A: A solution of 55 mg (130 µmol) of N-(2-chloro-4-nitrophenyl)-1H-pyrrolo[2,3-b]pyridine-4-amine and 144 mg (640 µmol) of tin(II) chloride dihydrate in 2.5 ml of DMF is stirred at RT for 4 h. A further 144 m of tin(II) chloride dihydrate are then added, and the mixture is stirred for another 4 h. The solution is then diluted with ethyl acetate, the pH is adjusted to 9-10 using saturated sodium bicarbonate solution and the mixture is filtered off through kieselguhr. The two phases of the filtrate are separated, ethyl acetate is added to the aqueous phase and this mixture is again filtered through the Celite used beforehand. After this step has been repeated, the organic phases are combined and dried over magnesium sulfate, and the solvent is removed under reduced pressure. The residue is purified by preparative HPLC.

Yield: 5 mg (15% of theory)

LC-MS (Method 1): $R_t$=0.92 min.

MS (ESI pos.): m/z=259 (M+H)$^+$.

Variant B: A solution of 10 mg (60 µmol) of iron(III) chloride in 2.40 ml of water and then 38 mg (170 µmol) of powdered iron are added to a solution of 16 mg (60 µmol) of N-(2-chloro-4-nitrophenyl)-1H-pyrrolo[2,3-b]pyridine-4-amine in 3.60 ml of ethanol. After 3 h of stirring at 80° C., the suspension is filtered through kieselguhr and the kieselguhr is washed with ethanol. The solvent is removed under reduced pressure and the residue is dissolved in a mixture of dichloromethane/methanol 10:1 and crudely purified by column filtration on silica gel. This gives 22 mg of a crude product which is directly reacted further without further purification.

Example 46A

N$^4$,N$^4$-Dibenzyl-2,6-difluoro-N$^1$-{3-methyl-1-[(4-methylphenyl)sulfonyl]-1H-pyrrolo[2,3-b]pyridin-4-yl}benzene-1,4-diamine

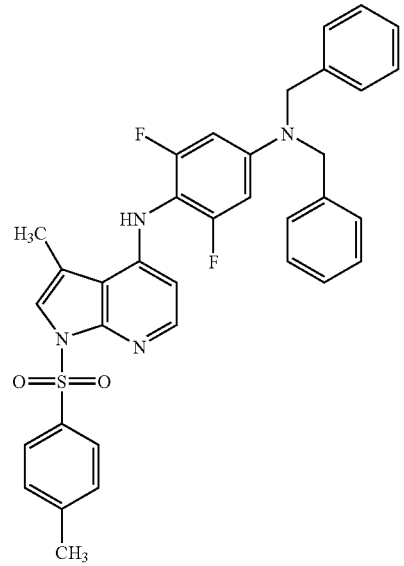

A solution of 250 mg (0.78 mmol) of 4-chloro-3-methyl-1-[(4-methylphenyl)sulfonyl]-1H-pyrrolo[2,3-b]pyridine, 303 mg (0.94 mmol) of N,N-dibenzyl-2,6-difluorobenzene-1,4-diamine, 36 mg (0.05 mmol) of tris(dibeinzylideneacetone)dipalladium, 156 mg (0.33 mmol) of dicyclohexyl(2',4',6'-triisopropylbiphenyl-2-yl)phosphine and 237 mg (1.71 mmol) of potassium carbonate in 5.00 ml of degassed tert-butanol is stirred in a sealed pressure vessel at 100° C. for 3 h. After cooling to RT, the mixture is filtered through Celite, the Celite is washed with ethyl acetate and the filtrates are concentrated under reduced pressure. The residue is purified by column chromatography on silica gel (mobile phase: cyclohexane/ethyl acetate 5:1).

Yield: 395 mg (78% of theory)

LC-MS (Method 1): $R_t$=3.08 min.

MS (ESI pos.): m/z=609 (M+H)$^+$.

$^1$H-NMR (DMSO-d$_6$, 300 MHz): δ=2.32 (s, 3H), 2.41 (s, 3H), 4.77 (s, 4H), 5.89 (d, 1H), 6.41-6.53 (m, 2H), 7.17-7.31 (m, 7H), 7.32-7.42 (m, 6H), 7.82 (d, 1H), 7.91 (d, 2H), 8.33 (s, 1H).

Example 47A

N$^4$,N$^4$-Dibenzyl-2,6-difluoro-N$^1$-(3-methyl-1H-pyrrolo[2,3-b]pyridin-4-yl)benzene-1,4-diamine

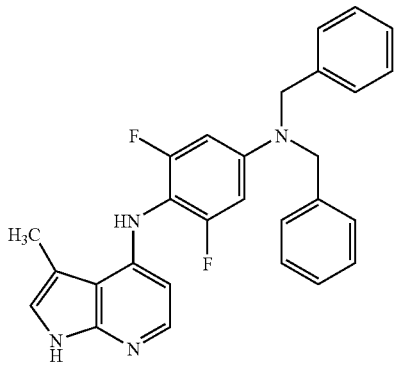

5 ml of a 20% strength aqueous sodium hydroxide solution are added to a solution of 390 mg (0.66 mmol) of N$^4$,N$^4$-dibenzyl-2,6-difluoro-N$^1$-{3-methyl-1-[(4-methylphenyl)sulfonyl]-1H-pyrrolo[2,3-b]pyridin-4-yl}benzene-1,4-diamine in 15 ml of ethanol, and the mixture is stirred overnight. The reaction solution is then poured into a mixture of water and ethyl acetate and the aqueous phase is extracted two more times with ethyl acetate. Purification by preparative HPLC affords the target compound.

Yield: 316 mg (100% of theory)

LC-MS (Method 1): $R_t$=2.02 min.

MS (ESI pos.): m/z=455 (M+H)$^+$.

$^1$H-NMR (DMSO-d$_6$, 300 MHz): δ=2.42 (s, 3H), 4.77 (s, 4H), 5.67 (d, 1H), 6.41-6.52 (m, 2H), 6.88 (d, 2H), 7.23-7.33 (m, 6H), 7.34-7.42 (m, 4H), 7.69 (d, 1H), 10.90 (s, 1H).

Example 48A 2,6-Difluoro-N$^1$-(3-methyl-1H-pyrrolo[2,3-b]pyridin-4-yl)benzene-1,4-diamine

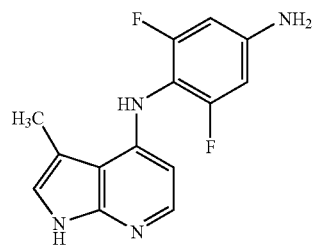

66 mg of 10% palladium-on-carbon are added to a solution of 280 mg (0.62 mmol) of N$^4$,N$^4$-dibenzyl-2,6-difluoro-N$^1$-(3-methyl-1H-pyrrolo[2,3-b]pyridin-4-yl)benzene-1,4-diamine in 20 ml of ethanol and 1.85 ml (1.85 mmol) of 1 M hydrochloric acid, and the suspension is stirred in a hydrogen atmosphere at atmospheric pressure overnight. The suspension is filtered through Celite, the Celite is washed with methanol and the filtrate is then concentrated under reduced pressure. The residue is purified by preparative HPLC.

Yield: 29 mg (17% of theory)

LC-MS (Method 1): $R_t$=1.32 min.

MS (ESI pos.): m/z=475 (M+H)$^+$.

$^1$H-NMR (DMSO-d$_6$, 300 MHz): δ=2.47 (s, 3H), 5.17-5.82 (m, 3H), 6.26-6.38 (m, 2H), 6.90 (s, 1H), 6.98 (s, 1H), 7.71 (d, 1H), 10.97 (s, 1H).

2,6-Difluor-N$^1$-(3-methyl-1H-pyrrolo[2,3-b]pyridin-4-yl)benzene-1,4-diamine hydrochloride is isolated as a further fraction.

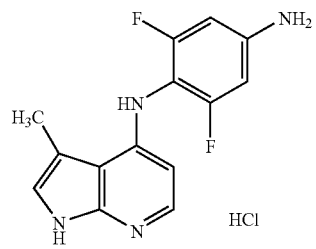

Yield: 23 mg (12% of theory)

LC-MS (Method 1): $R_t$=1.33 min.

MS (ESI pos.): m/z=475 (M+H)$^+$.

$^1$H-NMR (DMSO-d$_6$, 300 MHz): δ=2.49 (s, 3H), 6.02 (s, 2H), 6.12 (d, 1H), 6.33-6.47 (m, 2H), 6.90 (s, 1H), 6.98 (s, 1H), 7.18 (s, 1H), 7.17 (d, 1H), 7.92 (d, 1H), 8.42 (s, 1H), 12.13 (s, 1H), 14.15 (s, 1H).

Example 49A 2,2,2-Trifluoro-N-{3-fluoro-4-[(1-{[2-(trimethylsilyl)ethoxy]methyl}-1H-pyrrolo[2,3-b]pyridin-4-yl)methyl]phenyl}acetamide

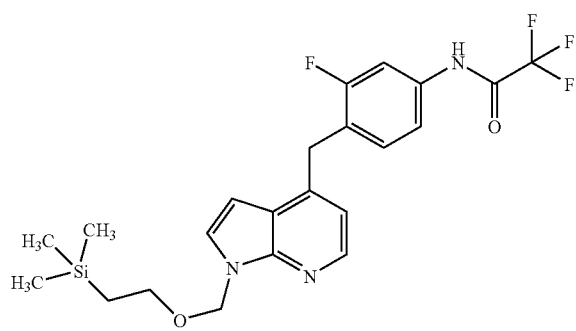

3.30 g (8.88 mmol) of 3-fluoro-4-[(1-{[2-trimethylsilyl]ethoxy]methyl}-1H-pyrrolo[2,3-b]pyridin-4-yl)methyl]aniline are initially charged in 90 ml of dichloromethane, 1.80 g (17.8 mmol) of triethylamine are added and the mixture is cooled to 0° C. 2.80 g (13.3 mmol) of trifluoroacetic anhydride are added, and the mixture is stirred at 0° C. for 1 h. Saturated sodium bicarbonate solution is then added, and the mixture is extracted. The organic phase is removed, dried over sodium sulfate and concentrated. The residue is purified by chromatography on silica gel (mobile phase: dichlormethanol:methanol=50:1). This gives an oil which crystallizes slowly.

Yield: 2.65 g (64% of theory)

HPLC (Method 2): $R_t$=3.10 min.

MS (ESI pos.): m/z=468 [M+H]$^+$.

$^1$H-NMR (DMSO-d$_6$, 400 MHz): δ=−0.12 (s, 9H), 0.79 (t, 2H), 3.50 (t, 2H), 4.24 (s, 2H), 5.60 (s, 2H), 6.59 (d, 1H), 6.90 (d, 1H), 7.35-7.44 (m, 2H), 7.57 (dd, 1H), 7.60 (d, 1H), 8.18 (d, 1H), 11.39 (s, 1H).

Example 50A

N-{4-[(3-Chloro-1-{[2-(trimethylsilyl)ethoxy]methyl}-1H-pyrrolo[2,3-b]pyridin-4-yl)methyl]-3-fluorophenyl}-2,2,2-trifluoroacetamide

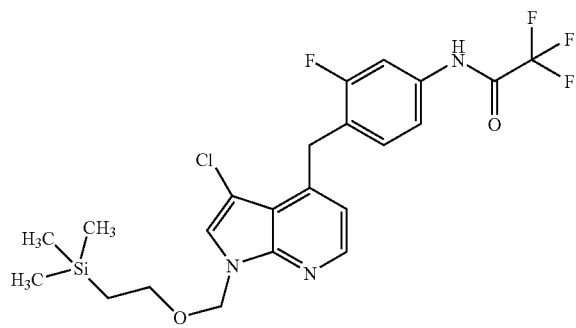

550 mg (1.07 mmol) of 2,2,2-trifluoro-N-{3-fluoro-4-[(1-{[2-(trimethylsilyl)ethoxy]methyl}-1H-pyrrolo[2,3-b]pyridin-4-yl)methyl]phenyl}acetamide and 143 mg (1.07 mmol) of N-chlorosuccinimide in 23 ml of carbon tetrachloride are heated at reflux for 20 min. After cooling, the mixture is diluted with water in dichloromethane and extracted. The organic phase is separated off, dried over magnesium sulfate and concentrated under reduced pressure. The residue is purified by column chromatography on silica gel (mobile phase: dichloromethane with increasing amounts of methanol).

Yield: 513 mg (96% of theory)

HPLC (Method 2): $R_t$=3.23 min.

MS (ESI pos.): m/z=502 [M+H]$^+$.

$^1$H-NMR (DMSO-d$_6$, 400 MHz): δ=−0.11 (s, 9H), 0.81 (t, 2H), 3.52 (t, 2H), 4.52 (s, 2H), 5.61 (s, 2H), 6.86 (d, 1H), 7.11 (t, 1H), 7.40 (dd, 1H), 7.61 (dd, 1H), 7.86 (s, 1H), 8.26 (d, 1H), 11.41 (s, 1H).

Example 51A

4-[(3-Chloro-1H-pyrrolo[2,3-b]pyridin-4-yl)methyl]-3-fluoraniline

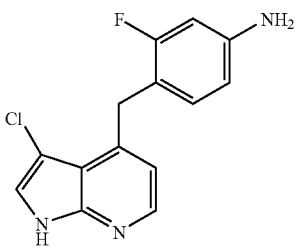

567 mg (1.13 mmol) of N-{4-[(3-chloro 1-{[2-(trimethylsilyl)ethoxy]methyl}-1H-pyrrolo[2,3-b]pyridin-4-yl)methyl]-3-fluorophenyl}-2,2,2-trifluoroacetamide are dissolved in 5 ml of dichloromethane. 5 ml (65 mmol) of trifluoroacetic acid are added, and the mixture is stirred at RT for 3 h. The mixture is then concentrated, EA is added and the mixture is washed with sat. sodium carbonate solution. The organic phase is dried over sodium sulfate and concentrated. The residue is taken up in 35 ml of THF, and 15 ml of water and 542 mg (22.7 mmol) of lithium hydroxide are added. The mixture is stirred at RT for 20 h. The mixture is then concentrated under reduced pressure, and the residue is diluted with water. The mixture is extracted with ethyl acetate and the extract is dried over sodium sulfate and concentrated. The residue is purified by chromatography on silica gel (mobile phase dichloromethane:methanol 25:1). This gives crystals.

Yield: 194 mg (62% of theory)

HPLC (Method 1): $R_t$=1.86 min.

MS (ESI pos.): m/z=276 [M+H]$^+$.

Example 52A

N-{4-[(3-Bromo-1-{[2-(trimethylsilyl)ethoxy]methyl}-1H-pyrrolo[2,3-b]pyridin-4-yl)methyl]-3-fluorophenyl}-2,2,2-trifluoroacetamide

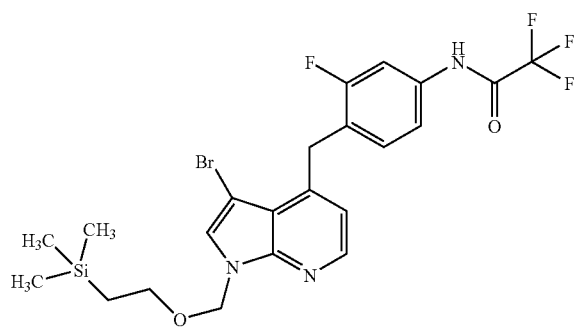

200 mg (0.38 mmol) of 2,2,2-trifluoro-N-{3-fluoro-4-[(1-{[2-(trimethylsilyl)ethoxy]methyl}-1H-pyrrolo[2,3-b]pyridin-4-yl)methyl]phenyl}acetamide and 68.5 mg (0.38 mmol) of N-bromo-succinimide in 8 ml of carbon tetrachloride are heated at reflux for 20 min. After cooling, the mixture is diluted with water and dichloromethane and extracted. The organic phase is separated off, dried over sodium sulfate and concentrated under reduced pressure.

Yield: 204 mg (97% of theory)
HPLC (Method 1): $R_t$=3.10 min.
MS (ESI pos.): m/z=546, 548 [M+H]$^+$.
$^1$H-NMR (DMSO-d$_6$, 400 MHz): δ=-0.11 (s, 9H), 0.81 (t, 2H), 3.52 (t, 2H), 4.56 (s, 2H), 5.62 (s, 2H), 6.85 (d, 1H), 7.07 (t, 1H), 7.39 (dd, 1H), 7.62 (dd, 1H), 7.90 (s, 1H), 8.26 (d, 1H), 11.45 (br. s, 1H).

Example 53A

N-{4-[(3-Bromo-1H-pyrrolo[2,3-b]pyridin-4-yl)methyl]-3-fluorophenyl}-2,2,2-trifluoroacetamide

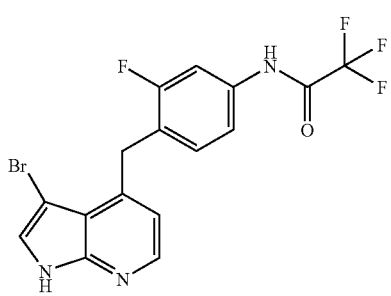

2.90 g (5.31 mmol) of N-{4-[(3-bromo-1-{[2-(trimethylsilyl)ethoxy]methyl}-1H-pyrrolo[2,3-b]-pyridin-4-yl)methyl]-3-fluorophenyl}-2,2,2-trifluoroacetamide are dissolved in 40 ml of dichloromethane. 20 ml of trifluoroacetic acid are added, and the mixture is stirred at RT for 3 h. The mixture is then concentrated, ethyl acetate is added and the mixture is shaken with saturated sodium carbonate solution. The organic phase is dried over sodium sulfate and concentrated. The crude product obtained is dissolved in 100 ml of THF, and a solution of 550 mg (22.9 mmol) of lithium hydroxide in 10 ml of water is added. The mixture is stirred at RT for 30 min and then diluted with water and extracted with ethyl acetate. The organic phase is shaken with saturated sodium chloride solution, dried over sodium sulfate and concentrated. The product is reacted without further purification.

Yield: 1.80 g (69% of theory)
HPLC (Method 2): $R_t$=2.55 min.
MS (ESI pos.): m/z=414, 416 [M+H]$^+$.
$^1$H-NMR (DMSO-d$_6$, 400 MHz): δ=4.55 (s, 2H), 6.74 (d, 1H), 7.09 (t, 1H), 7.40 (dd, 1H), 7.62 (dd, 1H), 7.68 (d, 1H), 8.18 (d, 1H), 11.42 (br. s, 1H), 12.13 (br. s, 1H).

Example 54A

N-[4-({3-Bromo-1-[(4-methylphenyl)sulfonyl]-1H-pyrrolo[2,3-b]pyridin-4-yl}methyl)-3-fluorophenyl]-2,2,2-trifluoroacetamide

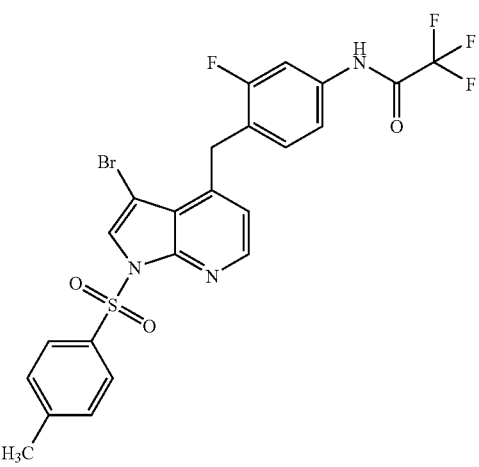

1.70 g (4.08 mmol) of N-{4-[(3-bromo-1H-pyrrolo[2,3-b]pyridin-4-yl)methyl]-3-fluorophenyl}-2,2,2-trifluoroacetamide are dissolved in 50 ml of THF and cooled to -78° C. A solution of n-butyllithium (2.81 ml, 1.6M in hexane, 4.49 mmol) is added dropwise. After 15 min, a solution of 860 mg (4.49 mmol) of p-toluenesulfonyl chloride in 5 ml of THF is added dropwise. The mixture is allowed to warm to RT and stirred for 1 h. Water and saturated sodium bicarbonate solution are then added, and the mixture is extracted with ethyl acetate. The organic phase is dried over sodium sulfate. The solvent is removed under reduced pressure and the residue is purified by column chromatography on silica gel (mobile phase dichloromethane:ethanol=50:1).

Yield: 1.10 g (47% of theory)
HPLC (Method 2): $R_t$=3.08 min.
MS (ESI pos.): m/z=570, 572 [M+H]$^+$.
$^1$H-NMR (DMSO-d$_6$, 400 MHz): δ=2.36 (s, 3H), 4.53 (s, 2H), 6.96 (d, 1H), 7.08 (t, 1H), 7.40 (dd, 1H), 7.44 (d, 2H), 7.61 (dd, 1H), 8.03 (d, 2H), 8.18 (s, 1H), 8.32 (d, 1H), 11.43 (s, 1H).

Example 55A 4-(4-Amino-2-fluorobenzyl)-1H-pyrrolo[2,3-b]pyridine-3-carbonitrile

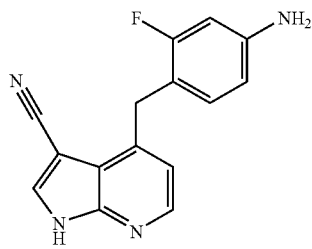

1.70 g (2.98 mmol) of N-[4-({3-bromo-1-[(4-methylphenyl)sulfonyl]-1H-pyrrolo[2,3-b]pyridin-4-yl}-methyl)-3-fluorophenyl]-2,2,2-trifluoroacetamide, 219 mg (1.19 mmol) of zinc acetate, 78 mg (1.19 mmol) of zinc dust, 189 mg (1.61 mmol) of zinc cyanide, 50.0 mg (0.09 mmol) of bis(diphenylphosphino)ferrocene and 27.3 mg (0.03 mmol) of tris(dibenzylideneacetone)dipalladium are initially charged. Under argon, a degassed mixture of 17 ml of DMF and 0.17 ml of water is added, and the mixture is heated at 100° C. for 20 hours. 10 ml of water, 8 ml of THF and 1.21 g (50.3 mmol) of lithium hydroxide are added to the crude mixture, which is then stirred at RT for 20 h. The mixture is concentrated a little and extracted with ethyl acetate. The organic phase is dried over sodium sulfate and concentrated under reduced pressure. The product is purified by chromatography on silica gel (mobile phase: dichloromethane:methanol 25:1).

Yield: 477 mg (35% of theory)
LC-MS (Method 3): $R_t$=1.84 min.
MS (ESI pos.): m/z=267 [M+H]$^+$.
$^1$H-NMR (DMSO-d$_6$, 300 MHz): δ=4.25 (s, 2H), 5.31 (s, 2H), 6.30-6.37 (m, 2H), 6.83 (d, 1H), 6.89 (t, 1H), 8.25 (d, 1H), 8.42 (s, 1H), 12.2 (br. s, 1H).

Example 56A

4-Chloro-1-[(4-methylphenyl)sulfonyl]-3-(trimethylstannyl)-1H-pyrrolo[2,3-b]pyridine

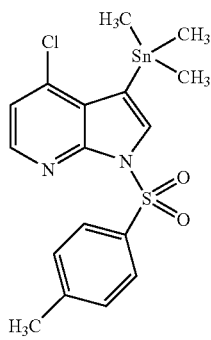

In a Schlenk flask (dried by heating under high vacuum and venting with argon), 1.0 g of 4-chloro-3-iodo-1-[(4-methylphenyl)sulfonyl]-1H-pyrrolo[2,3-b]pyridine (2.31 mmol) is initially charged in anhydrous THF (30 ml) and cooled to −78° C. 2.85 ml of tert-butyllithium (1.7 M in pentane) (4.85 mmol) is then slowly added dropwise, and the mixture is stirred at −78° C. for 30 min. 2.42 ml of a 1 M solution of trimethyltin chloride in THF are then added dropwise, and the mixture is allowed to warm to RT overnight. 10 ml of a saturated potassium fluoride solution are then added, and the organic phase is separated off and extracted once with ethyl acetate. The combined organic phases are dried over magnesium sulfate, and the solution is concentrated. The product is purified by column chromatography on silica gel (mobile phase: toluene/ethyl acetate 20:1).

LC-MS (Method 2): $R_t$=3.31 min.
MS (ESI pos.): m/z=471 (M+H)$^+$.
$^1$H-NMR (DMSO-d$_6$, 300 MHz): δ=0.40 (s, 9H), 2.35 (s, 3H), 7.40-7.45 (m, 3H), 7.67 (s, 1H), 8.05 (d, 2H), 8.30 (d, 1H).

Example 57A

4-Chloro-3-fluoro-1-[(4-methylphenyl)sulfonyl]-1H-pyrrolo[2,3-b]pyridine

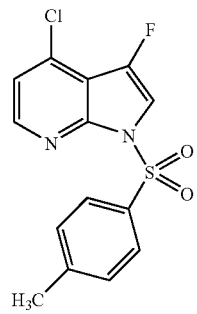

488 mg (1.03 mmol) of 4-chloro-1-[(4-methylphenyl)sulfonyl]-3-(trimethylstannyl)-1H-pyrrolo[2,3-b]pyridine are initially charged in 20 ml of anhydrous acetonitrile. 368 mg (1.03 mmol) of Selectfluor® are then added in one portion, and the mixture is allowed to stir at RT overnight. For workup, the precipitate formed is filtered off with suction and the filtrate is concentrated. The residue is purified by preparative HPLC. The product is a solid.

LC-MS (Method 3): $R_t$=2.80 min.
MS (ESI pos.): m/z=325 (M+H)$^+$.
1H-NMR (DMSO-d$_6$, 300 MHz): δ=2.34 (s, 3H), 7.43 (d, 2H), 7.52 (d, 1H), 7.97 (d, 2H), 8.15 (d, 1H), 8.40 (d, 1H).

Example 58A

3-Fluoro-N-(2-fluoro-4-nitrophenyl)-1-[(4-methylphenyl)sulfonyl]-1H-pyrrolo[2,3-b]pyridine-4-amine

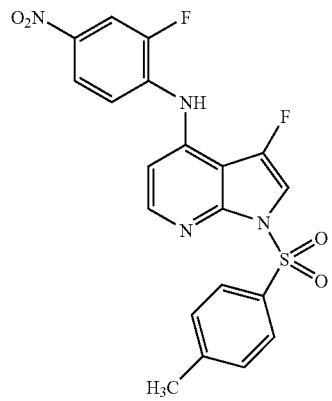

A solution of 20 mg (0.06 mmol) of 4-chloro-3-fluoro-1-[(4-methylphenyl)sulfonyl]-1H-pyrrolo[2,3-b]pyridine, 11.5 mg (0.074 mmol) of 2-fluoro-4-nitroaniline, 5.6 mg (0.006 mmol) of tris(dibenzylideneacetone)dipalladium, 5.8 mg (0.012 mmol) of dicyclohexyl(2',4',6'-triisopropyl-biphenyl-2-yl)phosphine and 12.7 mg (0.09 mmol) of potassium carbonate in 1.00 ml of degassed tert-butanol is stirred in a sealed pressure vessel at 100° C. for 3 h. After cooling to RT, the reaction mixture is filtered through kieselguhr, the kieselguhr is washed with ethyl acetate and the solvent is removed from the filtrate. The residue is purified by preparative HPLC.

Yield: 21.5 mg (67% of theory)
LC-MS (Method 1): $R_t$=2.56 min.
MS (ESI pos.): m/z=445 (M+H)$^+$.

Example 59A

3-Fluoro-N-(2-fluoro-4-nitrophenyl)-1H-pyrrolo[2,3-b]pyridine-4-amine

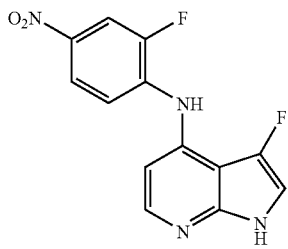

0.4 ml of a 20% strength aqueous sodium hydroxide solution is added to a solution of 80 mg (0.18 mmol) of 3-fluoro-N-(2-fluoro-4-nitrophenyl)-1-[(4-methylphenyl)-sulfonyl]-1H-pyrrolo[2,3-b]pyridine-4-amine in 5 ml of ethanol, and the mixture is stirred overnight. The reaction solution is then poured into a mixture of water and ethyl acetate, and the aqueous phase is extracted two more times with ethyl acetate. Purification by preparative HPLC gives the target compound.

Yield: 47.5 mg (91% of theory)
LC-MS (Method 1): $R_t$=1.89 min.
MS (ESI pos.): m/z=291 (M+H)$^+$.

Example 60A

2-Fluoro-N'-(3-fluoro-1H-pyrrolo[2,3-b]pyridin-4-yl)benzene-1,4-diamine

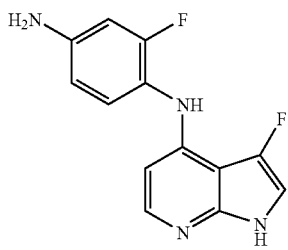

4 mg of platinum(IV) oxide are added to a solution of 47 mg (0.17 mmol) of 3-fluoro-N(2-fluoro-4-nitrophenyl)-1H-pyrrolo[2,3-b]pyridineamine in 5 ml of ethanol, and the suspension is stirred in a hydrogen atmosphere at atmospheric pressure overnight. The suspension is filtered through kieselguhr, the kieselguhr is washed with ethanol and the filtrate is concentrated. The product is purified by preparative HPLC.

Yield: 7.8 mg (16% of theory)
LC-MS (Method 2): $R_t$=1.14 min.
MS (ESI pos.): m/z=261 (M+H)$^+$.

Example 61A

4-Chloro-3-iodo-1H-pyrrolo[2,3-b]pyridine

250 g (1.64 mol) of 4-chloro-1H-pyrrolo[2,3-b]pyridine and 328 g (5.85 mol) of powdered potassium hydroxide are initially charged in 3000 ml of DMF and cooled to 0° C. With cooling, a solution of 416 g (1.64 mol) of iodine in 3000 ml of DMF is added dropwise to this suspension, and the mixture is, after the end of the addition, stirred at 0° C. for 4 h. To bring the reaction to completion, the mixture is added with stirring to ice-water and the solid formed is filtered off with suction and then dried under high vacuum. This gives 403 g (88% of theory) of the title compound as a solid.

$^1$H-NMR (DMSO-d$_6$,300 MHz): δ=7.21 (d, 1H, H-arom), 7.81 (d, 1H, H-arom), 8.19 (d, 1H, H-arom), 12.45 (br s, 1H, N–H).

Example 62A

4-Chloro-1-(toluene-4-sulfonyl)-3-iodo-1H-pyrrolo[2,3-b]pyridine

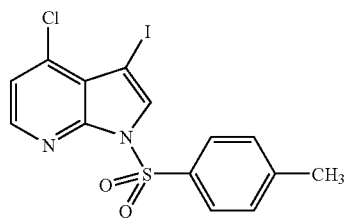

Under an atmosphere of protective gas (argon), 63.5 g (1.59 mol) of sodium hydride are suspended in 1000 ml of abs. THF. With cooling, at a temperature of 0-5° C., a solution of 402 g (1.44 mol) of 4-chloro-3-iodo-1H-pyrrolo[2,3-b]pyridine in 3000 ml of abs. THF is added dropwise, and the reaction mixture is, after the end of the addition, allowed to stir for 15 minutes. 358 g (1.88 mol) of p-toluenesulfonyl chloride are added a little at a time to the reaction mixture, so that the temperature is kept between 5 and 10° C. After the end of the addition, the mixture is allowed to warm to 20° C. and stirred at this temperature for another hour. After complete conversion (the conversion is monitored by TLC), 20 l of saturated sodium bicarbonate solution and 10 l of ethyl acetate are added to the reaction mixture, the mixture is extracted and the organic phase is separated off. The aqueous phase is reextracted two more times with in each case 10 l of ethyl acetate and the organic phases are combined, dried and, under water pump vacuum, freed from volatile components.

For purification of the crystalline crude product, the product is taken up in dichloromethane and chromatographed on silica gel (dichloromethane:petroleum ether=3:7). The solvents are removed under reduced pressure and the crystal slurry is triturated with diethyl ether, filtered off with suction and dried at 20° C. under high vacuum. 372 g (60% of theory) of the title compound are isolated as a solid.

$^1$H-NMR (DMSO-d$_6$, 300 MHz): δ=2.35 (s, 3H, —CH$_3$), 7.44 (d, 2H, H-arom), 7.46 (d, 1H, H-arom), 8.02 (d, 2H, H-arom), 8.23 (s, 1H, H-arom), 8.34 (d, 1H, H-arom).

Example 63A

4-Chloro-1-(toluene-4-sulfonyl)-3-trifluoromethyl-1H-pyrrolo[2,3-b]pyridine

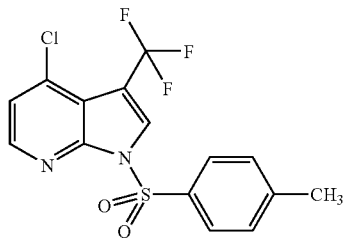

Under an atmosphere of protective gas (argon), 23.1 g (0.398 mol) of dry potassium fluoride and 75.7 g (0.398 mol) of copper(I) iodide are ground with one another and, under high vacuum and with shaking, heated at 220° C. for 10 minutes, until there is a slight greenish discoloration. The sintered mixture of potassium fluoride and copper(1) iodide together with 170 ml of absolute N-methylpyrrolidine and 170 ml of absolute DMF is initially charged in a reaction flask under an atmosphere of protective gas (argon), and 86 g (0.199 mol) of 4-chloro-1-(toluene-4-sulfonyl)-3-iodo-1H-pyrrolo[2,3-b]pyridine are then added a little at a time and with stirring at 20° C., whereupon a light-gray suspension is formed. Over a period of 20 minutes, 62.1 g (0.437 mol) of trimethyltrifluoromethylsilane are added dropwise to the reaction mixture, and the mixture is stirred at 20° C. for 18 h. After complete conversion (conversion monitored by GC), the reaction mixture is poured into 2000 ml of methyl tert-butyl ether, the organic phase is decanted and the residue is once more dispersed in 1000 ml of methyl tert-butyl ether. The combined organic phases are washed three times with in each case 2000 ml of water and then dried over magnesium sulfate. Filtration and removal of the volatile components under water pump vacuum gives 50.1 g (67% of theory) of the target compound as a solid.

$^1$H-NMR (DMSO-d$_6$, 300 MHz): δ=2.37 (s, 3H, —CH$_3$), 7.48 (d, 2H, H-arom), 7.62 (d, 1H, H-arom), 8.12 (d, 2H, H-arom), 8.47 (d, 1H, H-arom), 8.67 (s, 1H, H-arom).

Example 64A

4-Chloro-3-trifluoromethyl-1H-pyrrolo[2,3-b]pyridine

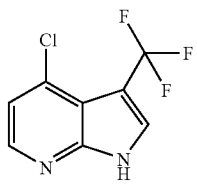

52.3 g (200 mmol) of tetra-n-butylammonium fluoride are added to a solution of 30 g (80.0 mmol) of 4-chloro-1-toluene-4-sulfonyl)-3-trifluoromethyl-1H-pyrrolo[2,3-b]pyridine in 250 ml of absolute THF, and the mixture is stirred at 20° C. for 20 minutes. After complete conversion (monitored by TLC), 300 ml of saturated sodium bicarbonate solution are added and the mixture is then extracted three times with in each case 500 ml of ethyl acetate. The combined organic phases are washed with saturated sodium chloride solution, dried over magnesium sulfate and freed from volatile components under water pump vacuum. Purification of the crystalline crude product by chromatography on silica gel (dichloromethane:methanol=30:1) affords 13.1 g (74% of theory) of the title compound as a solid.

$^1$H-NMR (DMSO-d$_6$,300 MHz): δ=7.40 (d, 1H, H-arom), 8.28 (s, 1H, H-arom), 8.34 (d, 1H, H-arom), 12.88 (br s 1H, N–H).

Example 65A

4-Chloro-3-(trifluoromethyl)-1-{[2-trimethylsilyl)ethoxy]methyl}-1H-pyrrolo[2,3-b]pyridine

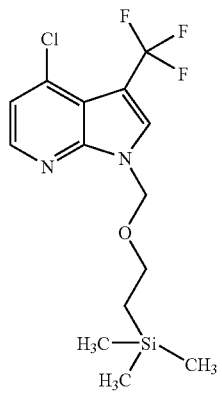

At 0° C., 37 mg (0.90 mmol) of sodium hydride are added to a solution of 200 mg (0.90 mmol) of 4-chloro-3-(trifluoromethyl)-1H-pyrrolo[2,3-b]pyridine and 177 μl (0.99 mmol) of trimethylsilyl-ethoxymethyl chloride in DMF (10 ml). The reaction mixture is stirred at RT for 1 h. The reaction mixture is poured into ice-water and stirred until the mixture reaches RT. The mixture is then extracted three times with ethyl acetate. The combined organic phases are washed successively with saturated solutions of sodium bicarbonate and sodium chloride. The organic solution is dried over magnesium sulfate and concentrated. The residue is purified by column chromatography on silica gel (mobile phase: cyclohexane/ethyl acetate 10:1).

Yield: 286 mg (90% of theory)

LC-MS (Method 2): $R_t$=3.26 min.

MS (ESI pos.): m/z=351 (M+H)$^+$.

$^1$H-NMR (DMSO-d$_6$, 300 MHz): δ=−0.09 (s, 9H), 0.93 (t, 2H), 3.63 (t, 2H), 5.84 (s, 2H), 7.48 (d, 1H), 8.40 (d, 1H), 8.52 (s, 1H).

Example 66A

N-(2-Fluoro-4-nitrophenyl)-3-(trifluoromethyl)-1-{[2-(trimethylsilyl)ethoxy]methyl}-1H-pyrrolo[2,3-b]pyridine-4-amine

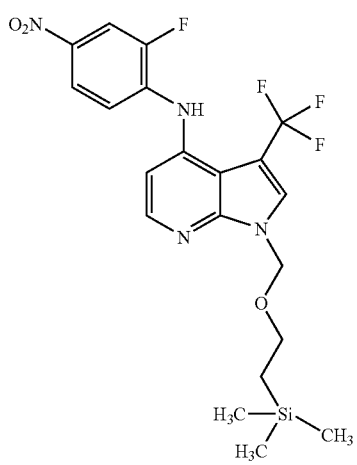

A solution of 170 mg (0.485 mmol) of 4-chloro-3-(trifluoromethyl)-1-{[2-(trimethylsilyl)ethoxy]-methyl}-1H-pyrrolo[2,3-b]pyridine, 91 mg (0.58 mmol) of 2-fluoro-4-nitroaniline, 31 mg (0.035 mmol) of tris(dibenzylideneacetone)dipalladium, 33 mg (0.07 mmol) of dicyclohexyl(2',4',6'-triisopropylbiphenyl-2-yl)phosphine and 100 mg (0.72 mmol) of potassium carbonate in 3.00 ml of degassed tert-butanol is stirred in a sealed pressure vessel at 100° C. for 3 h. After cooling to RT, the reaction mixture is filtered through kieselguhr, the kieselguhr is washed with ethyl acetate and the filtrate is freed from the solvent. The residue is purified by preparative HPLC.

Yield: 187 mg (82% of theory)

LC-MS (Method 3): $R_t$=3.32 min.

MS (ESI pos.): m/z=471 (M+H)$^+$.

$^1$H-NMR (DMSO-d$_6$, 400 MHz): δ=−0.08 (s, 9H), 0.84 (t, 2H), 3.58 (t, 2H), 5.70 (s, 2H), 7.04 (t, 1H), 7.24 (d, 1H), 7.96 (dd, 1H), 8.15 (dd, 1H), 8.40 (s, 1H), 8.43 (d, 1H), 8.47 (s, 1H).

Example 67A

N-(2-Fluoro-4-nitrophenyl)-3-(trifluoromethyl)-1H-pyrrolo[2,3-b]pyridine-4-amine

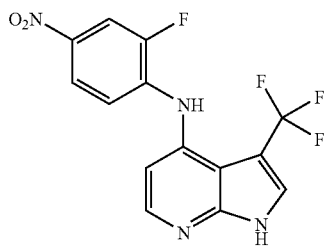

3 ml of trifluoroacetic acid are added to a solution of 182 mg (0.387 mmol) of N-(2-fluoro-4-nitrophenyl)-3-(trifluoromethyl)-1-{[2-(trimethylsilyl)ethoxy]methyl}-1H-pyrrolo[2,3-b]pyridine-4-amine in 3.00 ml of dichloromethane, and the mixture is stirred at RT for 30 min. The solvents are removed under reduced pressure. The residue is dissolved in ethyl acetate and washed successively with saturated solutions of sodium bicarbonate and sodium chloride, the organic phase is dried with magnesium sulfate and the solution is concentrated. The product is used without further purification.

Yield: 129 mg (98% of theory)

LC-MS (Method 3): $R_t$=2.71 min.

MS (ESI pos.): m/z=341 (M+H)$^+$.

Example 68A

2-Fluoro-N$^1$-{3-(trifluoromethyl)-1H-pyrrolo[2,3-b]pyridin-4-yl}benzene-1,4-diamine 10 mg of 10% palladium-on-carbon are added to a solution of 129 mg (0.38 mmol) of N-(2-fluoro-4-nitrophenyl)-3-(trifluoromethyl)-1H-pyrrolo[2,3-b]pyridine-4-amine in 5 ml of ethanol, and the suspension is stirred in a hydrogen atmosphere at atmospheric pressure overnight. The suspension is filtered through kieselguhr and the kieselguhr is washed with ethanol. The filtrate is concentrated. The product is purified by preparative HPLC.

Yield: 18 mg (15% of theory) LC-MS (Method 3): R=1.59 min.

MS (ESI pos.): m/z=311 (M+H)$^+$.

$^1$H-NMR (DMSO-d$_6$, 300 MHz): δ=6.18 (dd, 1H), 6.28 (s, 1H), 6.40-6.50 (m, 2H), 7.16 (t, 1H), 7.93 (s, 1H), 7.95 (d, 1H), 12.24 (s, 1H).

Working Examples

Example 1

N$^4$-[3-Fluoro-4-(1H-pyrrolo[2,3-b]pyridin-4-ylamino)phenyl]-6-(trifluoromethyl)pyrimidine-2,4-diamine

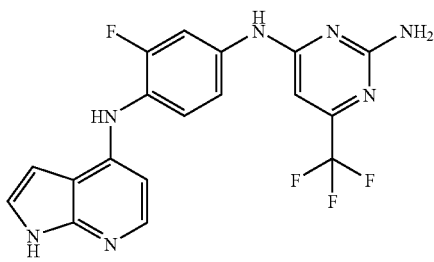

139 mg (0.5 mmol) of 2-fluoro-N$^1$-1H-pyrrolo[2,3-b]pyridin-4-yl-1,4-diaminobenzene and 147 mg (0.75 mmol) of 4-chloro-6-(trifluoromethyl)pyrimidine-2-amine are suspended in 10 ml of water. 0.75 ml of 1 M hydrochloric acid is added. The mixture is heated at 100° C. overnight. The suspension is then adjusted to pH 10 using 1N aqueous sodium hydroxide solution, resulting in the precipitation of crystals. The crystals are filtered off with suction and washed with water. The crude product is purified by column chromatography on silica gel (mobile phase: dichloromethane/methanol (7M ammonia) 100:1 to 10:1).

Yield: 62 mg (26% of theory)
LC-MS (Method 2): R$_t$=1.52 min.
MS (ESI pos.): m/z=404 [M+H]$^+$.
$^1$H-NMR (DMSO-d$_6$, 400 MHz): δ=6.13 (d, 1H), 6.38 (s, 1H), 6.53 (m, 1H), 6.97 (s, 2H), 7.16 (s, 1H), 7.29-7.40 (m, 2H), 7.83 (d, 1H), 8.11 (d, 1H), 8.33 (s, 1H), 9.82 (s, 1H), 11.27 (s, 1H).

Example 2

6-Chloro-N$^4$-[3-fluoro-4-(1H-pyrrolo[2,3-b]pyridin-4-ylamino)phenyl]pyrimidine-2,4-diamine

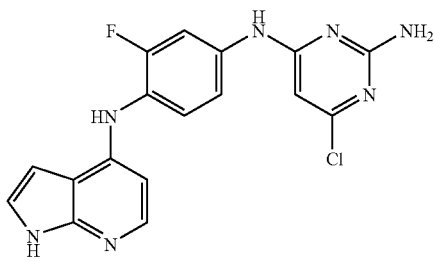

28 mg (0.12 mmol) of 2-fluoro-N$^1$-1H-pyrrolo[2,3-b]pyridin-4-yl-1,4-diaminobenzene and 27 mg (0.16 mmol) of 4,6-dichloropyrimidine-2-amine are suspended in 5 ml of water. 0.16 ml of 1 M hydrochloric acid is added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7 M ammonia) 100:1 to 10:1).

Yield: 33 mg (73% of theory)
LC-MS (Method 3): R$_t$=1.47 min.
MS (ESI pos.): m/z=370 (M+H)$^+$.
$^1$H-NMR (DMSO-d$_6$, 300 MHz): δ=6.01 (s, 1H), 6.12 (d, 1H), 6.48-6.53 (m, 1H), 6.84 (s, 2H), 7.16 (d, 1H), 7.23-7.37 (m, 2H), 7.81 (d, 1H), 8.05 (d, 1H), 8.29 (s, 1H), 9.53 (s, 1H), 11.28 (s, 1H).

Example 3

N$^4$-[3-Fluoro-4-(1H-pyrrolo[2,3-b]pyridin-4-ylamino)phenyl]pyrimidine-2,4-diamine

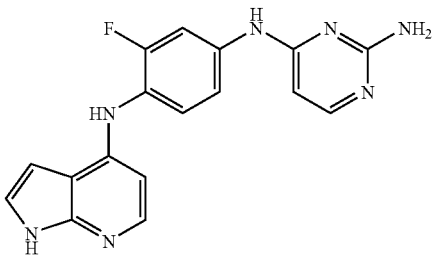

32 mg (0.10 mmol) of 2-fluoro-N'-1H-pyrrolo[2,3-b]pyridin-4-yl-1,4-diaminobenzene and 18 mg (0.14 mmol) of 4-chloropyrimidine-2-amine are suspended in 5 ml of water. 0.14 ml of 1 M hydrochloric acid is added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7 M ammonia) 100:1 to 10:1).

Yield: 19 mg (55% of theory)
LC-MS (Method 5): R$_t$=2.30 min.
MS (ESI neg.): m/z=334 (M−H)$^-$.
$^1$H-NMR (DMSO-d$_6$, 300 MHz): δ=6.02 (d, 1H), 6.10 (d, 1H), 6.30 (s, 2H), 6.48-6.53 (m, 1H), 7.16 (d, 1H), 7.20-7.29 (m, 1H), 7.31-7.87 (m, 1H), 7.72-7.89 (m, 2H), 8.11 (d, 1H), 8.27 (s, 1H), 9.38 (s, 1H), 11.26 (s, 1H).

Example 4

6-Chloro-N$^4$-{4-[(3-chloro-1H-pyrrolo[2,3-b]pyridin-4-yl)amino]-3-fluorophenyl}pyrimidine-2,4-diamine

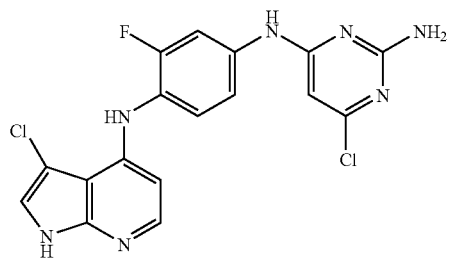

57 mg (210 mmol) of $N^1$-(3-chloro-1H-pyrrolo[2,3-b]pyridin-4-yl)-2-fluorobenzene-1,4-diamine and 47 mg (290 μmol) of 4,6-dichloropyrimidine-2-amine are suspended in 5 ml of water. 290 μl (290 mmol) of 1 M hydrochloric acid are added, and the mixture is stirred at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7M ammonia) 100:1 to 10:1) and subsequent preparative RP-HPLC.

Yield: 9 mg (11% of theory)

LC-MS (Method 2): $R_t$=1.67 min.

MS (ESI pos.): m/z=404 (M+H)$^+$.

Example 5

6-(4-Fluorophenyl)-$N^4$-[3-fluoro-4-(1H-pyrrolo[2,3-b]pyridin-4-ylamino)phenyl]pyrimidine-2,4-diamine

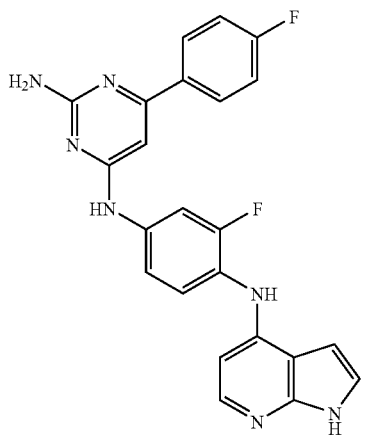

100 mg (0.27 mmol) of 2-fluoro-$N^1$-(1-{[2-(trimethylsilyl)ethoxy]methyl}-1H-pyrrolo[2,3-b]pyridin-4-yl)benzene-1,4-diamine and 63 mg (0.28 mmol) of 4-chloro-6-(4-fluorophenyl)pyrimidine-2-amine are suspended in 3 ml of water. 39 μl (0.40 mmol) of a 37% strength hydrochloric acid solution are then added, and the mixture is heated under reflux overnight. After addition of a further 39 μl (0.40 mmol) of a 37% strength hydrochloric acid solution, the mixture is again reacted under reflux overnight. Using 1N aqueous sodium hydroxide solution, the suspension is then adjusted to pH 10, resulting in the precipitation of crystals. The solid is filtered off, washed with a little water and then dissolved in DMSO and purified by preparative RP-HPLC.

Yield: 32 mg (26% of theory)

LC-MS (Method 9): $R_t$=1.33 min.

MS (ESI neg.): m/z=428 (M−H)$^−$.

$^1$H-NMR (DMSO-d$_6$, 300 MHz): δ=6.12 (d, 1H), 6.38-6.59 (m, 4H), 7.11-7.18 (m, 1H), 7.22-7.47 (m, 4H), 7.83 (d, 1H), 7.93-8.07 (m, 2H), 8.12 (d, 1H), 8.25 (s, 1H), 9.45 (s, 1H), 11.22 (s, 1H).

Example 6

$N^4$-[3-Fluoro-4-(1H-pyrrolo[2,3-b]pyridin-4-ylamino)phenyl]-6-pyridin-4-ylpyrimidine-2,4-diamine

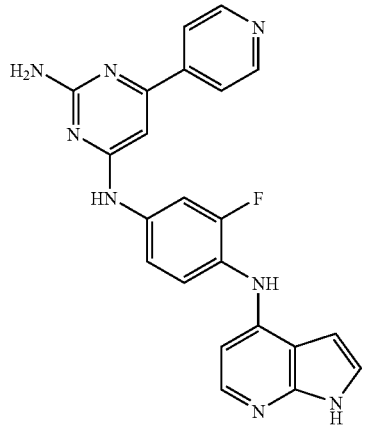

70 mg (0.19 mmol) of 2-fluoro-$N^1$-(1-{[2-(trimethylsilyl)ethoxy]methyl}-1H-pyrrolo[2,3-b]pyridine-4-yl)benzene-1,4-diamine and 41 mg (0.20 mmol) of 4-chloro-6-pyridin-4-ylpyrimidine-2-amine are suspended in 2.5 ml of water. 27 μl (0.28 mmol) of a 37% strength hydrochloric acid solution are then added, and the mixture is heated under reflux overnight. Using 1N aqueous sodium hydroxide solution, the suspension is then adjusted to pH 10, resulting in the precipitation of crystals. The solid is filtered off, washed with a little water and then dissolved in DMSO and purified by preparative RP-HPLC.

Yield: 14 mg (18% of theory)

LC-MS (Method 7): $R_t$=1.64 min.

MS (ESI pos.): m/z=413 (M+H)$^+$.

$^1$H-NMR (DMSO-d$_6$, 300 MHz): δ=6.05-6.18 (m, 1H), 6.50-6.72 (m, 4H), 7.08-7.19 (m, 1H), 7.21-7.48 (m, 2H), 7.71-7.93 (m, 3H), 8.07-8.21 (m, 1H), 8.31 (s, 1H), 8.68 (s, 1H), 9.62 (s, 1H), 11.31 (s, 1H).

Example 7

6-Chloro-N-[3-fluoro-4-(1H-pyrrolo[2,3-b]pyridin-4-ylmethyl)phenyl]pyrimidine-2,4-diamine

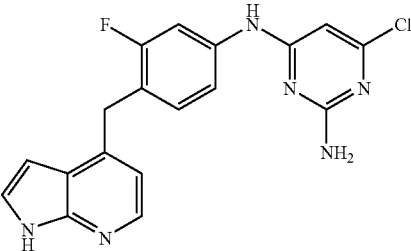

40 mg (0.15 mmol) of 3-fluoro-4-(1H-pyrrolo[2,3-b]pyridin-4-ylmethyl)aniline and 29 mg (0.18 mmol) of 4,6-dichloropyrimidine-2-amine are suspended in 2 ml of water and 0.11 ml of 2N hydrochloric acid. The reaction mixture is heated at reflux for 15 hours. After cooling, the mixture is made alkaline using dilute aqueous sodium hydroxide solution, a little DMF is added and the mixture is extracted with ethyl acetate. The extract is dried over sodium sulfate and the solvent is removed under reduced pressure. The residue is purified by preparative HPLC.

Yield: 27 mg (50% of theory)
LC-MS (Method 2): $R_t$=1.89 min.
MS (ESI pos.): m/z=369 [M+H]$^+$.
$^1$H-NMR (DMSO-d$_6$, 400 MHz): δ=4.17 (s, 2H), 5.99 (s, 1H), 6.50-6.52 (m, 1H), 6.77-6.84 (m, 3H), 7.19-7.24 (m, 2H), 7.42 (dd, 1H), 7.83 (d, 1H), 8.11 (d, 1H), 9.47 (s, 1H), 11.62 (s, 1H).

Example 8

N$^4$-[3-Fluoro-4-(1H-pyrrolo[2,3-b]pyridin-4-ylmethyl)phenyl]-6-(trifluoromethyl)pyrimidine-2,4-diamine

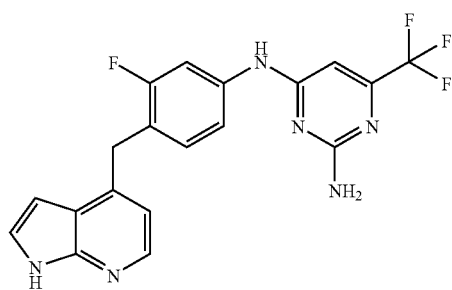

32 mg (0.11 mmol) of 3-fluoro-4-(1H-pyrrolo[2,3-b]pyridin-4-ylmethyl)aniline and 26 mg (0.12 mmol) of 4-chloro-6-(trifluoromethyl)pyrimidine-2-amine are suspended in 5 ml of water and 0.07 ml of 2N hydrochloric acid. The reaction mixture is heated at reflux for 20 hours. After cooling, the mixture is made alkaline using dilute aqueous sodium hydroxide solution, a little methanol is added and the mixture is extracted with ethyl acetate. The extract is dried over sodium sulfate and the solvent is removed under reduced pressure. The residue is purified by preparative HPLC.

Yield: 24 mg (55% of theory)
LC-MS (Method 2): $R_t$=2.05 min.
MS (ESI pos.): m/z=403 [M+H]$^+$.
$^1$H-NMR (DMSO-d$_6$, 400 MHz): δ=4.18 (s, 2H), 6.33 (s, 1H), 6.51 (dd, 1H), 6.82 (d, 1H), 6.93 (br. s, 2H), 7.21-7.29 (m, 2H), 7.41 (dd, 1H), 7.89 (dd, 1H), 8.11 (d, 1H), 9.72 (s, 1H), 11.60 (br. s, 1H).

Example 9

4-[(2-Amino-6-chloropyrimidin-4-yl)amino]-2-fluorophenyl 1H-pyrrolo[2,3-b]pyridin-4-yl ketone

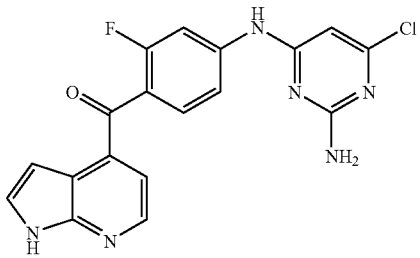

The product was obtained as a byproduct in the preparation of 6-chloro-N$^4$-[3-fluoro-4-(1H-pyrrolo[2,3-b]pyridin-4-ylmethyl)phenyl]pyrimidine-2,4-diamine after purification by HPLC.
LC-MS (Method 1): $R_t$=1.82 min.
HRMS: calculated for $C_{18}H_{12}N_6OFCl$: 382.0745; found: 382.0748.
$^1$H-NMR (DMSO-d$_6$, 400 MHz): δ=6.11 (s, 1H), 6.47 (dd, 1H), 7.01 (br. s, 2H), 7.25 (d, 1H), 7.41 (dd, 1H), 7.58 (t, 1H), 7.66 (t, 1H), 8.15 (dd, 1H), 8.39 (d, 1H), 9.96 (s, 1H), 12.05 (br. s, 1H).

Example 10

6-Chloro-N$^4$-{3-fluoro-4-[(3-methyl-1H-pyrrolo[2,3-b]pyridin-4-yl)amino]phenyl}pyrimidine-2,4-diamine

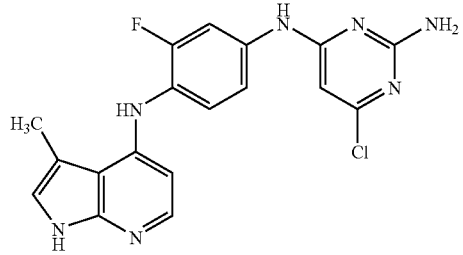

19 mg (70 μmol) of 2-fluoro-N$^1$-(3-methyl-1H-pyrrolo[2,3-b]pyridin-4-yl)benzene-1,4-diamine and 17 mg (10 μmol) of 4,6-dichloropyrimidine-2-amine are suspended in 3.5 ml of water. 100 μl of 1 M hydrochloric acid are added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7M ammonia) 100:1 to 10:1).
Yield: 9 mg (32% of theory)
LC-MS (Method 3): $R_t$=1.60 min.
MS (ESI pos.): m/z=384 (M+H)$^+$.
$^1$H-NMR (DMSO-d$_6$, 300 MHz): δ=2.45 (s, 3H), 5.98-6.08 (m, 2H), 6.83 (s, 2H), 6.95 (s, 1H), 7.23-7.36 (m, 2H), 7.40 (s, 1H), 7.78 (d, 1H), 8.00 (d, 1H), 9.51 (s, 1H), 10.99 (s, 1H).

Example 11

N⁴-{3-Fluoro-4-[(3-methyl-1H-pyrrolo[2,3-b]pyridin-4-yl)amino]phenyl}-6-(trifluoromethyl)pyrimidine-2,4-diamine

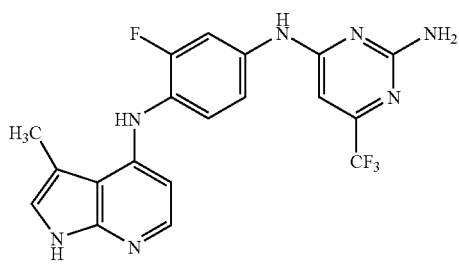

123 mg (480 mmol) of 2-fluoro-$N^1$-(3-methyl-1H-pyrrolo[2,3-b]pyridin-4-yl)benzene-1,4-diamine and 123 mg (620 μmol) of 4-chloro-6-(trifluoromethyl)pyrimidine-2-amine are suspended in 3.5 ml of water. 620 μl of 1 M hydrochloric acid are added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7 M ammonia) 100:1 to 10:1).

Yield: 154 mg (77% of theory)
LC-MS (Method 3): $R_t$=1.38 min.
MS (ESI pos.): m/z=418 (M+H)⁺.
¹H-NMR (DMSO-$d_6$, 300 MHz): δ=2.45 (s, 3H), 6.02-6.10 (m, 1H), 6.38 (s, 1H), 6.88-7.03 (m, 3H), 7.24-7.39 (m, 2H), 7.43 (s, 1H), 7.79 (d, 1H), 8.08 (d, 1H), 9.78 (s, 1H), 11.0 (s, 1H).

Example 12

N-{3-Fluoro-4-[(3-methyl-1H-pyrrolo[2,3-b]pyridin-4-yl)amino]phenyl}-2-pyridin-4-ylpyrimidine-4,6-diamine

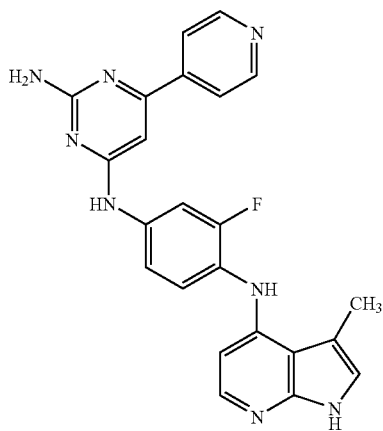

17 mg (40 μmol) of 2-fluoro-$N^1$-(3-methyl-1-{[2-(trimethylsilyl)ethoxy]methyl}-1H-pyrrolo[2,3-b]pyridin-4-yl)benzene-1,4-diamine and 10 mg (50 μmol) of 4-chloro-6-pyridin-4-ylpyrimidine-2-amine are suspended in 1 ml of water. 7 μl (70 μmol) of a 37% strength hydrochloric acid solution are then added, and the mixture is heated under reflux overnight. Using 1N aqueous sodium hydroxide solution, the suspension is then adjusted to pH 10, resulting in the precipitation of crystals. The solid is filtered off, washed with a little water and purified by column chromatography on silica gel (mobile phase: dichloromethane/methanol (7M ammonia) 100:1 to 10:1).

Yield: 3 mg (17% of theory)
LC-MS (Method 7): $R_t$=1.61 min.
MS (ESI neg.): m/z=425 (M−H)⁻.
¹H-NMR (DMSO-$d_6$, 300 MHz): δ=2.18 (s, 3H), 6.00-6.09 (m, 1H), 6.52-6.68 (m, 3H), 6.87 (s, 2H), 6.93-7.00 (m, 1H), 7.23-7.47 (m, 3H), 7.74-7.89 (m, 2H), 8.03-8.18 (m, 1H), 8.67-8.74 (m, 1H), 9.58 (s, 1H), 11.01 (s, 1H).

Example 13

6-Chloro-N-[3,5-difluoro-4-(1H-pyrrolo[2,3-b]pyridin-4-ylamino)phenyl]pyrimidine-2,4-diamine

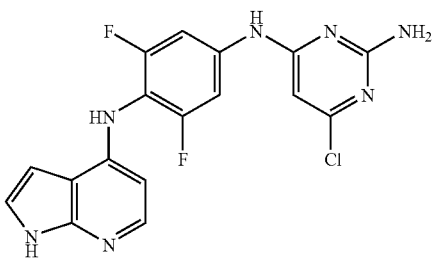

51 mg (200 μmol) of 2,6-difluoro-$N^1$-1H-pyrrolo[2,3-b]pyridin-4-ylbenzene-1,4-diamine and 45 mg (270 μmol) of 4,6-dichloropyrimidine-2-amine are suspended in 5 ml of water. 270 μl of 1 M hydrochloric acid are added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7M ammonia) 100:1 to 10:1).

Yield: 53 mg (66% of theory)
LC-MS (Method 3): $R_t$=1.52 min.
MS (ESI pos.): m/z=388 (M+H)⁺.
¹H-NMR (DMSO-$d_6$, 300 MHz): δ=5.94 (d, 1H), 6.03 (s, 1H), 6.45-6.53 (m, 1H), 6.98 (s, 2H), 7.13-7.21 (m, 1H), 7.20-7.29 (m, 1H), 7.63 (s, 1H), 7.68 (s, 1H), 7.82 (d, 1H), 8.20 (s, 1H), 9.73 (s, 1H), 11.29 (s, 1H).

Example 14

N4-{3-Fluoro-4-[(1-methyl-1H-pyrrolo[2,3-b]pyridin-4-yl)amino]phenyl}-6-pyridin-4-ylpyrimidine-2,4-diamine

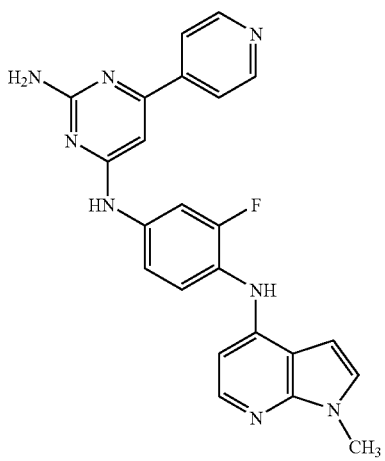

200 mg (0.78 mmol) of 2-fluoro-N1-(1-methyl-1H-pyrrolo[2,3-b]pyridin-4-yl)benzene-1,4-diamine and 169 mg (0.82 mmol) of 4-chloro-6-pyridin-4-ylpyrimidine-2-amine are suspended in 5 ml of water. 84 µl (1.01 mmol) of a 37% strength hydrochloric acid solution are then added, and the mixture is heated under reflux overnight. Using 1N aqueous sodium hydroxide solution, the suspension is then adjusted to pH 10, resulting in the precipitation of crystals. The solid is filtered off, washed with a little water and then dissolved in DMSO and purified by preparative RP-HPLC.

Yield: 50 mg (15% of theory)
LC-MS (Method 10): $R_t$=2.24 min.
MS (ESI pos.): m/z=427 (M+H)+.
1H-NMR (DMSO-$d_6$, 200 MHz): δ=3.74 (s, 3H), 6.16 (d, 1H), 6.48-6.80 (m, 4H), 7.17-7.51 (m, 3H), 7.78-8.02 (m, 3H), 8.18 (d, 1H), 8.48 (s, 1H), 8.72 (d, 2H), 9.68 (d, 1H).

Example 15

6-Chloro-N4-[4-(1H-pyrrolo[2,3-b]pyridin-4-ylamino)phenyl]pyrimidine-2,4-diamine

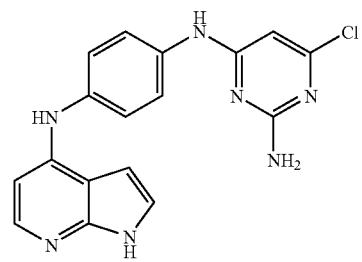

125 mg (0.56 mmol) of N-1H-pyrrolo[2,3-b]pyridin-4-yl-benzene-1,4-diamine and 118 mg (0.72 mmol) of 4,6-dichloropyrimidine-2-amine are suspended in 5 ml of water. 0.72 ml of 1 M hydrochloric acid are added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7 M ammonia) 100:1 to 10:1).

Yield: 139 mg (71% of theory) LC-MS (Method 1): $R_t$=1.54 min.
MS (ESI pos.): m/z=352 (M+H)+.
1H-NMR (DMSO-$d_6$, 400 MHz): δ=5.98 (s, 1H), 6.56 (d, 1H), 6.53-6.62 (m, 1H), 6.69 (s, 2H), 7.12-7.18 (m, 1H), 7.22 (d, 2H), 7.66 (d, 2H), 7.86 (d, 1H), 8.50 (s, 1H), 9.28 (s, 1H), 11.29 (s, 1H).

Example 16

6-Chloro-N-{3-fluoro-4-[methyl(1H-pyrrolo[2,3-b]pyridin-4-yl)amino]phenyl}pyrimidine-2,4-diamine

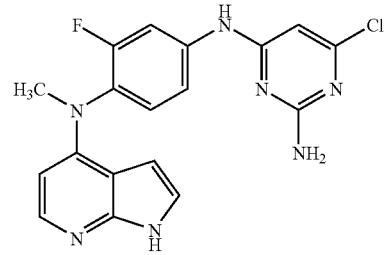

19 mg (0.08 mmol) of N-methyl-N-1H-pyrrolo[2,3-b]pyridin-4-ylbenzene-1,4-diamine and 17 mg (0.11 mmol) of 4,6-dichloropyrimidine-2-amine are suspended in 4 ml of water. 0.11 ml of 1 M hydrochloric acid are added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by column chromatography on silica gel (mobile phase: dichloromethane/methanol (7 M ammonia) 100:1 to 10:1).

Yield: 24 mg (83% of theory)
LC-MS (Method 2): $R_t$=1.50 min.
MS (ESI pos.): m/z=384 (M+H)+.
1H-NMR (DMSO-$d_6$, 400 MHz): δ=3.34 (s, 3H), 5.02-5.10 (m, 1H), 6.05 (s, 1H), 6.39 (d, 1H), 6.89 (s, 2H), 6.90-6.98 (m, 1H), 7.22-7.38 (m, 2H), 7.95 (d, 1H), 8.07 (dd, 1H), 9.63 (s, 1H), 11.24 (s, 1H).

Example 17

6-Chloro-N4-[3-chloro-4-(1H-pyrrolo[2,3-b]pyridin-4-ylamino)phenyl]pyrimidine-2,4-diamine 27 mg (0.10 mmol) of 2-chloro-$N^1$-1H-pyrrolo[2,3-b]pyridin-4-ylbenzene-1,4-diamine and 24 mg (0.15 mmol) of 4,6-dichloropyrimidine-2-amine are suspended in 5 ml of water. 0.14 ml of 1 M hydrochloric acid are added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by preparative HPLC.

Yield: 24 mg (57% of theory)

LC-MS (Method 2): $R_t$=1.54 min.

MS (ESI pos.): m/z=386 (M+H)$^+$.

$^1$H-NMR (DMSO-$d_6$, 400 MHz): δ=6.02 (s, 1H), 6.05 (d, 1H), 6.41-6.49 (m, 1H), 6.83 (s, 2H), 7.09-7.18 (m, 1H), 7.31 (d, 1H), 7.64 (dd, 1H), 7.80 (d, 1H), 8.02 (d, 1H), 8.26 (s, 1H), 9.51 (s, 1H), 11.25 (s, 1H).

Example 18

6-Chloro-$N^4$-{3,5-difluoro-4-[(3-methyl-1H-pyrrolo[2,3-b]pyridin-4-yl)amino]phenyl}pyrimidine-2,4-diamine

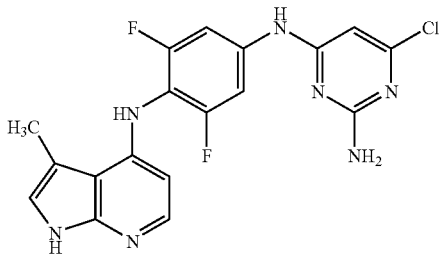

27 mg (0.10 mmol) of 2,6-difluoro-$N^1$-(3-methyl-1H-pyrrolo[2,3-b]pyridin-4-yl)benzene-1,4-diamine and 23 mg (0.14 mmol) of 4,6-dichloropyrimidine-2-amine are suspended in 5 ml of water. 0.14 ml of 1 M hydrochloric acid is added, and the mixture is heated at 100° C. overnight. Using 1N aqueous sodium hydroxide solution, the suspension is then adjusted to pH 10, resulting in the precipitation of crystals. The solid is filtered off and washed with water. The crude product is purified by preparative HPLC.

Yield: 24 mg (61% of theory)

LC-MS (Method 3): $R_t$=1.29 min.

MS (ESI pos.): m/z=402 (M+H)$^+$.

$^1$H-NMR (DMSO-$d_6$, 400 MHz): δ=2.48 (s, 3H), 5.78 (d, 1H), 6.04 (s, 1H), 6.94 (bs. 1H), 6.98 (bs., 2H), 7.19 (s, 1H), 7.59-7.68 (m, 2H), 7.74 (d, 1H), 9.73 (s, 1H), 11.01 (s, 1H).

Example 19

$N^4$-{4-[(3-Chloro-1H-pyrrolo[2,3-b]pyridin-4-yl)methyl]-3-fluorophenyl}-6-(trifluoromethyl)pyrimidine-2,4-diamine

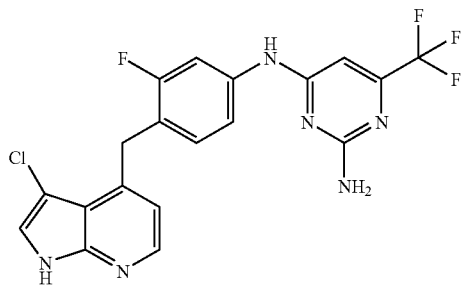

185 mg (0.60 mmol) of 4-[(3-chloro-1H-pyrrolo[2,3-b]pyridin-4-yl)methyl]-3-fluoroaniline and 130 mg (0.66 mmol) of 4-chloro-6-(trifluoromethyl)pyrimidine-2-amine are suspended in 4 ml of water and 0.30 ml of 4N hydrochloric acid. The reaction mixture is heated at reflux for 2 hours.

After cooling, the mixture is made alkaline using dilute aqueous sodium hydroxide solution, a little methanol is added and the mixture is extracted with ethyl acetate. The extract is dried over sodium sulfate and the solvent is removed under reduced pressure. The residue is purified by preparative HPLC. This gives crystals.

Yield: 123 mg (45% of theory)

LC-MS (Method 1): $R_t$=2.32 min.

MS (ESI pos.): m/z=437 [M+H]$^+$.

$^1$H-NMR (DMSO-$d_6$, 400 MHz): δ=4.47 (s, 2H), 6.35 (s, 1H), 6.76 (d, 1H), 6.94 (br. s, 2H), 7.03 (t, 1H), 7.29 (dd, 1H), 7.64 (s, 1H), 7.93 (dd, 1H), 8.18 (d, 1H), 9.75 (s, 1H), 12.00 (s, 1H).

Example 20

4-{4-[(2-Aminopyrimidin-4-yl)amino]-2-fluorobenzyl}-1H-pyrrolo[2,3-b]pyridine-3-carbonitrile

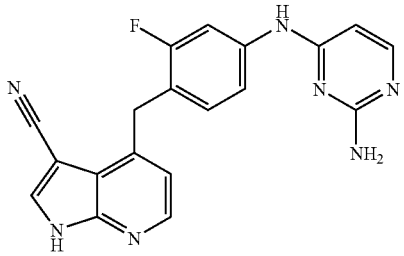

120 mg (0.45 mmol) of 4-(4-amino-2-fluorobenzyl)-1H-pyrrolo[2,3-b]pyridine-3-carbonitrile and 64 mg (0.50 mmol) of 4-chloropyrimidine-2-amine are suspended in 4 ml of water, 2 ml of ethanol and 0.23 ml of 4N hydrochloric acid. The reaction mixture is heated at reflux for 2 hours. After cooling, the mixture is made alkaline using dilute aqueous sodium hydroxide solution, a little methanol is added, the mixture is extracted with ethyl acetate and the solvent is removed under reduced pressure. The residue is purified by preparative HPLC. This gives crystals.

Yield: 111 mg (65% of theory)
LC-MS (Method 3): $R_t$=1.53 min.
MS (ESI pos.): m/z=360 [M+H]$^+$.
$^1$H-NMR (DMSO-d$_6$, 400 MHz): δ=4.39 (s, 2H), 5.99 (d, 1H), 6.29 (br. s, 2H), 6.90 (d, 1H), 7.09 (t, 1H), 7.31 (dd, 1H), 7.82 (d, 1H), 7.91 (dd, 1H), 8.29 (d, 1H), 8.45 (s, 1H), 9.29 (s, 1H), 12.84 (br. s, 1H).

Example 21

4-(4-{[2-Amino-6-(trifluoromethyl)pyrimidin-4-yl]amino}-2-fluorobenzyl)-1H-pyrrolo[2,3-b]pyridine-3-carbonitrile

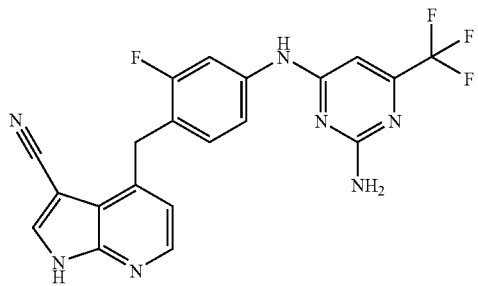

82 mg (0.31 mmol) of 4-(4-amino-2-fluorobenzyl)-1H-pyrrolo[2,3-b]pyridine-3-carbonitrile and 67 mg (0.34 mmol) of 4-chloro-6-trifluoromethylpyrimidine-2-amine are suspended in 3 ml of water, 1.5 ml of ethanol and 0.15 ml of 4N hydrochloric acid. The reaction mixture is heated at reflux for 2 hours. After cooling, the mixture is made alkaline using dilute aqueous sodium hydroxide solution, a little methanol is added, the mixture is extracted with ethyl acetate and the solvent is removed under reduced pressure. The residue is purified by preparative HPLC. This gives crystals.

Yield: 111 mg (65% of theory)
LC-MS (Method 3): $R_t$=2.34 min.
MS (ESI pos.): m/z=428 [M+H]$^+$.
$^1$H-NMR (DMSO-d$_6$, 300 MHz): δ=4.41 (s, 2H), 6.35 (s, 1H), 6.90 (d, 1H), 6.96 (br. s, 2H), 7.14 (t, 1H), 7.32 (dd, 1H), 7.93 (dd, 1H), 8.29 (d, 1H), 8.46 (s, 1H), 9.77 (s, 1H), 12.86 (br. s, 1H).

Example 22

6-Chloro-N$^4$-{3-fluoro-4-[(3-fluoro-1H-pyrrolo[2,3-b]pyridin-4-yl)amino]phenyl}pyrimidine-2,4-diamine

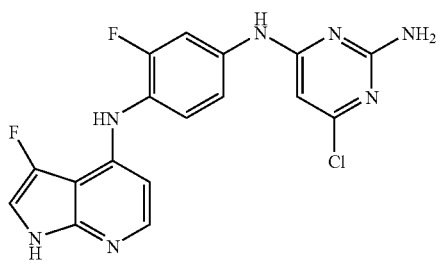

17.9 mg (0.07 mmol) of 2-fluoro-N'-(3-fluoro-1H-pyrrolo[2,3-b]pyridin-4-yl)benzene-1,4-diamine and 12.4 mg (0.076 mmol) of 4,6-dichloropyrimidine-2-amine are suspended in 2 ml of water. 83 μl of 1 M hydrochloric acid are added, and the mixture is heated at 100° C. for 3 h. Using 1N aqueous sodium hydroxide solution, the suspension is then adjusted to pH 10. Dimethyl sulfoxide is added until the precipitate goes into solution, and the solution is purified by preparative HPLC.

Yield: 10.4 mg (39% of theory)
LC-MS (Method 2): $R_t$=1.55 min.
MS (ESI pos.): m/z=388 [M+H]$^+$.
$^1$H-NMR (DMSO-d$_6$, 400 MHz): δ=6.03 (s, 1H), 6.41 (d, 1H), 6.82 (s, 2H), 7.30 (dd, 1H), 7.41 (t, 1H), 7.77 (d, 1H), 7.92 (d, 1H), 8.01 (dd, 1H), 9.51 (s, 1H), 9.89 (s, 1H), 12.30 (br.s, 1H).

Example 23

6-Chloro-N$^4$-(3-fluoro-4-{[3-(trifluoromethyl)-1H-pyrrolo[2,3-b]pyridin-4-yl]amino}phenyl)pyrimidine-2,4-diamine

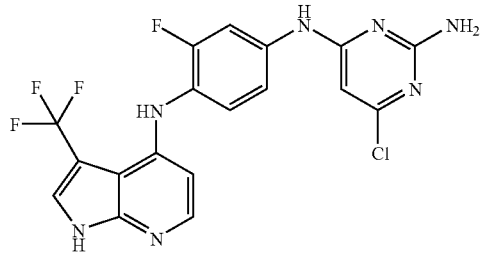

18 mg (0.058 mmol) of 2-fluoro-N'-[3-trifluoromethyl)-1H-pyrrolo[2,3-b]pyridin-4-yl]benzene-1,4-diamine and 10.4 mg (0.064 mmol) of 4,6-dichloropyrimidine-2-amine are suspended in 2 ml of water. 70 μl of 1 M hydrochloric acid are added, and the mixture is heated at 100° C. for 3 h. Using 1N aqueous sodium hydroxide solution, the suspension is then adjusted to pH 10. Dimethyl sulfoxide is added until the precipitate goes into solution, and the solution is purified by preparative HPLC.

Yield: 14 mg (55% of theory)
LC-MS (Method 3): $R_t$=2.01 min.
MS (ESI pos.): m/z=438 [M+H]$^+$.
$^1$H-NMR (DMSO-d$_6$, 400 MHz): δ=6.02 (s, 1H), 6.45 (d, 1H), 6.82 (s, 2H), 7.30 (dd, 1H), 7.42 (t, 1H), 7.94 (d, 1H), 7.97 (s, 1H), 8.03 (dd, 1H), 9.56 (s, 1H), 9.93 (s, 1H), 12.33 (br.s, 1H).

B. Assessment of the Physiological Activity

The inhibition of the enzyme is investigated in an in vitro assay with recombinant Rho kinase II. The vessel-relaxing action is determined using phenylephrine-induced contractions of isolated rings of the saphenous artery of rabbits. The suitability of the compounds according to the invention for treating cardiovascular disorders can be demonstrated by examining the hypotensive effect on anesthetized rats.

Inhibition of Recombinant Rho Kinase II (ROKα)

The activity of Rho kinase is determined by the uptake of $^{33}$P phosphate into a substrate peptide. To this end, commercially available Rho kinase II (Upstate Biotechnology) is pre-incubated at 37° C. in the presence of the S6 phosphate-acceptor peptide with the test substances or a solvent control for 10 min. The kinase reaction is then started by addition of $^{33}$P-labeled ATP. After 20 min at 37° C., the reaction is stopped by addition of H$_3$PO$_4$. Aliquots are pipetted onto filters and the filters are washed and then covered with scintillator. The radioactivity of the $^{33}$P-labeled peptides bound to the filter is measured in a Micro-Beta counter. The IC$_{50}$ value corresponds to the concentration of a test substance at which the Rho-kinase-catalyzed uptake of $^{33}$P into the peptide is inhibited by 50%, compared to a solvent control. The experimental data are summarized in table A below.

TABLE A

| Example No. | IC$_{50}$ (nM) |
|---|---|
| 8 | 7 |
| 10 | 3 |
| 11 | 4 |

Vessel-Relaxing Action In Vitro

Individual 3-mm-wide rings of the isolated saphenous artery of rabbits are introduced into 5 ml organ baths with Krebs-Henseleit solution (37° C., gassed with carbogen). The vessel tone is monitored isometrically and registered. Contractions are induced by addition of $3\times10^{-8}$ g of phenylephrine/ml, which is washed out again after 4 min. After a number of control cycles, the rings are pre-incubated with the substance to be examined, with the dosage being increased for each further cycle, and the subsequent contraction is compared to the intensity of the last control contraction. The concentration required to reduce the intensity of the control value by 50% (IC$_{50}$) is calculated. The experimental data are summarized in table B below.

TABLE B

| Example No. | IC$_{50}$ (nM) |
|---|---|
| 8 | 86 |
| 10 | 8 |
| 11 | 3 |

Measurement of Blood Pressure in Anesthetized Rats

Male Wistar rats of a body weight of 300-350 g are anesthetized with thiopental (100 mg/kg i.p.). Following tracheotomy, a catheter is introduced into the femoral artery to measure the blood pressure. The substances to be tested are administered as solutions, either orally via a stomach tube or intravenously via the femoral vein.

C. Working Examples For Pharmaceutical Compositions

The compounds according to the invention can be converted into pharmaceutical preparations as follows:

Tablet:

Composition:

100 mg of the compound from Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg. Diameter 8 mm, spherical radius 12 mm.

Preparation:

The mixture of inventive compound, lactose and starch is granulated with a 5% strength solution (w/w) of the PVP in water. After drying, the granules are mixed for 5 min with the magnesium stearate. This mixture is compacted in a conventional tablet press (dimensions of the tablet: see above). The standard value used for compacting is a compaction force of 15 kN.

Suspension for Oral Administration:

Composition:

1000 mg of the compound from Example 1, 1000 mg of ethanol (96%), 400 mg of Rhodigel (xanthan gum from FMC, Pennsylvania, USA) and 99 g of water.

A single dose of 100 mg of the compound according to the invention corresponds to 10 ml of oral suspension.

Preparation:

The Rhodigel is suspended in ethanol and the inventive compound is added to the suspension. The water is added with stirring. The mixture is stirred for about 6 h until the Rhodigel is completely swollen.

The invention claimed is:

1. A compound of the formula (I)

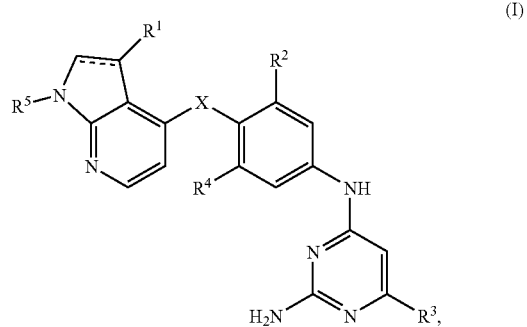

in which

----- represents a single bond or a double bond,

X represents —NR$^6$—, —CR$^7$R$^8$— or —C(=O)—, in which

R$^6$ represents hydrogen or (C$_1$-C$_3$)-alkyl,

R$^7$ and R$^8$ independently of one another represent hydrogen or methyl,

R$^1$ represents hydrogen, halogen, cyano, (C$_1$-C$_6$)-alkyl, (C$_3$-C$_6$)-cycloalkyl, (C$_1$-C$_6$)-alkoxycarbonyl or (C$_1$-C$_6$)-alkylaminocarbonyl, where alkyl, alkoxycarbonyl and alkylaminocarbonyl for their part may be substituted by hydroxyl, halogen, hydroxycarbonyl, (C$_1$-C$_6$)-alkoxy, (C$_1$-C$_6$)-alkoxycarbonyl, amino, aminocarbonyl, (C$_1$-C$_6$)-alkylamino or (C$_1$-C$_6$)-alkylaminocarbonyl, R$^2$ represents fluorine or chlorine, R$^3$ represents a radical selected from the group consisting of:

hydrogen, hydroxyl, halogen, trifluoromethyl, pentafluoroethyl, (C$_1$-C$_6$)-alkyl, (C$_1$-C$_6$)-alkoxy, (C$_3$-C$_8$)-cycloalkyl, where alkyl, alkoxy and cycloalkyl for their part may be substituted by hydroxyl, hydroxycarbonyl, (C$_1$-C$_6$)-alkoxy, (C$_1$-C$_6$)-alkoxycarbonyl, (C$_6$-C$_{10}$)-aryl, —NR$^9$R$^{10}$ or —C(=O)NR$^9$R$^{10}$, in which R$^9$ and R$^{10}$ independently of one another represent hydrogen, (C$_1$-C$_8$)-alkyl, optionally (C$_1$-C$_6$)-alkyl-substituted (C$_3$-C$_6$)-cycloalkyl, optionally halogen-substituted (C$_6$-C$_{10}$)-aryl or 5- to 10-membered heteroaryl or R$^9$ and R$^{10}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, $(C_6-C_{10})$-aryl, $(C_6-C_{10})$-aryloxy, 5- to 10-membered heteroaryl, 5- to 10-membered heteroaryloxy, 5- to 10-membered heterocyclyl which is attached via a carbon atom, where aryl, aryloxy, heteroaryl, heteroaryloxy and heterocyclyl for their part may be substituted by halogen, cyano, nitro, hydroxycarbonyl, amino, trifluoromethyl, optionally hydroxyl-substituted $(C_1-C_6)$-alkyl, $(C_1-C_6)$-alkoxy, $(C_1-C_6)$-alkylamino, $(C_1-C_6)$-alkanoyl, $(C_1-C_6)$-alkoxycarbonyl, $(C_1-C_6)$-alkanoylamino, $(C_1-C_6)$-alkoxycarbonylamino or 5- or 6-membered heterocyclyl,

—$NR^{11}R^{12}$, in which $R^{11}$ and $R^{12}$ independently of one another represent hydrogen, $(C_1-C_6)$-alkyl, $(C_3-C_8)$-cycloalkyl, $(C_6-C_{10})$-aryl or 5- to 10-membered heteroaryl, where alkyl and cycloalkyl for their part may be substituted by hydroxyl, $(C_1-C_6)$-alkoxy, $(C_6-C_{10})$-aryl, 5- to 10-membered heteroaryl or —$NR^{13}R^{14}$, in which $R^{13}$ and $R^{14}$ independently of one another represent hydrogen, $(C_1-C_6)$-alkyl, $(C_3-C_6)$-cycloalkyl, $(C_6-C_{10})$-aryl or 5- or 6-membered heteroaryl or $R^{13}$ and $R^{14}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, and where aryl and heteroaryl for their part may be substituted by halogen, hydroxyl, amino, cyano, trifluoromethyl, $(C_1-C_6)$-alkyl, $(C_1-C_6)$-alkoxy, $(C_1-C_6)$-alkylamino or $(C_1-C_6)$-alkanoylamino, or $R^{11}$ and $R^{12}$ together with the nitrogen atom to which they are attached form a 4- to 6-membered heterocycle which may contain a further heteroatom O or N in the ring and which may be substituted by fluorine, hydroxyl, hydroxycarbonyl, 5- to 7-membered heterocyclyl which may contain one or two further heteroatoms N and/or O in the ring and which for its part may be substituted by $(C_1-C_4)$-alkyl or $(C_1-C_4)$-alkoxycarbonyl, $(C_1-C_4)$-alkoxy, $(C_1-C_4)$-alkyl, $(C_1-C_4)$-alkanoyl, $(C_1-C_4)$-alkoxycarbonyl or —$NR^{15}R^{16}$, where alkyl for its part may be substituted by hydroxyl, $(C_1-C_4)$-alkoxy or —$NR^{17}R^{18}$, where $R^{17}$ and $R^{18}$ independently of one another represent hydrogen, optionally hydroxyl-substituted $(C_1-C_6)$-alkyl, $(C_3-C_6)$-cycloalkyl, $(C_6-C_{10})$-aryl or 5- to 6-membered heteroaryl or $R^{17}$ and $R^{18}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, in which $R^{15}$ and $R^{16}$ independently of one another represent hydrogen, $(C_1-C_6)$-alkyl, $(C_1-C_4)$-alkoxycarbonyl, $(C_3-C_8)$-cycloalkyl or $(C_1-C_4)$-alkanoyl or $R^{15}$ and $R^{16}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, or $R^{11}$ and $R^{12}$ together with the nitrogen atom to which they are attached form a 7- to 12-membered bicyclic or tricyclic heterocycle which is fused or spirocyclic and which may have one or two further heteroatoms from the group consisting of N and O in the ring and which may be substituted by fluorine, $(C_1-C_4)$-alkyl, $(C_1-C_4)$-alkoxycarbonyl, $(C_1-C_4)$-alkanoyl or benzyl, and —$C(=O)R^{19}$, in which $R^{19}$ represents $(C_1-C_6)$-alkoxy, $(C_1-C_6)$-alkylamino or a 5- to 10-membered mono- or bicyclic heterocycle which is attached via a nitrogen atom, which is fused or spirocyclic and which may have one or two further heteroatoms from the group consisting of N and O in the ring, where alkylamino for its part may be substituted by a 5- or 6-membered heterocycle, $R^4$ represents hydrogen, fluorine or chlorine, $R^5$ represents hydrogen or $(C_1-C_6)$-alkyl or a salt thereof.

2. The compound of the formula (I) as claimed in claim 1, in which

= = = = represents a double bond,

X represents —$NR^6$—, —$CH_2$— or —$C(=O)$—, in which $R^6$ represents hydrogen or methyl, $R^1$ represents hydrogen, fluorine, chlorine, cyano, trifluoromethyl, difluoromethyl, methyl, ethyl, hydroxyethyl, methoxyethyl, cyclopropyl, $(C_1-C_6)$-alkoxycarbonyl or $(C_{1-C6})$-alkylaminocarbonyl, where alkoxycarbonyl and alkylaminocarbonyl for their part may be substituted by hydroxyl, hydroxycarbonyl, $(C_1-C_6)$-alkoxy, $(C_1-C_6)$-alkoxycarbonyl, amino, aminocarbonyl, $(C_1-C_6)$-alkylamino or $(C_1-C_6)$-alkylaminocarbonyl, $R^2$ represents fluorine or chlorine, $R^3$ represents a radical selected from the group consisting of:

hydrogen, hydroxyl, halogen, trifluoromethyl, pentafluoroethyl, $(C_1-C_6)$-alkyl, $(C_1-C_6)$-alkoxy, $(C_3-C_8)$-cycloalkyl, where alkyl, alkoxy and cycloalkyl for their part may be substituted by hydroxyl, hydroxycarbonyl, $(C_1-C_6)$-alkoxy, $(C_1-C_6)$-alkoxycarbonyl, $(C_6-C_{10})$-aryl, —$NR^9R^{10}$ or —$C(=O)NR^9R^{10}$, in which $R^9$ and $R^{10}$ independently of one another represent hydrogen or $(C_1-C_8)$-alkyl or $R^9$ and $R^{10}$ together with the nitrogen atom to which they are attached form a 5- or 6-membered heterocycle which may contain a further heteroatom O or N in the ring and which may be substituted by $(C_1-C_6)$-alkyl, $(C_1-C_6)$-alkanoyl or $(C_1-C_6)$-alkoxycarbonyl, phenyl, 5- or 6-membered heteroaryl, 5- to 10-membered heterocyclyl which is attached via a carbon atom, where phenyl, heteroaryl and heterocyclyl for their part may be substituted by halogen, cyano, nitro, hydroxycarbonyl, amino, trifluoromethyl, optionally hydroxyl-substituted $(C_1-C_6)$-alkyl, $(C_1-C_6)$-alkoxy, $(C_1-C_6)$-alkyl-amino, $(C_1-C_6)$-alkanoyl, $(C_1-C_6)$-alkoxycarbonyl, $(C_1-C_6)$-alkanoylamino or $(C_1-C_6)$-alkoxycarbonylamino,

—$NR^{11}R^{12}$, in which $R^{11}$ and $R^{12}$ independently of one another represent hydrogen, $(C_1-C_6)$-alkyl, $(C_3-C_8)$-cycloalkyl, $(C_6-C_{10})$-aryl or 5- to 10-membered heteroaryl, where alkyl and cycloalkyl for their part may be substituted by hydroxyl, $(C_1-C_6)$-alkoxy, $(C_6-C_{10})$-aryl or 5-to 10-membered heteroaryl, and where aryl and heteroaryl for their part may be substituted by halogen, hydroxyl, amino, cyano, trifluoromethyl, $(C_1-C_6)$-alkyl, $(C_1-C_6)$-alkoxy, $(C_1-C_6)$-alkylamino or $(C_1-C_6)$-alkanoylamino, or $R^{11}$ and $R^{12}$ together with the nitrogen atom to which they are attached form a 4- to 6-membered heterocycle which may contain a further heteroatom O or N in the ring and which may be substituted by fluorine, hydroxyl, hydroxycarbonyl, $(C_1-C_4)$-alkoxy, $(C_1-C_4)$-alkyl, $(C_1-C_4)$-alkanoyl or $(C_1-C_4)$-alkoxycarbonyl, and —$C(=O)R^{19}$, in which $R^{19}$ represents $(C_1-C_6)$-alkoxy, $(C_1-C_6)$-alkylamino or a 5-to 10-membered mono- or bicyclic heterocycle which is attached via a nitrogen atom, which is fused or spirocyclic and which may have one or two further heteroatoms from the group consisting of N and O in the ring, where alkylamino for its part may be substituted by a 5- or 6-membered heterocycle, $R^4$ represents hydrogen, fluorine or chlorine, $R^5$ represents hydrogen or methyl, or a salt thereof.

3. The compound of the formula (I) as claimed in claim 1, in which

-----represents a double bond,

X represents —$NR^6$—, —$CH_2$— or —$C(=O)$—, in which $R^6$ represents hydrogen or methyl, $R^1$ represents hydrogen, fluorine, chlorine, cyano, trifluoromethyl, difluoromethyl, methyl, ethyl, hydroxyethyl, methoxyethyl or cyclopropyl, $R^2$ represents fluorine or chlorine, $R^3$ represents a radical selected from the group consisting of:

hydrogen, hydroxyl, halogen, trifluoromethyl, pentafluoroethyl, $(C_1-C_6)$-alkyl, $(C_1-C_6)$-alkoxy, $(C_3-C_8)$-cycloalkyl, where alkyl, alkoxy and cycloalkyl for their part may be substituted by hydroxyl, $(C_1-C_6)$-alkoxy or —$NR^9R^{10}$, in which $R^9$ and $R^{10}$ independently of one another represent hydrogen or $(C_1-C_8)$-alkyl or $R^9$ and $R^{10}$ together with the nitrogen atom to which they are attached form a 5- or 6-membered heterocycle which may contain a further heteroatom O or N in the ring and which may be substituted by $(C_1-C_3)$-alkyl or $(C_1-C_3)$-alkanoyl, phenyl and 5- or 6-membered heteroaryl, where phenyl and heteroaryl for their part may be substituted by halogen, amino or trifluoromethyl, $R^4$ represents hydrogen, fluorine or chlorine, $R^5$ represents hydrogen or methyl, or a salt thereof.

4. The compound of the formula (I) as claimed in claim 1 in which

-----represents a double bond,

X represents —NH— or —$CH_2$—, $R^1$ represents hydrogen, chlorine or methyl, $R^2$ represents fluorine, $R^3$ represents a radical selected from the group consisting of hydrogen, halogen, trifluoromethyl, optionally halogen-substituted phenyl and pyridine, $R^4$ represents hydrogen or fluorine, $R^5$ represents hydrogen, or a salt thereof.

5. A process for preparing a compound of the formula (I) as defined in claim 1, characterized in that a compound of the formula (II)

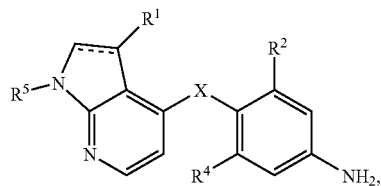

in which

-----, X, $R^1$, $R^2$, $R^4$ and $R^5$ are as defined in claim 1 are reacted with a compound of the formula (III)

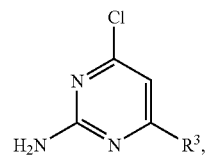

in which $R^3$ is as defined in claim 1, which, if X represents a $CH_2$ group, may be followed by an oxidation to give the corresponding keto group —C(=O)— or a methylation to give the corresponding mono- or dimethyl compound [—CH(CH$_3$)— or —C(CH$_3$)$_2$—].

6. A pharmaceutical composition, comprising a compound of the formula (I) as defined in claim 1 in combination with a further active compound.

7. A pharmaceutical composition, comprising a compound of the formula (I) as defined in claim 1 in combination with an inert nontoxic pharmaceutically acceptable auxiliary.

8. A method for the treatment of erectile dysfunction in a human or an animal comprising administering to said human or animal an effective amount of a compound of formula (I) as define in claim 1.

9. A method for the treatment of hypertension in a human or an animal comprising administering to said human or animal an effective amount of a compound of formula (I) as define in claim 1.

* * * * *